US010018911B2

(12) United States Patent
Nakagawa et al.

(10) Patent No.: US 10,018,911 B2
(45) Date of Patent: Jul. 10, 2018

(54) CHEMICALLY AMPLIFIED RESIST MATERIAL AND RESIST PATTERN-FORMING METHOD

(71) Applicant: JSR CORPORATION, Tokyo (JP)

(72) Inventors: Hisashi Nakagawa, Tokyo (JP); Takehiko Naruoka, Tokyo (JP); Tomoki Nagai, Tokyo (JP)

(73) Assignee: JSR CORPORATION, Tokyo (JP)

( * ) Notice: Subject to any disclaimer, the term of this patent is extended or adjusted under 35 U.S.C. 154(b) by 0 days.

(21) Appl. No.: 15/347,033

(22) Filed: Nov. 9, 2016

(65) Prior Publication Data

US 2017/0131633 A1 May 11, 2017

(30) Foreign Application Priority Data

Nov. 9, 2015 (JP) ................................. 2015-219984
Aug. 8, 2016 (JP) ................................. 2016-156025
Nov. 7, 2016 (JP) ................................. 2016-217575

(51) Int. Cl.
G03F 7/004 (2006.01)
G03F 7/16 (2006.01)
(Continued)

(52) U.S. Cl.
CPC .......... *G03F 7/0046* (2013.01); *C07C 381/12* (2013.01); *C07D 307/77* (2013.01);
(Continued)

(58) Field of Classification Search
CPC ........ G03F 7/004; G03F 7/0046; G03F 7/168; G03F 7/2022; G03F 7/0397; G03F 7/38;
(Continued)

(56) References Cited

U.S. PATENT DOCUMENTS 7,510,822 B2 * 3/2009 Kodama ............... C07C 381/12
430/270.1
8,124,326 B2 * 2/2012 Shirley ................. G03F 7/2022
430/322
(Continued)

FOREIGN PATENT DOCUMENTS

EP 0 622 682 A1 11/1994
JP H04-151156 A 5/1992
(Continued)

OTHER PUBLICATIONS

S. Tagawa et al., "Super High Sensitivity Enhancement by Photo-Sensitized Chemically Amplified Resist (PS-CAR) Process", Journal of Photopolymer Science & Technology, 2013, vol. 26, No. 6, pp. 825-830.

(Continued)

Primary Examiner — Amanda C Walke
(74) Attorney, Agent, or Firm — Oblon, McClelland, Maier & Neustadt, L.L.P.

(57) ABSTRACT

A chemically amplified resist material comprises a polymer component that is capable of being made soluble or insoluble in a developer solution by an action of an acid, and a generative component that is capable of generating a radiation-sensitive sensitizer and an acid upon an exposure. The radiation-sensitive acid-and-sensitizer generating agent or the radiation-sensitive acid generating agent included in the generative component comprises the first compound that is radiation-sensitive and second compound that is radiation-sensitive. The first compound includes a first onium cation and a first anion, and the second compound includes a second onium cation and a second anion that is different from the first anion. Each of an energy released upon reduction of the first onium cation to a radical and an energy (Continued)

released upon reduction of the second onium cation to a radical is less than 5.0 eV.

15 Claims, 8 Drawing Sheets

(51) Int. Cl.
| | |
|---|---|
| G03F 7/039 | (2006.01) |
| G03F 7/20 | (2006.01) |
| C07C 381/12 | (2006.01) |
| G03F 7/38 | (2006.01) |
| H01L 21/027 | (2006.01) |
| C07D 307/77 | (2006.01) |
| C08F 220/38 | (2006.01) |
| C08F 220/18 | (2006.01) |
| C08F 220/26 | (2006.01) |
| C08F 220/24 | (2006.01) |
| C08F 220/22 | (2006.01) |

(52) U.S. Cl.
CPC .......... *C08F 220/18* (2013.01); *C08F 220/22* (2013.01); *C08F 220/24* (2013.01); *C08F 220/26* (2013.01); *C08F 220/38* (2013.01); *G03F 7/0397* (2013.01); *G03F 7/168* (2013.01); *G03F 7/2022* (2013.01); *G03F 7/38* (2013.01); *H01L 21/0274* (2013.01)

(58) Field of Classification Search
CPC . H01L 21/2074; C07C 381/12; C07D 307/77; C08F 220/18; C08F 220/38; C08F 220/24; C08F 220/26; C08F 220/22
USPC ..... 430/270.1, 394, 330, 331, 913; 526/243, 526/281; 560/9
See application file for complete search history.

(56) References Cited

U.S. PATENT DOCUMENTS

| | | | | |
|---|---|---|---|---|
| 2006/0269879 | A1* | 11/2006 | Elian | G03F 7/203 430/394 |
| 2012/0237874 | A1* | 9/2012 | Yamaguchi | C07C 309/06 430/281.1 |
| 2013/0157197 | A1* | 6/2013 | Komuro | G03F 7/027 430/285.1 |
| 2013/0224659 | A1* | 8/2013 | Ohashi | C08F 220/18 430/285.1 |
| 2013/0344435 | A1* | 12/2013 | Utsumi | G03F 7/039 430/270.1 |
| 2015/0086926 | A1* | 3/2015 | Ohashi | C07C 381/12 430/285.1 |
| 2016/0004160 | A1* | 1/2016 | Tagawa | G03F 7/38 430/296 |
| 2016/0195809 | A1* | 7/2016 | Ochiai | G03F 7/038 430/270.1 |
| 2016/0246175 | A1* | 8/2016 | Kotake | G03F 7/0392 |
| 2016/0349612 | A1* | 12/2016 | Fujiwara | C08F 220/38 |
| 2016/0357103 | A1 | 12/2016 | Nagahara et al. | |

FOREIGN PATENT DOCUMENTS

| | | |
|---|---|---|
| JP | H04-162040 A | 6/1992 |
| JP | H05-005995 A | 1/1993 |
| JP | H05-197148 A | 8/1993 |
| JP | H06-194834 A | 7/1994 |
| JP | H08-146608 A | 6/1996 |
| JP | H10-083079 A | 3/1998 |
| JP | 2002-174894 A | 6/2002 |
| JP | 2008-543033 A | 11/2008 |
| JP | 2015-61831 A | 4/2015 |
| JP | 2015-78366 A | 4/2015 |
| JP | 2015-98471 A | 5/2015 |
| JP | 2015-134904 A | 7/2015 |
| JP | 2015-187252 A | 10/2015 |
| WO | WO 2006/125509 A2 | 11/2006 |
| WO | WO 2011/086389 A1 | 7/2011 |
| WO | WO 2014/129556 A1 | 8/2014 |
| WO | WO 2014/185065 A1 | 11/2014 |
| WO | WO 2014/208076 A1 | 12/2014 |
| WO | WO 2014/208102 A1 | 12/2014 |
| WO | WO 2014/208103 A1 | 12/2014 |
| WO | WO 2014/208104 A1 | 12/2014 |
| WO | WO 2015/019616 A1 | 2/2015 |
| WO | WO 2015/022779 A1 | 2/2015 |
| WO | WO 2015/049871 A1 | 4/2015 |
| WO | WO 2015/052914 A1 | 4/2015 |
| WO | WO 2015/125788 A1 | 8/2015 |
| WO | WO 2015/178464 A1 | 11/2015 |

OTHER PUBLICATIONS

U.S. Appl. No. 15/347,033, filed Nov. 9, 2016, Nakagawa, et al.
U.S. Appl. No. 15/239,136, filed Aug. 17, 2016, Nakagawa, et al.
U.S. Appl. No. 15/241,274, filed Aug. 19, 2016, Nakagawa, et al.
U.S. Appl. No. 15/241,315, filed Aug. 19, 2016, Nakagawa, et al.
U.S. Appl. No. 15/241,345, filed Aug. 19, 2016, Nakagawa, et al.
U.S. Appl. No. 15/259,160, filed Sep. 8, 2016, Nakagawa, et al.
U.S. Appl. No. 15/259,200, filed Sep. 8, 2016, Nakagawa, et al.
U.S. Appl. No. 15/347,113, filed Nov. 9, 2016, Nakagawa, et al.

* cited by examiner

BACKGROUND ART

CHEMICALLY AMPLIFIED RESIST MATERIAL AND RESIST PATTERN-FORMING METHOD

CROSS-REFERENCE TO RELATED APPLICATIONS

The present application claims priority to Japanese Patent Application No. 2015-219984, filed Nov. 9, 2015, to Japanese Patent Application No. 2016-156025, filed Aug. 8, 2016, and to Japanese Patent Application No. 2016-217575, filed Nov. 7, 2016. The contents of these applications are incorporated herein by reference in their entirety.

BACKGROUND OF THE INVENTION

Field of the Invention

The present invention relates to a chemically amplified resist material, and a resist pattern-forming method.

Discussion of the Background

Lithography in which EUV (extreme-ultraviolet) is utilized (hereinafter, may be referred to as "EUV lithography") attracts attention as one of element technologies for manufacture of the next-generation semiconductor devices. The EUV lithography is a pattern formation technology in which EUV having a wavelength of 13.5 nm is utilized as an exposure light. It is demonstrated that the EUV lithography enables an extremely fine pattern (line width: no greater than 20 nm, for example) to be formed in an exposure step of a manufacture process of the semiconductor devices.

However, since hitherto-developed EUV light sources have low power, the exposure treatment requires a long time period. Thus, the EUV lithography has a disadvantage of being inferior in practical use. To overcome this disadvantage, a technique for increasing the sensitivity of a resist material which is a photosensitive resin has been developed (see Japanese Unexamined Patent Application, Publication No. 2002-174894).

SUMMARY OF THE INVENTION

According to one aspect of the present invention, a chemically amplified resist material comprises a polymer component that is capable of being made soluble or insoluble in a developer solution by an action of an acid, and a generative component that is capable of generating a radiation-sensitive sensitizer and an acid upon an exposure. The generative component comprises a radiation-sensitive acid-and-sensitizer generating agent, any two of the radiation-sensitive acid-and-sensitizer generating agent, a radiation-sensitive sensitizer generating agent and a radiation-sensitive acid generating agent, or all the radiation-sensitive acid-and-sensitizer generating agent, the radiation-sensitive sensitizer generating agent and the radiation-sensitive acid generating agent. The radiation-sensitive acid-and-sensitizer generating agent is capable of generating, upon an exposure to a first radioactive ray having a wavelength of no greater than 250 nm without an exposure to a second radioactive ray having a wavelength of greater than 250 nm, an acid and a radiation-sensitive sensitizer that absorbs the second radioactive ray, but the radiation-sensitive acid-and-sensitizer generating agent substantially does not generate the acid and the radiation-sensitive sensitizer upon an exposure to the second radioactive ray without an exposure to the first radioactive ray. The radiation-sensitive sensitizer generating agent is capable of generating, upon the exposure to the first radioactive ray without the exposure to the second radioactive ray, a radiation-sensitive sensitizer that absorbs the second radioactive ray, but the radiation-sensitive sensitizer generating agent substantially does not generate the radiation-sensitive sensitizer upon the exposure to the second radioactive ray without the exposure to the first radioactive ray. The radiation-sensitive acid generating agent is capable of generating an acid upon the exposure to the first radioactive ray without the exposure to the second radioactive ray, but the radiation-sensitive acid generating agent substantially does not generate the acid upon the exposure to the second radioactive ray without the exposure to the first radioactive ray. The radiation-sensitive acid-and-sensitizer generating agent or the radiation-sensitive acid generating agent comprises a first compound that is radiation-sensitive and a second compound that is radiation-sensitive. The first compound comprises a first onium cation and a first anion, and the second compound comprises a second onium cation and a second anion that is different from the first anion. Each of an energy released upon reduction of the first onium cation to a radical and an energy released upon reduction of the second onium cation to a radical is less than 5.0 eV.

According to another aspect of the present invention, a resist pattern-forming method comprises applying the chemically amplified resist material on at least one face of a substrate to form a resist material film. The resist material film is patternwise exposed to a radioactive ray having a wavelength of no greater than 250 nm. The resist material film patternwise exposed is floodwise exposed to a radioactive ray having a wavelength of greater than 250 nm. The resist material film floodwise exposed is based. The resist material film baked is developed with a developer solution.

BRIEF DESCRIPTION OF THE DRAWINGS

FIGS. 6A to 6C show cross-sectional views explaining an example of the manufacturing steps of the semiconductor device according to an embodiment of the present invention, in which FIG. 6A is a cross-sectional view illustrating the resist pattern forming step, FIG. 6B is a cross sectional view illustrating the etching step, and FIG. 6C is a cross sectional view illustrating the resist pattern removing step;

DESCRIPTION OF THE EMBODIMENTS

Figure 1:
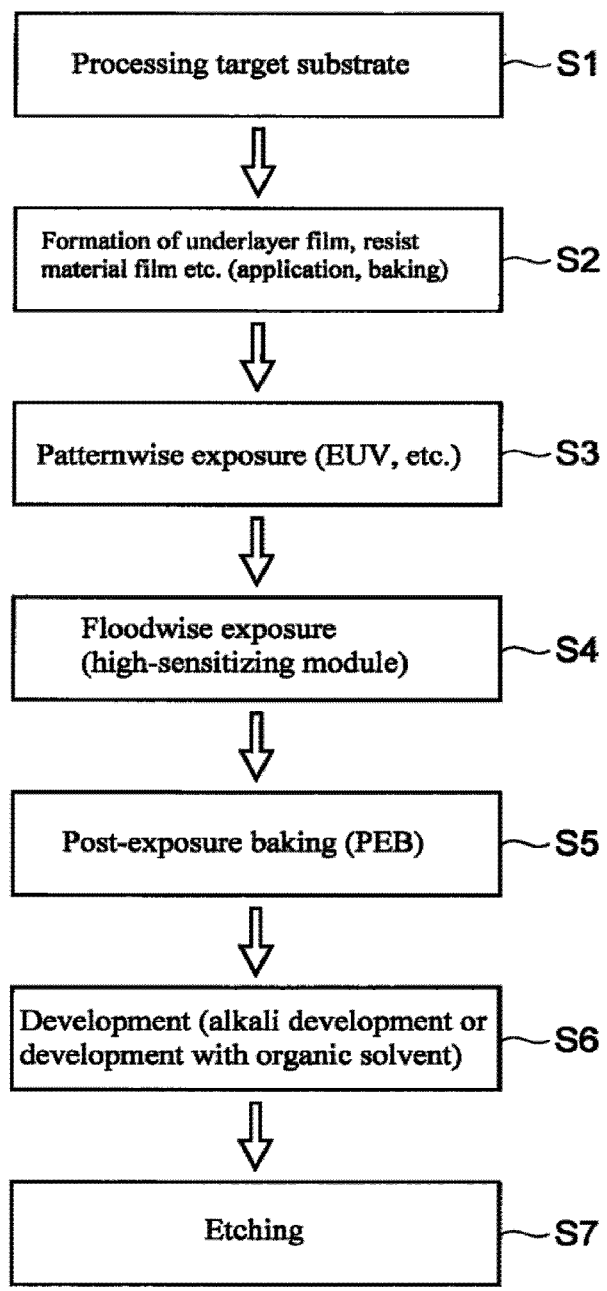
FIG. 1 shows a flow chart illustrating one embodiment of the resist pattern-forming method employing the chemically amplified resist material according to an embodiment of the present invention.

According to an embodiment of the invention, a chemically amplified resist material contains: (1) a polymer component that is capable of being made soluble or insoluble in a developer solution by an action of an acid; and (2) a component (may be also referred to as "generative component") that is capable of generating a radiation-sensitive sensitizer and an acid upon an exposure, wherein the generative component (2) contains the following component (a), any two of the following components (a) to (c), or all of the following components (a) to (c):

(a) a radiation-sensitive acid-and-sensitizer generating agent that is capable of generating, upon an exposure to a first radioactive ray having a wavelength of no greater than 250 nm without an exposure to a second radioactive ray having a wavelength of greater than 250 nm, an acid and a radiation-sensitive sensitizer that absorbs the second radioactive ray, but the radiation-sensitive acid-and-sensitizer generating agent substantially does not generate the acid and the radiation-sensitive sensitizer upon an exposure to the second radioactive ray without an exposure to the first radioactive ray;

(b) a radiation-sensitive sensitizer generating agent that is capable of generating, upon the exposure to the first radioactive ray without the exposure to the second radioactive ray, the radiation-sensitive sensitizer that absorbs the second radioactive ray, but the radiation-sensitive sensitizer generating agent substantially does not generate the radiation-sensitive sensitizer upon the exposure to the second radioactive ray without the exposure to the first radioactive ray; and (c) a radiation-sensitive acid generating agent that is capable of generating an acid upon the exposure to the first radioactive ray without the exposure to the second radioactive ray, but the radiation-sensitive acid generating agent substantially does not generate the acid upon the exposure to the second radioactive ray without the exposure to the first radioactive ray, wherein the component (a) or the component (c) includes a first compound that is radiation-sensitive (hereinafter, may be also referred to as "(C1) compound" or "compound (C1)") and a second compound that is radiation-sensitive (hereinafter, may be also referred to as "(C2) compound" or "compound (C2)"), wherein the compound (C1) has a first onium cation (hereinafter, may be also referred to as "cation (I)") and a first anion (hereinafter, may be also referred to as "anion (I)") and wherein the compound (C2) has a second onium cation (hereinafter, may be also referred to as "cation (II)") and a second anion (hereinafter, may be also referred to as "anion (II)") that is different from the anion (I), and wherein each of an energy released upon reduction of the cation (I) to a radical and an energy released upon reduction of the cation (II) to a radical is less than 5.0 eV.

According to another embodiment of the invention, a resist pattern-forming method includes: a film-forming step of forming a resist material film on at least one face of a substrate using the chemically amplified resist material according to the embodiment of the present invention; a patternwise exposure step of patternwise exposing the resist material film to a radioactive ray having a wavelength of no greater than 250 nm; a floodwise exposure step of floodwise exposing the resist material film obtained after the patternwise exposure step to a radioactive ray having a wavelength of greater than 250 nm; a baking step of baking the resist material film obtained after the floodwise exposure step; and a development step of developing the resist material film obtained after the baking step with a developer solution.

The phrases "substantially does not generate the acid and the radiation-sensitive sensitizer upon an/the exposure to (or, irradiation with) the second radioactive ray without an/the exposure to (or, irradiation with) the first radioactive ray", "substantially does not generate the radiation-sensitive sensitizer upon an/the exposure to (or, irradiation with) the second radioactive ray without an/the exposure to (or, irradiation with) the first radioactive ray" and "substantially does not generate the acid upon an/the exposure to (or, irradiation with) the second radioactive ray without an/the exposure to (or, irradiation with) the first radioactive ray" as referred to mean that the acid and/or the radiation-sensitive sensitizer is/are not generated through the exposure to (or, irradiation with) the second radioactive ray, or that even in the case where the acid and/or the radiation-sensitive sensitizer is/are generated through the exposure to (or, irradiation with) the second radioactive ray, the amount of the acid and/or the radiation-sensitive sensitizer generated in the regions unexposed in the patternwise exposure, i.e., the second radioactive ray is so small that the difference in the concentration of the acid and/or the radiation-sensitive sensitizer between the light-exposed regions and the light-unexposed regions in the patternwise exposure in which the irradiation with the first radioactive ray is conducted can be maintained at a level to permit the pattern formation, and consequently the amount of the acid and/or the radiation-sensitive sensitizer thus generated is so small that either the exposed regions or the unexposed regions alone in the patternwise exposure can be dissolved in the developer solution in the development step.

According to the chemically amplified resist material of the embodiment of the present invention, superior lithography performances can be achieved while favorable sensitivity is maintained in a case where an ionizing radiation such as EUV, an electron beam and an ion beam, or a nonionizing radiation having a wavelength of no greater than 250 nm such as a KrF excimer laser and an ArF excimer laser is used as the patterning exposure light. Moreover, the chemically amplified resist material can be suitably used in the resist pattern-forming method of the embodiment of the present invention.

Hereinafter, embodiments of the present invention will be described in detail. It is to be noted that the present invention is not limited to the following embodiments.

Chemically Amplified Resist Material

The chemically amplified resist material according to an embodiment of the present invention contains: (1) a polymer component that is capable of being made soluble or insoluble in a developer solution by an action of an acid; and (2) a generative component that is capable of generating a radiation-sensitive sensitizer and an acid upon an exposure, wherein the generative component (2) contains the following component (a), any two of the following components (a) to (c), or all of the following components (a) to (c):

(a) a radiation-sensitive acid-and-sensitizer generating agent that is capable of generating, upon the irradiation with a first radioactive ray having a wavelength of no greater than 250 nm without the irradiation with a second radioactive ray having a wavelength of greater than 250 nm, an acid and a radiation-sensitive sensitizer that absorbs the second radioactive ray, but the radiation-sensitive acid-and-sensitizer generating agent substantially does not generate the acid and the radiation-sensitive sensitizer upon the irradiation with the second radioactive ray without the irradiation with the first radioactive ray;

(b) a radiation-sensitive sensitizer generating agent that is capable of generating, upon the irradiation with the first radioactive ray without the irradiation with the second radioactive ray, a radiation-sensitive sensitizer that absorbs the second radioactive ray, but the radiation-sensitive sensitizer generating agent substantially does not generate the radiation-sensitive sensitizer upon the irradiation with the second radioactive ray without the irradiation with the first radioactive ray; and (c) a radiation-sensitive acid generating agent that is capable of generating an acid upon the irradiation with the first radioactive ray without the irradiation with the second radioactive ray, but the radiation-sensitive acid generating agent substantially does not generate the acid upon the irradiation with the second radioactive ray without the irradiation with the first radioactive ray.

The chemically amplified resist material may typically contain a solvent in addition to the polymer component (1) and the generative component (2), and may further contain an acid diffusion control agent, radical trapping agent, crosslinking agent, other additive, and the like.

Herein, the generative component (2) may be incorporated into a part of a polymer constituting the polymer component (1), and may be a component that is different from the polymer component (1). In this case, a part of the generative component (2) may be a component that is different from the polymer component (1), or the entirety of the generative component (2) may be a component that is different from the polymer component (1).

The upper limit of the wavelength of the first radioactive ray is preferably 250 nm, and more preferably 200 nm. On the other hand, the lower limit of the wavelength of the second radioactive ray preferably exceeds 250 nm, and more preferably is 300 nm. The upper limit of the wavelength of the second radioactive ray is preferably 500 nm, and more preferably 400 nm.

(1) Polymer Component

The polymer component (1) is a component that is capable of being made soluble or insoluble in a developer solution by an action of an acid. The polymer component (1) contains a first polymer (hereinafter, may be also referred to as "(A) polymer" or "polymer (A)") having a first structural unit (hereinafter, may be also referred to as "structural unit (I)") that includes a group that is capable of generating a polar group by an action of an acid (hereinafter, may be also referred to as "acid-labile group"), and the like. The polymer component (1) may further contain a second polymer (hereinafter, may be also referred to as "(B) polymer" or "polymer (B)") not having the structural unit (I) as long as the polymer (A) is included.

The polymer (A) or the polymer (B) may further have a structural unit that includes: a fluorine atom (hereinafter, may be also referred to as "structural unit (II)"); and a structural unit (III) that includes a phenolic hydroxyl group and a structural unit (IV) that includes a lactone structure, a cyclic carbonate structure, a sultone structure or a combination thereof, and may further have other structural unit than the structural units (I) to (IV).

(A) Polymer and (B) Polymer

The polymer (A) has the structural unit (I). The polymer (A) may further have structural units (II) to (IV), as well as other structural unit. The polymer (B) is different from the polymer (A). The polymer (B) preferably has the structural unit (II), and may have the structural unit (III) and the structural unit (IV), as well as other structural unit than the structural units (III) to (IV).

Structural Unit (I)

The structural unit (I) includes an acid-labile group. When the polymer (A) has the structural unit (I), the sensitivity and lithography performances of the chemically amplified resist material can be further improved. The structural unit (I) is exemplified by a structural unit represented by the following formula (a-1) (hereinafter, may be also referred to as "structural unit (I-1)"), a structural unit represented by the following formula (a-2) (hereinafter, may be also referred to as "structural unit (1-2)"), and the like. In the following formulae (a-1) and (a-2), the group represented by —$CR^{A2}R^{A3}R^{A4}$ or —$CR^{A6}R^{A7}R^{A8}$ corresponds to the acid-labile group.

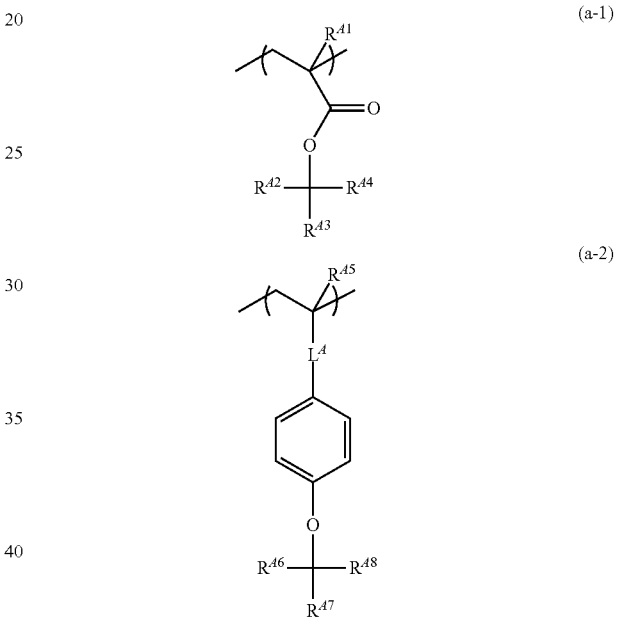

In the above formula (a-1), $R^{A1}$ represents a hydrogen atom, a fluorine atom, a methyl group or a trifluoromethyl group; $R^{A2}$ represents a monovalent hydrocarbon group having 1 to 20 carbon atoms; $R^{A3}$ and $R^{A4}$ each independently represent a monovalent chain hydrocarbon group having 1 to 20 carbon atoms or a monovalent alicyclic hydrocarbon group having 3 to 20 carbon atoms, or these groups taken together represent alicyclic structure having 3 to 20 ring atoms together with the carbon atom to which these groups bond.

In the above formula (a-2), $R^{A5}$ represents a hydrogen atom, a fluorine atom, a methyl group or a trifluoromethyl group; $R^{A6}$ represents a hydrogen atom, a monovalent hydrocarbon group having 1 to 20 carbon atoms or a monovalent oxyhydrocarbon group having 1 to 20 carbon atoms; $R^{A7}$ and $R^{A8}$ each independently represent a monovalent hydrocarbon group having 1 to 20 carbon atoms or a monovalent oxyhydrocarbon group having 1 to 20 carbon atoms; and $L^A$ represents a single bond, —O—, —COO— or —CONH—.

The monovalent hydrocarbon group having 1 to 20 carbon atoms which may be represented by $R^{A2}$, $R^{A6}$, $R^{A7}$ or $R^{A8}$ is exemplified by a chain hydrocarbon group having 1 to 30 carbon atoms, an alicyclic hydrocarbon group having 3 to 30 carbon atoms, an aromatic hydrocarbon group having 6 to 30 carbon atoms, and the like.

Examples of the monovalent chain hydrocarbon group having 1 to 30 carbon atoms include:

alkyl groups such as a methyl group, an ethyl group, a n-propyl group and an i-propyl group;

alkenyl groups such as an ethenyl group, a propenyl group and a butenyl group;

alkynyl groups such as an ethynyl group, a propynyl group and a butynyl group; and the like.

Examples of the monovalent alicyclic hydrocarbon group having 3 to 30 carbon atoms include:

saturated monocyclic hydrocarbon groups such as a cyclopropyl group, a cyclobutyl group, a cyclopentyl group, a cyclohexyl group, a cyclopentyl group, a cyclooctyl group, a cyclodecyl group and a cyclododecyl group;

unsaturated monocyclic hydrocarbon groups such as a cyclopropenyl group, a cyclobutenyl group, a cyclopentenyl group, a cyclohexenyl group, a cyclooctenyl group and a cyclodecenyl group;

saturated polycyclic hydrocarbon groups such as a bicyclo[2.2.1]heptanyl group, a bicyclo[2.2.2]octanyl group and a tricyclo[3.3.1.1$^{3,7}$]decanyl group;

unsaturated polycyclic hydrocarbon groups such as a bicyclo[2.2.1]heptenyl group and a bicyclo[2.2.2]octenyl group; and the like.

Examples of the monovalent aromatic hydrocarbon group having 6 to 30 carbon atoms include:

aryl groups such as a phenyl group, a tolyl group, a xylyl group, a mesityl group, a naphthyl group, a methylnaphthyl group, an anthryl group and a methylanthryl group;

aralkyl groups such as a benzyl group, a phenethyl group, a naphthylmethyl group and an anthrylmethyl group; and the like.

$R^{42}$ represents preferably a chain hydrocarbon group or a cycloalkyl group, more preferably an alkyl group or a cycloalkyl group, and still more preferably a methyl group, an ethyl group, a propyl group, a cyclopentyl group, a cyclohexyl group, a cyclooctyl group or an adamantyl group.

Examples of the monovalent chain hydrocarbon group having 1 to 20 carbon atoms and monovalent alicyclic hydrocarbon group having 3 to 20 carbon atoms which may be represented by $R^{43}$ or $R^{44}$ include groups similar to those exemplified in connection with $R^{42}$, $R^{46}$, $R^{47}$ and $R^{48}$, and the like.

Examples of the alicyclic structure having 3 to 20 ring atoms which may be taken together represented by the groups $R^{43}$ and $R^{44}$ together with the carbon atom to which $R^{43}$ and $R^{44}$ bond include:

monocyclic cycloalkane structures such as a cyclopropane structure, a cyclobutane structure, a cyclopentane structure, a cyclopentene structure, a cyclopentadiene structure, a cyclohexane structure, a cyclooctane structure and a cyclodecane structure;

polycyclic cycloalkane structures such as a norbornane structure, an adamantane structure, a tricyclodecane structure and a tetracyclododecane structure; and the like.

$R^{43}$ and $R^{44}$ represent preferably an alkyl group, a monocyclic cycloalkane structure taken together represented by $R^{43}$ and $R^{44}$ together with the carbon atom to which $R^{43}$ and $R^{44}$ bond, a norbornane structure or an adamantane structure, and more preferably a methyl group, an ethyl group, a cyclopentane structure, a cyclohexane structure or an adamantane structure.

Examples of the monovalent oxyhydrocarbon group having 1 to 20 carbon atoms which may be represented by $R^{46}$, $R^{47}$ or $R^{48}$ include groups obtained by incorporating an oxygen atom between two adjacent carbon atoms of the monovalent hydrocarbon group having 1 to 20 carbon atoms which may be represented by $R^{42}$, $R^{46}$, $R^{47}$ and $R^{48}$, and the like.

$R^{46}$, $R^{47}$ and $R^{48}$ preferably represent a chain hydrocarbon group, and an oxygen atom-containing alicyclic hydrocarbon group.

$L^A$ represents preferably a single bond or —COO—, and more preferably a single bond.

In light of the copolymerizability of a monomer that gives the structural unit (I), $R^{41}$ represents preferably a hydrogen atom or a methyl group, and more preferably a methyl group.

In light of the copolymerizability of a monomer that gives the structural unit (I), $R^{45}$ represents preferably a hydrogen atom or a methyl group, and more preferably a hydrogen atom.

Examples of the structural unit (I-1) include structural units represented by the following formulae (a-1-a) to (a-1-d) (hereinafter, may be also referred to as "structural units (I-1-a) to (I-1-d)"), and the like. Examples of the structural unit (1-2) include a structural unit represented by the following formula (a-2-a) (hereinafter, may be also referred to as "structural unit (I-2-a)"), and the like.

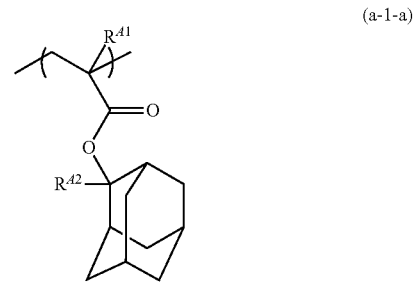

(a-1-a)

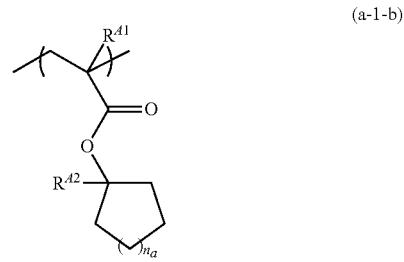

(a-1-b)

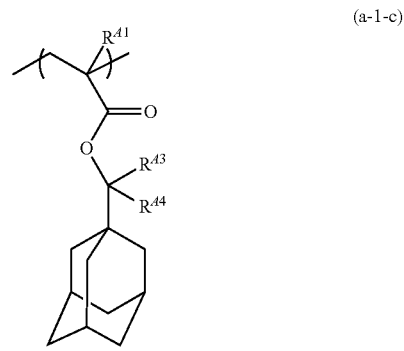

(a-1-c)

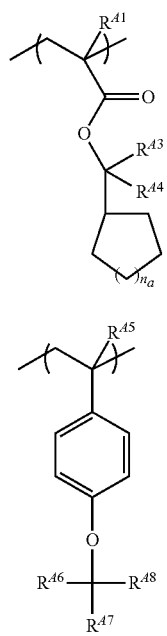
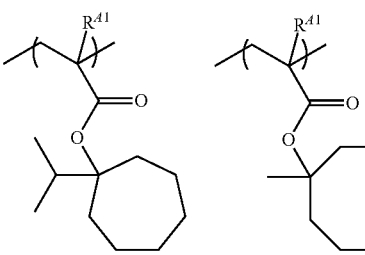
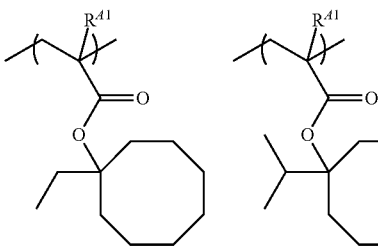
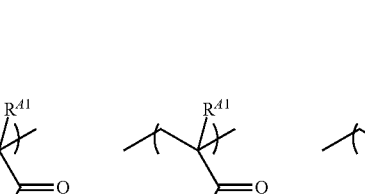
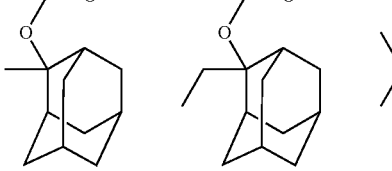

In the above formulae (a-1-a) to (a-1-d), $R^{A1}$ to $R^{A4}$ are as defined in the above formula (a-1); and $n_a$ is an integer of 1 to 4. In the above formula (a-2-a), $R^{A5}$ to $R^{A8}$ are as defined in the above formula (a-2).

In the above formulae (a-1-b) and (a-1-d), $n_a$ is preferably 1, 2 or 4, and more preferably 1.

Examples of the structural units (I-1-a) to (I-1-d) include structural units represented by the following formulae, and the like.

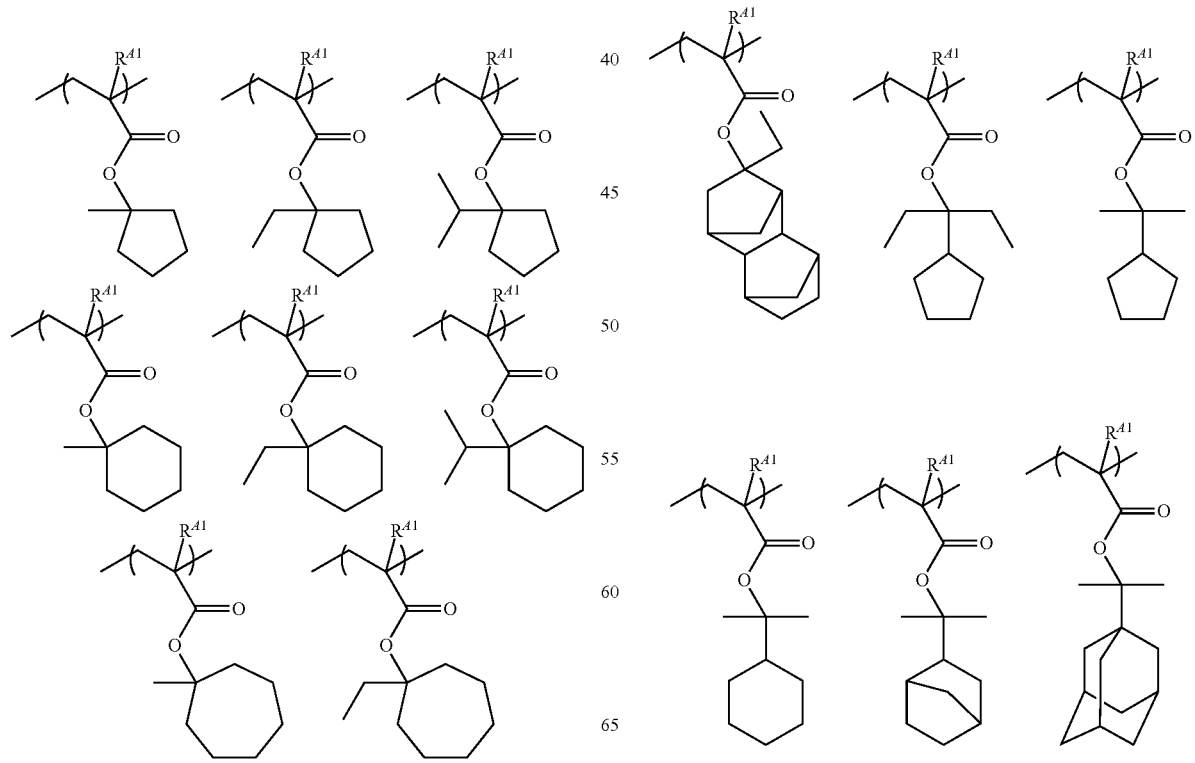

-continued

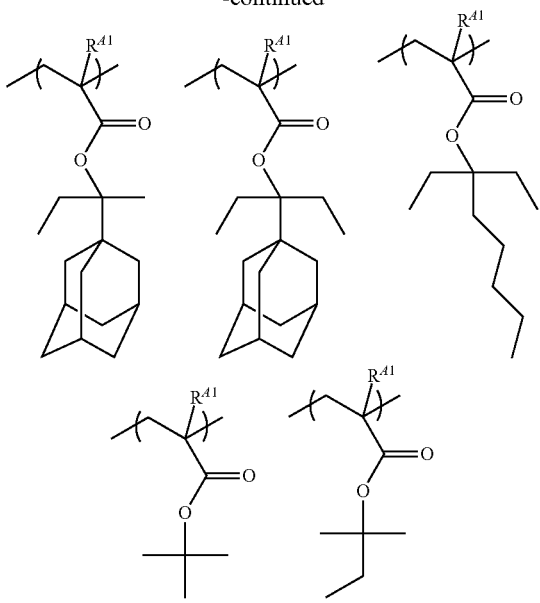

In the above formulae, $R^{A1}$ is as defined in the above formula (a-1).

Examples of the structural unit (1-2) include structural units represented by the following formulae, and the like.

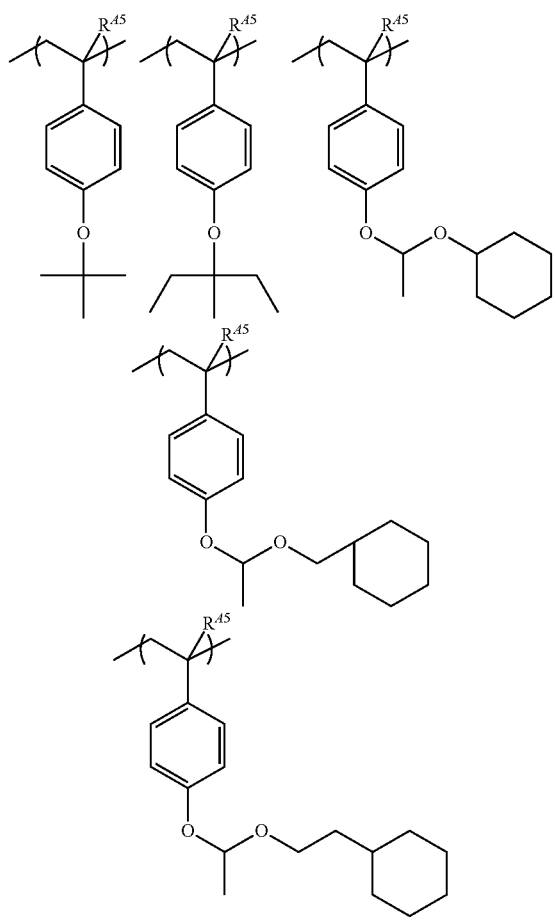

-continued

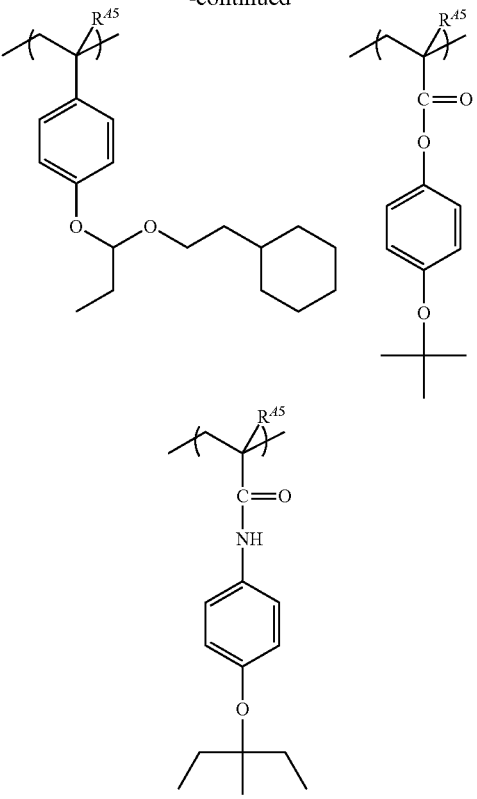

In the above formulae, $R^{A5}$ is as defined in the above formula (a-2).

As the structural unit (I), the structural units (I-1-a) to (I-1-d) are preferred, and a structural unit derived from 2-methyl-2-adamantyl (meth)acrylate, a structural unit derived from 2-i-propyl-2-adamantyl (meth)acrylate, a structural unit derived from 1-methyl-1-cyclopentyl (meth) acrylate, a structural unit derived from 1-ethyl-1-cyclohexyl (meth)acrylate, a structural unit derived from 1-i-propyl-1-cyclopentyl (meth)acrylate, a structural unit derived from 2-cyclohexylpropan-2-yl (meth)acrylate, and a structural unit derived from 2-(adamantan-1-yl)propan-2-yl (meth) acrylate are more preferred.

The lower limit of the proportion of the structural unit (I) with respect to the total structural units constituting the polymer (A) is preferably 10 mol %, more preferably 20 mol %, still more preferably 25 mol %, and particularly preferably 30 mol %. On the other hand, the upper limit of the proportion of the structural unit (III) with respect to the total structural units constituting the polymer (A) or the polymer (F) is preferably 80 mol %, more preferably 70 mol %, still more preferably 65 mol %, and particularly preferably 60 mol %. When the proportion of the structural unit (III) falls within the above range, a contrast in terms of dissolution in the developer solution between the patternwise exposed regions and the patternwise unexposed regions of the resist material film formed from the chemically amplified resist material can be sufficiently established, and consequently the resolution and the like may be improved.

Structural Unit (II)

The structural unit (II) includes a fluorine atom, but those corresponding to the structural unit (I) are excluded. The structural unit (ii) typically does not include a salt structure. Examples of the structural unit (II) include structural units represented by the following formulae (f-1) to (f-4), and the like.

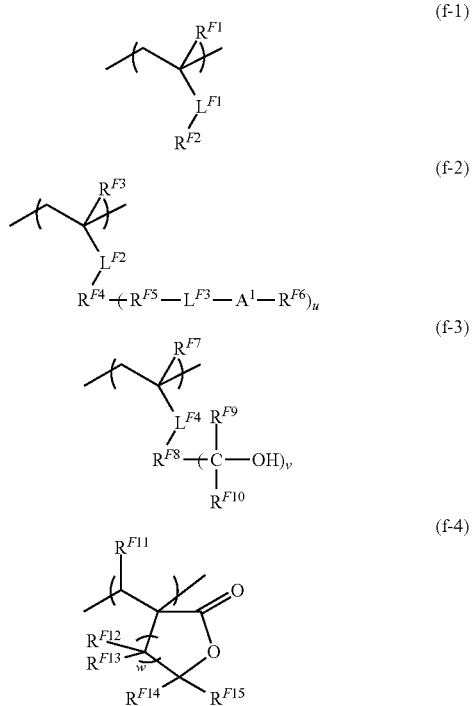

(f-1)
(f-2)
(f-3)
(f-4)

In the above formula (f-1), $R^{F1}$ represents a hydrogen atom, a fluorine atom, a methyl group or a trifluoromethyl group; $L^{F1}$ represents a single bond, an oxygen atom, a sulfur atom, —CO—O—, —SO$_2$—O—NH—, —CO—NH— or —O—CO—NH—; and $R^{F2}$ represents a monovalent fluorinated hydrocarbon group having 1 to 20 carbon atoms.

In the above formula (f-2), $R^{F3}$ represents a hydrogen atom, a fluorine atom, a methyl group or a trifluoromethyl group; $L^{F2}$ represents a single bond, an oxygen atom, a sulfur atom, —CO—O—, —SO$_2$—O—NH—, —CO—NH— or —O—CO—NH—; $R^{F4}$ represents a single bond, a hydrocarbon group having 1 to 20 carbon atoms and having a valency of (u+1), or a structure obtained by incorporating an oxygen atom, a sulfur atom, —NR$^{FF1}$—, a carbonyl group, —CO—O— or —CO—NH-into the end on the $R^{F5}$ side of the hydrocarbon group having 1 to 20 carbon atoms and having a valency of (u+1), wherein $R^{FF1}$ represents a hydrogen atom or a monovalent hydrocarbon group having 1 to 10 carbon atoms; $R^{F5}$ represents a single bond or a divalent organic group having 1 to 20 carbon atoms; $L^{F3}$ represents a single bond or a divalent fluorinated chain hydrocarbon group having 1 to 20 carbon atoms; $A^1$ represents an oxygen atom, —NR$^{FF2}$—, —CO—O—* or —SO$_2$—O—*, wherein $R^{FF2}$ represents a hydrogen atom or a monovalent hydrocarbon group having 1 to 10 carbon atoms, and * denotes a binding site to $R^{F6}$; $R^{F6}$ represents a hydrogen atom or a monovalent organic group having 1 to 30 carbon atoms; and u is an integer of 1 to 3, wherein in a case where u is 1, $R^{F4}$ may represent a single bond, and in a case where u is 2 or 3, a plurality of $R^{F5}$s may be identical or different, a plurality of $L^{F3}$s may be identical or different, a plurality of A's may be identical or different, and a plurality of $R^{F6}$s may be identical or different.

In the above formula (f-3), $R^{F7}$ represents a hydrogen atom, a fluorine atom, a methyl group, a trifluoromethyl group or a monovalent carbonyloxy hydrocarbon group having 2 to 20 carbon atoms; $L^{F4}$ represents a single bond, an oxygen atom, a sulfur atom, —CO—O—, —SO$_2$—O—NH—, —CO—NH— or —O—CO—NH—; $R^{F8}$ represents a single bond or a divalent organic group having 1 to 20 carbon atoms; $R^{F9}$ and $R^{F10}$ each independently represent an alkyl group having 1 to 10 carbon atoms or a fluorinated alkyl group having 1 to 10 carbon atoms, wherein either $R^{F9}$ or $R^{F10}$ represents the fluorinated alkyl group; and v is an integer of 1 to 3, wherein in a case where v is 2 or 3, a plurality of $R^{F9}$s may be identical or different, and a plurality of $R^{F10}$s may be identical or different.

In the above formula (f-4), $R^{F1}$ represents a hydrogen atom, a fluorine atom, a methyl group or a trifluoromethyl group; $R^{F12}$ and $R^{F13}$ each independently represent a hydrogen atom, a halogen atom, a hydroxy group or a monovalent organic group having 1 to 20 carbon atoms; w is an integer of 1 to 4, wherein in a case where w is no less than 2, a plurality of $R^{F12}$s may be identical or different, and a plurality of $R^{F13}$s may be identical or different, and at least two of one or more $R^{F12}$s and one or more $R^{F13}$s may taken together represent a ring structure having 3 to 20 ring atoms together with the carbon atom or the carbon chain to which the at least two of one or more $R^{F12}$s and one or more $R^{F13}$s bond; and $R^{F14}$ and $R^{F15}$ each independently represent a hydrogen atom or a monovalent organic group having 1 to 20 carbon atoms, wherein at least one of $R^{F4}$ and $R^{F15}$ represents a monovalent organic group having 1 to 20 carbon atoms and having at least one fluorine atom substituting for a hydrogen atom thereof, and wherein $R^{F14}$ and $R^{F15}$ may taken together represent a ring structure having 3 to 20 ring atoms together with the carbon atom to which $R^{F14}$ and $R^{F15}$ bond.

$R^{F1}$, $R^{F3}$ and $R^{F11}$ represent preferably a hydrogen atom or a methyl group, and more preferably a methyl group. $R^{F7}$ represents preferably a hydrogen atom, a methyl group or a monovalent carbonyloxy hydrocarbon group, more preferably a methyl group or an alkoxycarbonyl group, and still more preferably a methyl group or an ethoxycarbonyl group.

$L^{F1}$, $L^{F2}$ and $L^{F4}$ represent preferably a single bond, an oxygen atom or —CO—O—, and more preferably —CO—O—.

The monovalent fluorinated hydrocarbon group having 1 to 20 carbon atoms which is represented by $R^{F2}$ is exemplified by a group obtained from a monovalent hydrocarbon group having 1 to 20 carbon atoms by substituting a part or all of hydrogen atoms included therein with a fluorine atom. Examples of the monovalent hydrocarbon group having 1 to 20 carbon atoms include groups similar to those exemplified in connection with $R^{A2}$, $R^{A6}$, $R^{A7}$ and $R^{A8}$, and the like.

$R^{F2}$ represents preferably a fluorinated chain hydrocarbon group, more preferably a fluorinated alkyl group, and still more preferably a fluorinated methyl group or a fluorinated ethyl group.

The hydrocarbon group having 1 to 20 carbon atoms and having a valency of (u+1) which may be represented by $R^{F4}$ is exemplified by a group obtained from the monovalent hydrocarbon group having 1 to 20 carbon atoms, which is exemplified in connection with $R^{A2}$, $R^{A6}$, $R^{A7}$ and $R^{A8}$, by further eliminating u hydrogen atom(s), and the like.

$R^{FF1}$ represents preferably a hydrogen atom or an alkyl group having 1 to 10 carbon atoms, and more preferably a hydrogen atom, a methyl group or an ethyl group.

$R^{F4}$ represents preferably a single bond, a chain hydrocarbon group having 1 to 20 carbon atoms and having a valency of (u+1), or an aromatic hydrocarbon group having 6 to 20 carbon atoms and having a valency of (u+1), and more preferably a single bond, a chain hydrocarbon group having 1 to 10 carbon atoms and having a valency of (u+1) or an aromatic hydrocarbon group having 6 to 10 carbon atoms and having a valency of (u+1).

The divalent organic group having 1 to 20 carbon atoms which may be represented by $R^{F5}$ or $R^{F8}$ is exemplified by a divalent hydrocarbon group, a group obtained by incorporating a divalent hetero atom-containing group between two adjacent carbon atoms or at the end on the atomic bonding side of the divalent hydrocarbon group, a group obtained by substituting with a substituent, a part or all of hydrogen atoms included in the divalent hydrocarbon group or the group obtained by incorporating a divalent hetero atom-containing group between two adjacent carbon atoms or at the end on the atomic bonding side of the divalent hydrocarbon group, and the like.

Examples of the divalent hydrocarbon group having 1 to 20 carbon atoms include:

chain hydrocarbon groups, e.g., alkanediyl groups such as a methanediyl group, an ethanediyl group, a propanediyl group and a butanediyl group;

alkenediyl groups such as an ethenediyl group, a propenediyl group and a butenediyl group; and alkynediyl groups such as an ethynediyl group, a propynediyl group and a butynediyl group;

alicyclic hydrocarbon groups, e.g., monocyclic cycloalkanediyl groups such as a cyclopropanediyl group, a cyclobutanediyl group, a cyclopentanediyl group and a cyclohexanediyl group;

monocyclic cycloalkenediyl groups such as a cyclopropenediyl group and a cyclobutenediyl group;

polycyclic cycloalkanediyl groups such as a norbornanediyl group, an adamantanediyl group, a tricyclodecanediyl group and a tetracyclododecanediyl group; and polycyclic cycloalkenediyl groups such as a norbornenediyl group and a tricyclodecenediyl group;

aromatic hydrocarbon groups, e.g., arenediyl groups such as a benzenediyl group, a toluenediyl group, a xylenediyl group and a naphthalenediyl group;

arenediyl(cyclo)alkanediyl groups such as a benzenediylmethanediyl group and a naphthalenediylcyclohexanediyl group; and the like.

The hetero atom-containing group as referred to means a group that includes a hetero atom having a valency of no less than 2 in a structure thereof. The hetero atom-containing group may include one, or two or more hetero atoms. The term "hetero atom" as referred to means an atom other than a hydrogen atom and a carbon atom. The hetero atom-containing group may have only the hetero atom.

The hetero atom having a valency of no less than 2 which is included in the hetero atom-containing group is not particularly limited as long as the hetero atom has a valency of no less than 2, and examples thereof include an oxygen atom, a nitrogen atom, a sulfur atom, a silicon atom, a phosphorus atom, a boron atom, and the like.

Examples of the hetero atom-containing group include —O—, —S—, —NR$^{HE}$—, —PR$^{HE}$—, —SO—, —SO$_2$—, —SO$_2$O—, —OPO(OR$^{HE}$)O—, —PO$_2$—, —PO$_2$O—, —CO—, —COO—, —COS—, —CONR$^{HE}$—, —OCOO—, —OCOS—, —OCONR$^{HE}$—, —SCON-R$^{HE}$—, —SCSNR$^{HE}$—, —SCSS— group, and the like, wherein R$^{HE}$ represents a hydrogen atom or a monovalent hydrocarbon group having 1 to 20 carbon atoms.

Examples of the substituent include halogen atoms such as a fluorine atom, a chlorine atom, a bromine atom and an iodine atom, a hydroxy group, a carboxy group, a nitro group, a cyano group, and the like.

$R^{F5}$ and $R^{F8}$ represent preferably a single bond, a divalent hydrocarbon group, or a group obtained by incorporating an oxygen atom between two adjacent carbon atoms of the divalent hydrocarbon group having 1 to 20 carbon atoms, more preferably a single bond, a divalent chain hydrocarbon group having 1 to 20 carbon atoms, a group obtained by incorporating an oxygen atom between two adjacent carbon atoms of the divalent chain hydrocarbon group, or a divalent aromatic hydrocarbon group having 1 to 20 carbon atoms, and still more preferably a single bond, an alkanediyl group, an alkanediyloxyalkanediyl group or an arenediyl group.

The divalent fluorinated chain hydrocarbon group having 1 to 20 carbon atoms which may be represented by $L^{F3}$ is exemplified by a divalent fluorinated chain hydrocarbon obtained by substituting with a fluorine atom, a part or all of hydrogen atoms included in the divalent chain hydrocarbon group exemplified in connection with $R^{F5}$ and $R^{F8}$, and the like.

$L^{F3}$ represents preferably a single bond or a divalent fluorinated chain hydrocarbon group having 1 to 10 carbon atoms, and more preferably a single bond or a fluorinated alkanediyl group having 1 to 10 carbon atoms.

$A^1$ preferably represents an oxygen atom or —CO—O—.

$R^{FF2}$ represents a hydrogen atom or an alkyl group having 1 to 10 carbon atoms, and more preferably a hydrogen atom, a methyl group or an ethyl group.

The monovalent organic group having 1 to 20 carbon atoms which may be represented by $R^{F6}$, $R^{F12}$, $R^{F13}$, $R^{F14}$ or $R^{F15}$ is exemplified by a monovalent hydrocarbon group, a group obtained by incorporating a divalent hetero atom-containing group between two adjacent carbon atoms or at the end on the atomic bonding side of the monovalent hydrocarbon group, a group obtained by substituting with a substituent, a part or all of hydrogen atoms included in the monovalent hydrocarbon group or the group obtained by incorporating a divalent hetero atom-containing group between two adjacent carbon atoms or at the end on the atomic bonding side of the monovalent hydrocarbon group, and the like.

Examples of the monovalent hydrocarbon group include monovalent hydrocarbon groups similar to those exemplified in connection with $R^{42}$, $R^{46}$, $R^{47}$ and $R^{48}$. In addition, examples of the hetero atom-containing group and the substituent include groups similar to those exemplified in connection with $R^{F5}$ and $R^{F8}$, and the like.

$R^{F6}$ represents preferably a hydrogen atom or a monovalent chain hydrocarbon group having 1 to 30 carbon atoms, more preferably a hydrogen atom or an alkyl group having 1 to 30 carbon atoms, and still more preferably a hydrogen atom or an alkyl group having 1 to 10 carbon atoms. Wherein, in the case where $L^{F3}$ represents the single bond, $R^{F6}$ preferably includes a fluorine atom.

$R^{F12}$ and $R^{F13}$ represent preferably a hydrogen atom or a monovalent hydrocarbon group having 1 to 12 carbon atoms, more preferably a monovalent hydrocarbon group having 1 to 12 carbon atoms, and still more preferably a phenyl group, a cycloalkyl group, or a hydroxy group-substituted fluorine atom-containing alkyl group.

$R^{F14}$ and $R^{F15}$ represent preferably a hydrogen atom, a monovalent hydrocarbon group having 1 to 12 carbon atoms or a monovalent hydroxy substituted fluorinated hydrocarbon group having 3 to 12 carbon atoms, more preferably a hydrogen atom, an alkyl group having 1 to 12 carbon atoms or a hydroxyfluorinated alkyl group having 3 to 12 carbon atoms, and still more preferably a hydrogen atom, a methyl group, an ethyl group or a hydroxydi(trifluoromethyl)ethyl group.

$R^{F9}$ and $R^{F10}$ represent preferably a methyl group, an ethyl group, a propyl group, a fluorinated methyl group, a fluorinated ethyl group or a fluorinated propyl group, more preferably a fluorinated methyl group or a fluorinated ethyl group, still more preferably a fluorinated methyl group, and particularly preferably a trifluoromethyl group.

In the formula (f-2), u is preferably 1 or 2, and more preferably 1. In the formula (f-3), v is preferably 1 or 2, and more preferably 1. In the formula (f-4), w is preferably 1 or 2, and more preferably 1.

The structural unit (II) is preferably a structural unit represented by any one of the following formulae.

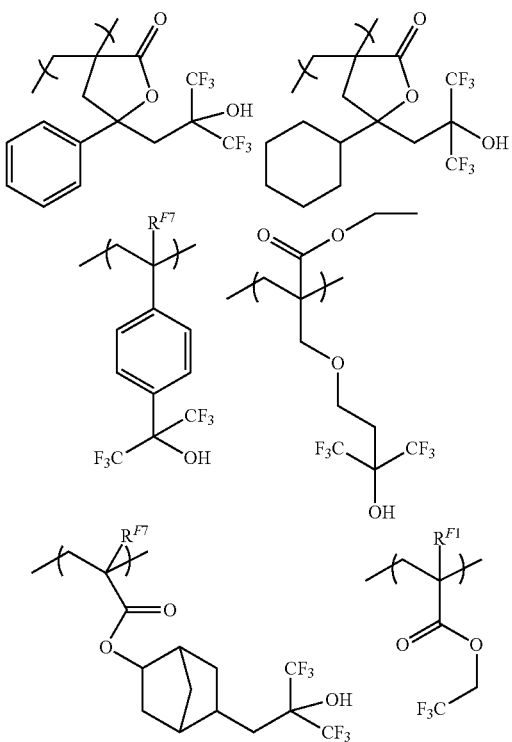

In the above formulae, $R^{F1}$ is as defined in the above formula (f-1); and $R^{F7}$ is as defined in the above formula (f-3).

In the case where the polymer (A) has the structural unit (II), the lower limit of the proportion of the structural unit (II) with respect to the total structural units constituting the polymer (A) is preferably 3 mol %, more preferably 5 mol %, and still more preferably 10 mol %. On the other hand, the upper limit of the proportion of the structural unit (II) with respect to the total structural units constituting the polymer (A) is preferably 40 mol %, more preferably 35 mol %, and still more preferably 30 mol %. When the proportion of the structural unit (II) with respect to the total structural units constituting the polymer (A) falls within the above range, the sensitivity in the case of the use of EUV and the like as patterning exposure light can be more improved. On the other hand, when the proportion of the structural unit (II) with respect to the total structural units constituting the polymer (A) is greater than the upper limit, the rectangularity of the cross-sectional shape of the resist pattern may be deteriorated.

In the case where the polymer component (1) includes the polymer (B), and the polymer (B) has the structural unit (II), the lower limit of the proportion of the structural unit (II) with respect to the total structural units constituting the polymer (B) is preferably 3 mol %, more preferably 5 mol %, and still more preferably 10 mol %. On the other hand, the upper limit of the proportion of the structural unit (II) with respect to the total structural units constituting the polymer (B) is preferably 40 mol %, more preferably 35 mol %, and still more preferably 30 mol %. When the proportion of the structural unit (II) with respect to the total structural units constituting the polymer (B) falls within the above range, the sensitivity in the case of the use of EUV and the like as patterning exposure light can be more improved. On the other hand, when the proportion of the structural unit (II) with respect to the total structural units constituting the polymer (B) is greater than the upper limit, the rectangularity of the cross-sectional shape of the resist pattern may be deteriorated.

Structural Unit (III)

The structural unit (III) includes a phenolic hydroxyl group, wherein those corresponding to the structural unit (I) and the structural unit (II) are excluded. When the polymer (A) or the polymer (B) has the structural unit (III), the sensitivity can be more improved in the case of the irradiation with a KrF excimer laser beam, EUV (extreme ultraviolet ray), an electron beam or the like in the patternwise exposure step described later.

A part or all of hydrogen atoms included in an aromatic ring that includes the phenolic hydroxyl group may be substituted with a substituent. Examples of the substituent include groups similar to those exemplified in connection with $R^{F5}$ and $R^{F8}$, and the like.

Examples of the structural unit (III) include structural units represented by the following formulae (h-1) to (h-6) (hereinafter, may be also referred to as "structural units (III-1) to (III-6)"), and the like.

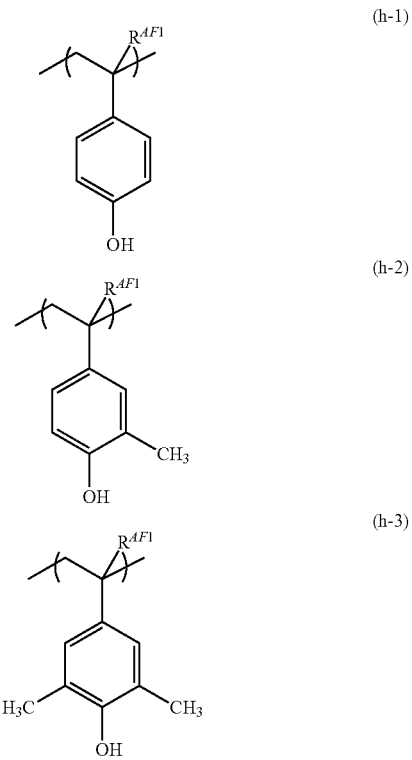

-continued

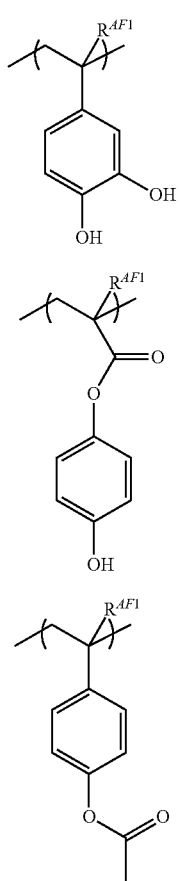

(h-4)

(h-5)

(h-6)

In the above formulae (h-1) to (h-6), $R^{AF1}$ represents a hydrogen atom or a methyl group.

$R^{AF1}$ represents preferably a hydrogen atom.

The structural unit (III) is preferably structural unit (III-1) or (III-2), and more preferably (III-1).

In the case where the polymer (A) has the structural unit (III), the lower limit of the proportion of the structural unit (III) with respect to the total structural units constituting the polymer (A) is preferably 1 mol %, more preferably 30 mol %, and still more preferably 50 mol %. On the other hand, the upper limit of the proportion of the structural unit (III) with respect to the total structural units constituting the polymer (A) is preferably 90 mol %, more preferably 80 mol %, and still more preferably 75 mol %. When the proportion of the structural unit (III) falls within the above range, the sensitivity of the chemically amplified resist material can be more improved.

In the case where the polymer component (1) includes the polymer (B), and the polymer (B) has the structural unit (III), the lower limit of the proportion of the structural unit (III) with respect to the total structural units constituting the polymer (B) is preferably 1 mol %, more preferably 30 mol %, and still more preferably 50 mol %. On the other hand, the upper limit of the proportion of the structural unit (III) with respect to the total structural units constituting the polymer (B) is preferably 90 mol %, more preferably 80 mol %, and still more preferably 75 mol %. When the proportion of the structural unit (III) falls within the above range, the sensitivity of the chemically amplified resist material can be more improved.

It is to be noted that the structural unit (III) may also include a structure that can be formed by a method including: polymerizing a monomer obtained from a compound having an aromatic ring having a phenolic hydroxyl group by substitution of the hydrogen atom of an —OH group with an acetyl group or the like; and thereafter subjecting the obtained polymer to a hydrolysis reaction in the presence of an amine, or the like.

Structural Unit (IV)

The structural unit (IV) includes a lactone structure, a cyclic carbonate structure, a sultone structure or a combination thereof, wherein those corresponding to the structural units (I) to (III) are excluded. When the structural unit (IV) is further included, the polymer (A) and the polymer (B) can have more appropriately adjusted solubility in the developer solution, and as a result, the lithography performances of the chemically amplified resist material can be further improved. Also, the adhesiveness of the resist material film formed from the chemically amplified resist material to the substrate can be improved. The lactone structure as referred to herein means a structure which has one ring including a group represented by —O—C(O)— (lactone ring). Moreover, the cyclic carbonate structure as referred to means a structure which has one ring including a group represented by —O—C(O)—O— (cyclic carbonate ring). The sultone structure as referred to means a structure which has one ring including a group represented by —O—S(O)$_2$— (sultone ring). Examples of the structural unit (IV) include structural units represented by the following formulae, and the like.

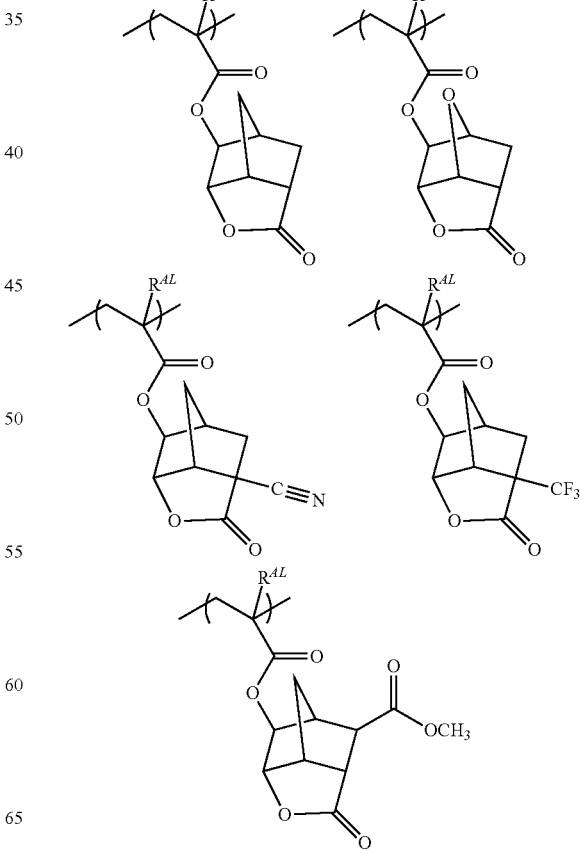

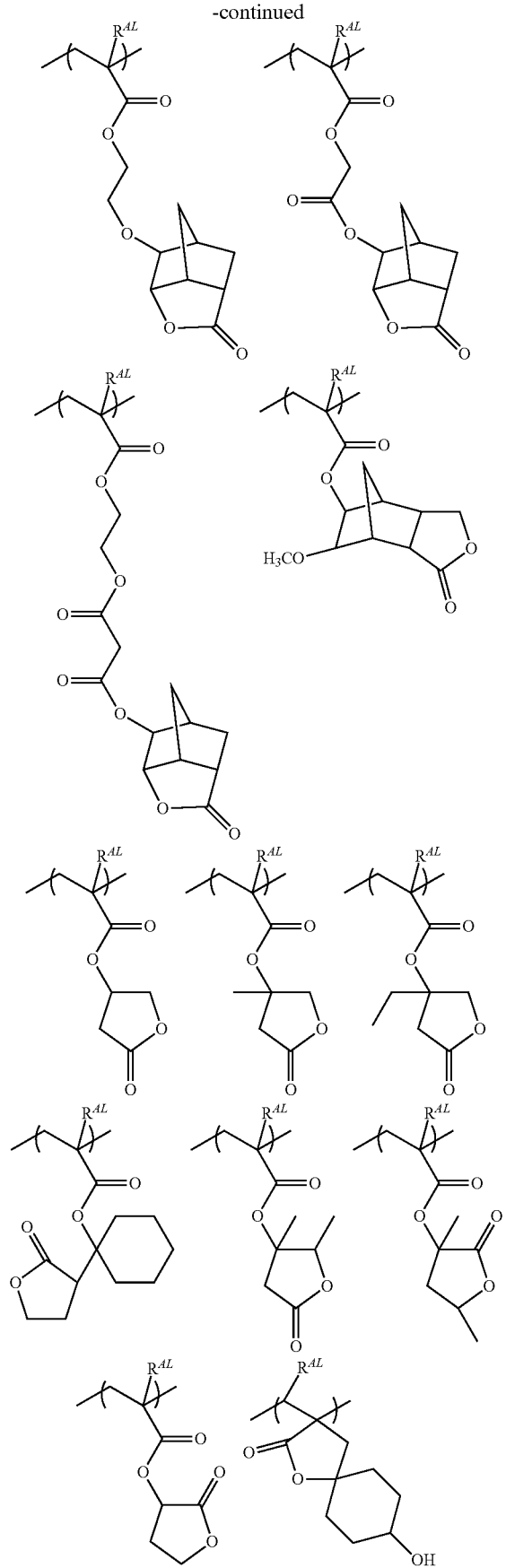
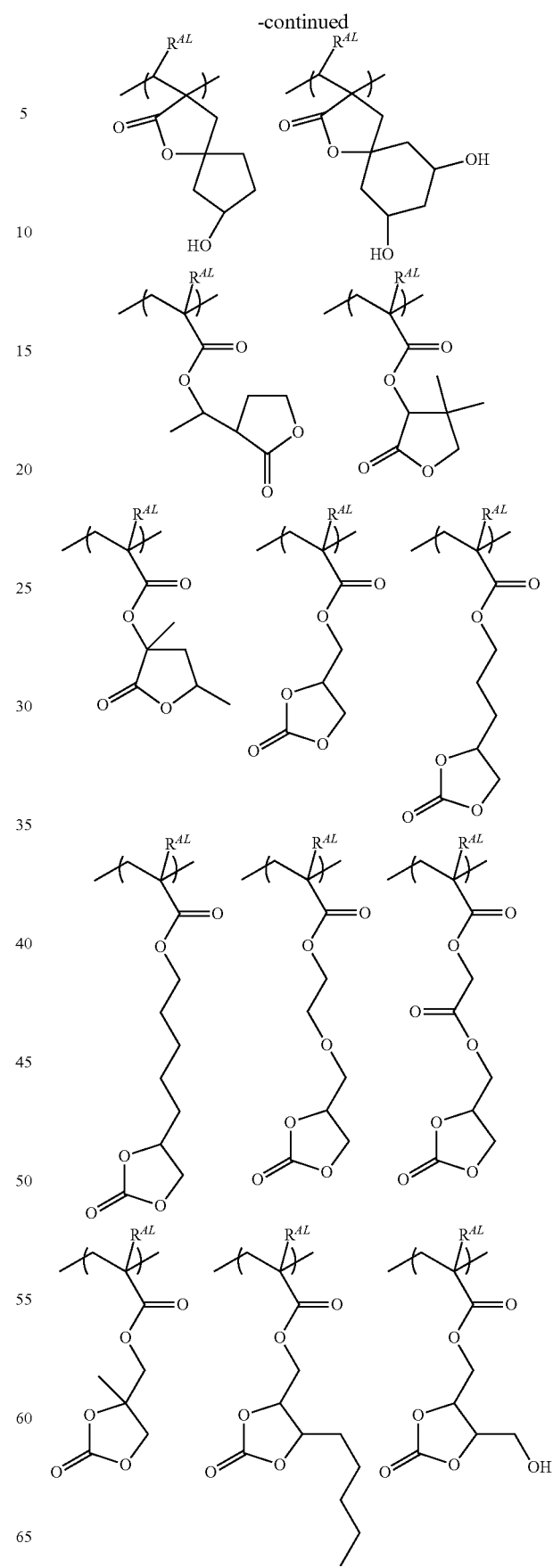

-continued
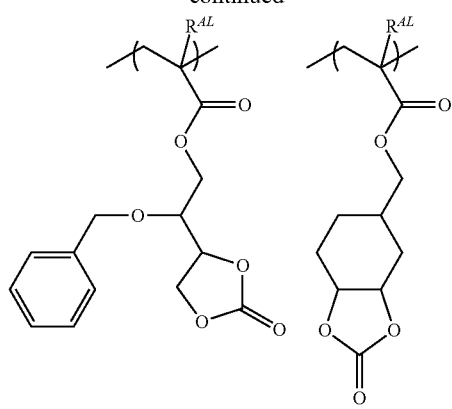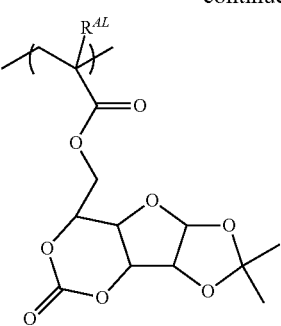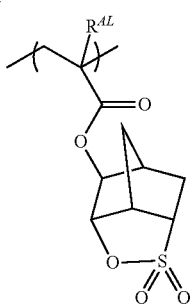
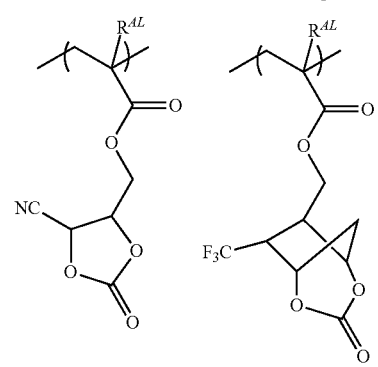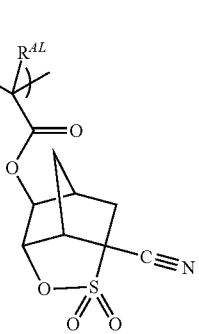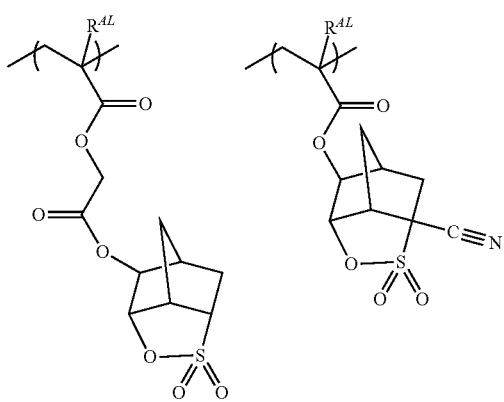
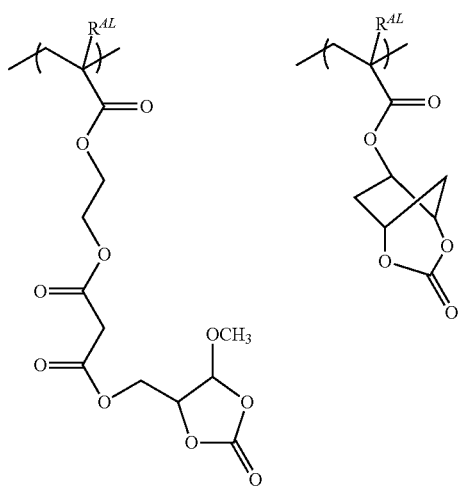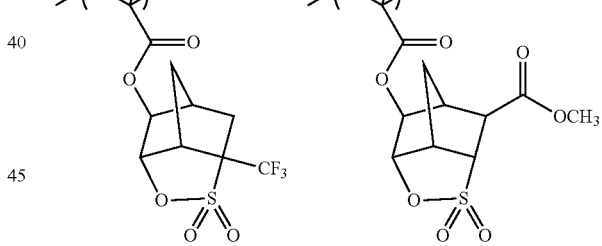
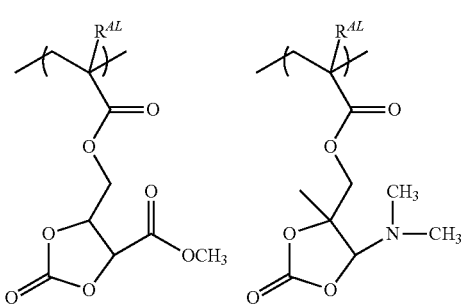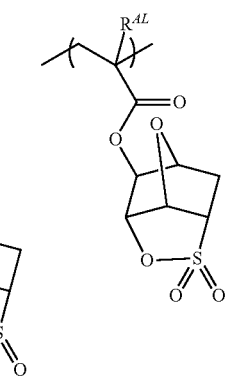

-continued

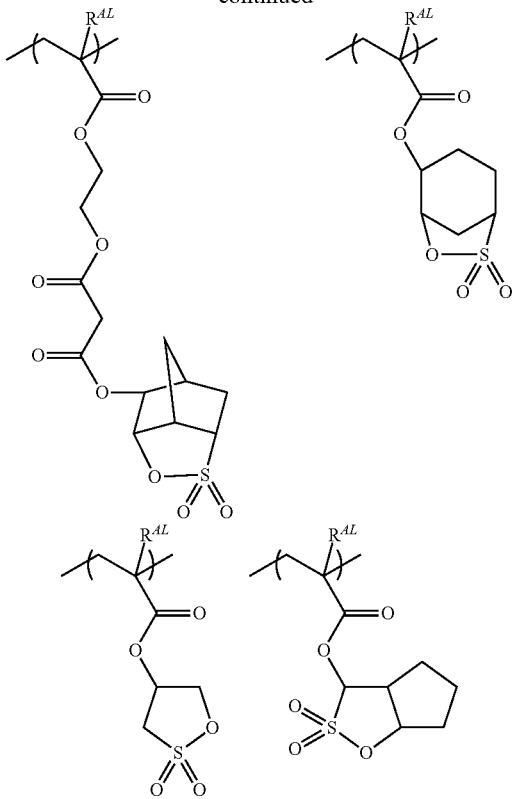

In the above formulae, $R^{AL}$ represents a hydrogen atom, a fluorine atom, a methyl group, or a trifluoromethyl group.

In light of the copolymerizability of a monomer that gives the structural unit (IV), $R^{AL}$ represents preferably a hydrogen atom or a methyl group, and more preferably a methyl group.

Of these, as the structural unit (IV), a structural unit that includes a norbornanelactone structure, a structural unit that includes an oxanorbornanelactone structure, a structural unit that includes a γ-butyrolactone structure, a structural unit that includes an ethylene carbonate structure, and a structural unit that includes a norbornanesultone structure are preferred, and a structural unit derived from norbornanelacton-yl (meth)acrylate, a structural unit derived from oxanorbornanelacton-yl (meth)acrylate, a structural unit derived from cyano-substituted norbornanelacton-yl (meth)acrylate, a structural unit derived from norbornanelacton-yloxycarbonylmethyl (meth)acrylate, a structural unit derived from butyrolacton-3-yl (meth)acrylate, a structural unit derived from butyrolacton-4-yl (meth)acrylate, a structural unit derived from 3,5-dimethylbutyrolacton-3-yl (meth)acrylate, a structural unit derived from 4,5-dimethylbutyrolacton-4-yl (meth)acrylate, a structural unit derived from 1-(butyrolacton-3-yl)cyclohexan-1-yl (meth)acrylate, a structural unit derived from ethylene carbonate-ylmethyl (meth)acrylate, a structural unit derived from cyclohexene carbonate-ylmethyl (meth)acrylate, a structural unit derived from norbornmanesultone-yl (meth)acrylate, and a structural unit derived from norbornanesultone-yloxycarbonylmethyl (meth)acrylate are more preferred.

In the case where the polymer (A) has the structural unit (IV), the lower limit of the proportion of the structural unit (IV) with respect to the total structural units constituting the polymer (A) is preferably 1 mol %, more preferably 10 mol %, still more preferably 20 mol %, and particularly preferably 25 mol %. On the other hand, the upper limit of the proportion of the structural unit (IV) with respect to the total structural units constituting the polymer (A) is preferably 70 mol %, more preferably 65 mol %, still more preferably 60 mol %, and particularly preferably 55 mol %. When the proportion of of the structural unit (IV) with respect to the total structural units constituting the polymer (A) falls within the above range, the adhesiveness of the resist material film formed from the chemically amplified resist material to the substrate can be further improved.

In the case where the polymer component (1) includes the polymer (B), and the polymer (B) has the structural unit (IV), the lower limit of the proportion of the structural unit (IV) with respect to the total structural units constituting the polymer (B) is preferably 1 mol %, more preferably 10 mol %, still more preferably 20 mol %, and particularly preferably 25 mol %. On the other hand, the upper limit of the proportion of the structural unit (IV) with respect to the total structural units constituting the polymer (B) is preferably 70 mol %, more preferably 65 mol %, still more preferably 60 mol %, and particularly preferably 55 mol %. When the proportion of the structural unit (IV) with respect to the total structural units constituting the polymer (B) falls within the above range, the adhesiveness of the resist material film formed from the chemically amplified resist material to the substrate can be further improved.

Other Structural Unit

The polymer (A) and the polymer (B) may have other structural unit than the structural units (I) to (IV). The other structural unit is exemplified by: a structural unit that includes a structural unit that includes a polar group, a structural unit that includes a nonlabile hydrocarbon group, and the like. examples of the polar group include an alcoholic hydroxyl group, a carboxy group, a cyano group, a nitro group, a sulfonamide group, and the like. Examples of the structural unit that includes a nonlabile hydrocarbon group include a linear alkyl group, and the like. The upper limit of the proportion of the other structural unit with respect to the total structural units constituting the polymer (A) is preferably 20 mol %, and more preferably 10 mol %. The upper limit of the proportion of the other structural unit with respect to the total structural units constituting the polymer (B) is preferably 20 mol %, and more preferably 10 mol %.

The lower limit of the total content of the polymer (A) and the polymer (B) in the total solid content of the chemically amplified resist material is preferably 70% by mass, more preferably 75% by mass, and still more preferably 80% by mass. The term "total solid content" as referred to means the component other than the solvent of the chemically amplified resist material.

The polystyrene equivalent weight average molecular weight (Mw) as determined by gel permeation chromatography (GPC) of the polymer (A) is not particularly limited, and the lower limit thereof is preferably 1,000, more preferably 2,000, still more preferably 3,000, and particularly preferably 5,000. On the other hand, the upper limit of the Mw of the polymer (A) is preferably 50,000, more preferably 30,000, still more preferably 20,000, and particularly preferably 15,000. When the Mw of the polymer (A) falls within the above range, the application property and development defects-inhibiting property of the chemically amplified resist material may be improved. When the Mw of the polymer (A) is less than the lower limit, the resist material film exhibiting sufficient heat resistance may not be obtained. To the contrary, when the Mw of the polymer (A)

is greater than the upper limit, the developability of the resist material film may be deteriorated.

The lower limit of the ratio (Mw/Mn) of the Mw to the polystyrene equivalent number average molecular weight (Mn) as determined by GPC of the polymer (A) is typically 1. On the other hand, the upper limit of the ratio (Mw/Mn) is typically 5, preferably 3, and still more preferably 2.

The polystyrene equivalent weight average molecular weight (Mw) as determined by gel permeation chromatography (GPC) of the polymer (B) is not particularly limited, and the lower limit thereof is preferably 1,000, more preferably 2,000, still more preferably 2,500, and particularly preferably 3,000. On the other hand, the upper limit of the Mw of the polymer (B) is preferably 50,000, more preferably 30,000, still more preferably 20,000, and particularly preferably 15,000. When the Mw of the polymer (B) falls within the above range, the application property and development defects-inhibiting property of the chemically amplified resist material may be improved. When the Mw of the polymer (B) is less than the lower limit, the resist material film exhibiting sufficient heat resistance may not be obtained. To the contrary, when the Mw of the polymer (B) is greater than the upper limit, the developability of the resist material film may be deteriorated.

The lower limit of the ratio (Mw/Mn) of the Mw to the polystyrene equivalent number average molecular weight (Mn) as determined by GPC of the polymer (B) is preferably 1. On the other hand, the upper limit of the ratio (Mw/Mn) is preferably 5, more preferably 3, and still more preferably 2.

Herein, the Mw and the Mn of the polymer are determined using gel permeation chromatography (GPC) under the following conditions.

GPC columns: G2000 HXL×2, G3000 HXL×1 and G4000 HXL×1 (each available from Tosoh Corporation)
 column temperature: 40° C.
 elution solvent: tetrahydrofuran
 flow rate: 1.0 mL/min
 sample concentration: 1.0% by mass
 amount of injected sample: 100 μL
 detector: differential refractometer
 standard substance: mono-dispersed polystyrene The polymer (A) and the polymer (B) may include a low-molecular weight component having a molecular weight of no greater than 1,000. The upper limit of the content of the low-molecular weight component in the polymer (A) is preferably 1.0% by mass, more preferably 0.5% by mass, and still more preferably 0.3% by mass. The lower limit of the content of the low-molecular weight component in the polymer (A) is 0.01% by mass, for example. The upper limit of the content of the low-molecular weight component in the polymer (B) is preferably 1.0% by mass, more preferably 0.5% by mass, and still more preferably 0.3% by mass. The lower limit of the content of the low-molecular weight component in the polymer (B) is 0.01% by mass, for example. When the content of the low-molecular weight component in the polymer (A) or the polymer (B) falls within the above range, the lithography performances of the chemically amplified resist material can be more improved.

Herein, the content of the low molecular weight component in the polymer is determined by high performance liquid chromatography (HPLC) under the following conditions.

column: "Inertsil ODA-25 μm column" (4.6 mmφ×250 mm) available from GL Sciences, Inc.
 eluent: acrylonitrile/0.1% by mass aqueous phosphoric acid solution
 flow rate: 1.0 mL/min
 sample concentration: 1.0% by mass
 amount of injected sample: 100 μL
 detector: differential refractometer The lower limit of the percentage content of fluorine atom in the polymer (A) and the polymer (B) is preferably 1% by mass, more preferably 2% by mass, still more preferably 4% by mass, and particularly preferably 7% by mass. On the other hand, the upper limit of the percentage content of fluorine atom in the polymer (A) and the polymer (B) is preferably 60% by mass, more preferably 40% by mass, and still more preferably 30% by mass. In this regard, the percentage content of fluorine atom (% by mass) of the polymer can be calculated based on the polymer structure determined by $^{13}C$-NMR spectroscopy.

The polymer component (1) preferably contains at least two polymers each having a different percentage content of fluorine atom. The polymer component (1) is exemplified by: a polymer component that contains the polymer (A) and the polymer (B) in which the polymer (B) has a greater percentage content of fluorine atom than that of the polymer (A); a polymer component that contains the polymer (A) and the polymer (B) in which the polymer (A) has a greater percentage content of fluorine atom than that of the polymer (B); a polymer component that contains at least two polymers (A) each having a different percentage content of fluorine atom; a polymer component that contains at least two polymers (B) each having a different percentage content of fluorine atom; and the like. When the polymer component (1) thus contains the at least two polymers each having a different percentage content of fluorine atom, a polymer having a higher percentage content of fluorine atom is allowed to be localized in the surface region of the resist material film, and can function as a water repellent polymer additive. As a result, elution of the generative component (2) and the like from the resist material film can be inhibited, and the dynamic contact angle of the surface of the formed resist material film can be more desirable, thereby enabling superior water draining properties to be achieved. Thus, an exposure by high speed scanning is enabled when liquid immersion lithography is carried out as described later.

Synthesis Method of Polymer (A) and Polymer (B)

The polymer (A) and the polymer (B) may be produced by, for example, polymerizing monomer(s) each corresponding to the predetermined structural unit in an appropriate polymerization reaction solvent using a polymerization initiator such as a radical polymerization initiator. Regarding specific synthesis methods, for example, a procedure that involves adding a solution containing a monomer and a radical polymerization initiator dropwise to a solution containing a polymerization reaction solvent or a monomer to permit a polymerization reaction; a procedure that involves separately adding a solution containing a monomer and a solution containing a radical polymerization initiator dropwise to a solution containing a polymerization reaction solvent or a monomer to permit a polymerization reaction; a procedure that involves separately adding a plurality of kinds of solutions containing each monomer, and a solution containing a radical polymerization initiator dropwise to a solution containing a polymerization reaction solvent or a monomer to permit a polymerization reaction; and the like may be referred to.

Examples of the radical polymerization initiator include: azo radical initiators such as azobisisobutyronitrile (AIBN), 2,2'-azobis(4-methoxy-2,4-dimethylvaleronitrile), 2,2'-azobis(2-cyclopropylpropionitrile), 2,2'-azobis(2,4-dimethylvaleronitrile) and dimethyl 2,2'-azobisisobutyrate; peroxide radical initiators such as benzoyl peroxide, t-butyl hydroperoxide and cumene hydroperoxide; and the like. Of these, the radical polymerization initiator is preferably AIBN or dimethyl 2,2'-azobisisobutyrate, and more preferably AIBN. These radical initiators may be used either alone of one type, or in combination of two or more types thereof.

Examples of the solvent which may be used in the polymerization include solvents similar to those which may be contained in the chemically amplified resist material and will be described later.

The lower limit of the reaction temperature in the polymerization is preferably 40° C., and more preferably 50° C. On the other hand, the upper limit of the reaction temperature is preferably 150° C., and more preferably 120° C. The lower limit of the reaction time period in the polymerization is preferably 1 hour. On the other hand, the upper limit of the reaction time period is preferably 48 hrs, and more preferably 24 hrs.

The polymer (A) and the polymer (B) are preferably recovered according to a reprecipitation technique. More specifically, after the completion of the reaction, the intended copolymer is recovered in the form of a powder through charging the reaction mixture into a reprecipitation solvent. Alcohols, alkanes and the like may be used as the reprecipitation solvent, either alone of one type or in combination of two or more types thereof. In addition to the reprecipitation technique, a liquid separating operation, a column operation, an ultrafiltration operation or the like enables the polymer to be recovered through eliminating the low molecular weight component such as monomers and oligomers.

(2) Component that is Capable of Generating Radiation-Sensitive Sensitizer and Acid Upon Exposure The generative component (2) generates a radiation-sensitive sensitizer and an acid upon an exposure (irradiation with a radioactive ray). Among three components of (a) a radiation-sensitive acid-and-sensitizer generating agent, (b) a radiation-sensitive sensitizer generating agent, and (c) a radiation-sensitive acid generating agent, the component (2) contains the component (a), the components (a) and (b), the components (a) and (c), the components (b) and (c), or all of the components (a) to (c).

The radiation-sensitive acid-and-sensitizer generating agent (a) or the radiation-sensitive acid generating agent (c) includes the compound (C1) having the cation (I) and the anion (I), and the compound (C2) having the cation (II) and the anion (II). The anion (II) is different from the anion (I). More specifically, the radiation-sensitive acid-and-sensitizer generating agent (a) or the radiation-sensitive acid generating agent (c) has the cation (I) and the cation (II) as a cation, and has the anion (I) and the anion (II) as an anion. The cation (I) and the cation (II) are an onium cation, and the each energy released upon reduction thereof to a radical is less than 5.0 eV. The radiation-sensitive acid-and-sensitizer generating agent (a) or the radiation-sensitive acid generating agent (c) may include either one type alone or two or more types of the compound (C1) and the compound (C2), respectively.

Of the compound (C1) and the compound (C2), one compound that is capable of generating an acid having a smaller logarithmic value of a reciprocal number of the acid dissociation constant (pKa) functions as an acid generating compound that is capable making the polymer component (1) soluble or insoluble in a developer solution. Also, another compound that is capable of generating an acid having a greater pKa functions as an acid diffusion control agent.

Cation

The cation (I) and the cation (II) are each an onium cation, and each energy released upon reduction thereof to a radical is less than 5.0 eV.

In the chemically amplified resist material, the radiation-sensitive acid-and-sensitizer generating agent (a) or the radiation-sensitive acid generating agent (c) includes the compound (C1) and the compound (C2), and each of the energy released upon reduction of the cation (I) and the energy released upon reduction of the cation (II) to a radical is less than 5.0 eV, whereby superior lithography performances can be achieved while favorable sensitivity is maintained in a case where a radioactive ray having a wavelength of no greater than 250 nm, such as EUV, is used as the patterning exposure light. Although the reason for achieving these effects by the chemically amplified resist material owing to having the above-described constitution is not clear, the reason may be be inferred as follows, for example. It is considered that when the energy released upon reduction to a radical, by the cations which may be included in the radiation-sensitive acid-and-sensitizer generating agent (a) or the radiation-sensitive acid generating agent (c) is less than the above specified value, photodegradability of the compound that functions as the acid diffusion control agent can be controlled at an adequately low level, and thus the degradation in pattern light-unexposed regions can be inhibited, thereby consequently leading to an improvement of lithography performances while favorable sensitivity is maintained.

The upper limit of the energy released upon the reduction of the cation (I) and the cation (II) to a radical is preferably 4.9 eV, and more preferably 4.8 eV. The lower limit of the released energy is preferably 4.0 eV, and more preferably 4.2 eV.

The lower limit of each reduction potential of the cation (I) and the cation (II) is preferably −3.0 V, more preferably −2.5 V, and still more preferably −2.0 V. On the other hand, the upper limit of each reduction potential is preferably −0.8 V, and more preferably −0.9 V.

The lower limit of the total percentage content of the cation (I) and the cation (II) with respect to the total onium cations in the chemically amplified resist material is preferably 80 mol %, more preferably 85 mol %, and still more preferably 90 mol %. When the total percentage content of the cation (I) and the cation (II) falls within the above range, the sensitivity and lithography performances of the chemically amplified resist material can be more improved.

The cation (I) and the cation (II) are exemplified by a monovalent onium cation represented by $X^+$. Examples of the monovalent onium cation represented by $X^+$ include cations represented by the following formulae (X-1) and (X-2) (hereinafter, may be also referred to as "cation (X-1)" and "cation (X-2)").

$X^+$ is preferably a triphenylsulfonium cation.

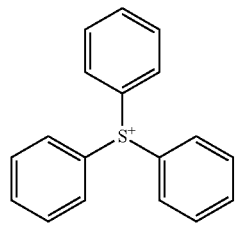

(X-1)

-continued

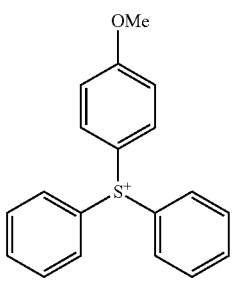

(X-2)

Anion

The anion (I) and the anion (II) are different from one another.

The upper limit of the pKa of the acid generated from at least one of the compound (C1) and the compound (C2) is preferably 0, and more preferably −0.5. Whereas, the lower limit of the pKa of the acid generated from the at least one is preferably −7, and more preferably −5. The upper limit of the pKa of the acid generated from another compound is preferably 11.0, and more preferably 10.5. Whereas, the lower limit of the pKa of the acid generated from the another compound is preferably 0, more preferably 1, and still more preferably 2. When the pKa of the acid falls within the above range, further superior lithography performances can be achieved. It is to be noted that the pKa is a value determined according to ACD/ChemSketch (ACD/Labs 8.00 Release Product Version: 8.08).

Examples of the anion (I) and the anion (II) include a sulfonic acid anion, a carboxylic acid anion, a bis(alkylsulfonyl)amide anion, a tris(alkylsulfonyl)methide anion, and the like.

Of the anion (I) and the anion (II), as the anion that is capable of generating an acid having a smaller logarithmic value of a reciprocal number of the dissociation constant (pKa) and that functions as the anion of the acid generating compound, acid anions represented by the following general formulae (XX), (XXI) and (XXII) are preferred, and an acid anion represented by the following general formula (XX) is more preferred.

  (XX)

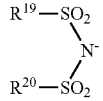  (XXI)

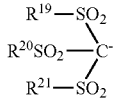  (XXII)

In the above general formulae (XX), (XXI) and (XXII), $R^{18}$ to $R^{21}$ each independently represent an organic group. The organic group is exemplified by an alkyl group, an aryl group, a group obtained by linking a plurality of alkyl groups and/or aryl groups, and the like. The organic group is preferably an alkyl group substituted with a fluorine atom or a fluoroalkyl group in 1-position, or a phenyl group substituted with a fluorine atom or a fluoroalkyl group. When the organic group includes the fluorine atom or the fluoroalkyl group, the acidity of the acid generated upon the exposure tends to increase, leading to an improvement of the sensitivity. However, it is preferred that the organic group does not include the fluorine atom as the substituent at an end thereof.

Of the compound (C1) and the compound (C2), as the compound that is capable of generating an acid having a smaller logarithmic value of a reciprocal number of the acid dissociation constant (pKa), and thus functions as the acid generating compound is preferably represented by the following formula (1). In other words, the acid anion of the compound that functions as the acid generating compound preferably has the structure represented by the following formula (1).

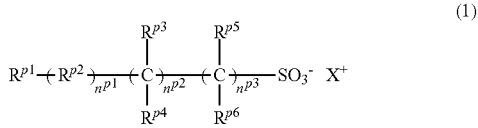  (1)

In the above formula (1), $R^{p1}$ represents a monovalent group that includes a ring structure having 6 or more ring atoms; $R^{p2}$ represents a divalent linking group; $R^{p3}$ and $R^{p4}$ each independently represent a hydrogen atom, a fluorine atom, a monovalent hydrocarbon group having 1 to 20 carbon atoms or a monovalent fluorinated hydrocarbon group having 1 to 20 carbon atoms; $R^{p5}$ and $R^{p6}$ each independently represent a fluorine atom or a monovalent fluorinated hydrocarbon group having 1 to 20 carbon atoms; $n^{p1}$ is an integer of 0 to 10; $n^{p2}$ is an integer of 0 to 10; $n^{p3}$ is an integer of 1 to 10, wherein in a case where $n^{p1}$ is no less than 2, a plurality of $R^{p2}$s may be identical or different, wherein in a case where $n^{p2}$ is no less than 2, a plurality of $R^{p3}$s may be identical or different, and a plurality of $R^{p4}$s may be identical or different, and wherein in a case where $n^{p3}$ is no less than 2, a plurality of $R^{p5}$s may be identical or different, and a plurality of $R^{p6}$s may be identical or different; and $X^+$ represents the cation (I) or the cation (II).

Note that the number of "ring atoms" as referred to herein means the number of atoms constituting a ring included in the aromatic ring structure, the aromatic heterocyclic ring structure, the alicyclic structure, and the aliphatic heterocyclic ring structure, and in the case of polycyclic ring structures, the number of "ring atoms" means the number of atoms constituting the plurality of rings. The "hydrocarbon group" as referred to includes a chain hydrocarbon group, an alicyclic hydrocarbon group and an aromatic hydrocarbon group. The "hydrocarbon group" may be either a saturated hydrocarbon group or an unsaturated hydrocarbon group. The "chain hydrocarbon group" as referred to means a hydrocarbon group not containing a cyclic structure and constituted only of a chain structure, and includes both of a linear hydrocarbon group and a branched hydrocarbon group. The "alicyclic hydrocarbon group" as referred to means a hydrocarbon group containing only an alicyclic structure as the ring structure and not containing an aromatic ring structure, including both of a monocyclic alicyclic hydrocarbon group and a polycyclic alicyclic hydrocarbon group. However, the alicyclic hydrocarbon group is not required to be constituted only of an alicyclic structure, and may also contain a chain structure in a part thereof. The "aromatic hydrocarbon group" as referred to means a hydrocarbon group containing an aromatic ring structure as the ring structure. However, the aromatic hydrocarbon group is not required to be constituted only of an aromatic ring structure, and may also contain a chain structure and an alicyclic structure in a part thereof.

The monovalent group that includes ring structure having 6 or more ring atoms, which is represented by $R^{p1}$ is exemplified by a monovalent group that includes an alicyclic structure having 6 or more ring atoms, a monovalent group that includes an aliphatic heterocyclic structure having 6 or more ring atoms, a monovalent group that includes an aromatic ring structure having 6 or more ring atoms, a monovalent group that includes an aromatic heterocyclic structure having 6 or more ring atoms, and the like.

Examples of the alicyclic structure having 6 or more ring atoms include:

monocyclic cycloalkane structures such as a cyclohexane structure, a cycloheptane structure, a cyclooctane structure, a cyclononane structure, a cyclodecane structure and a cyclododecane structure;

monocyclic cycloalkene structures such as a cyclohexene structure, a cycloheptene structure, a cyclooctene structure and a cyclodecene structure;

polycyclic cycloalkane structures such as a norbornane structure, an adamantane structure, a tricyclodecane structure and a tetracyclododecane structure;

polycyclic cycloalkene structures such as a norbornene structure and a tricyclodecene structure; and the like.

Examples of the aliphatic heterocyclic structure having 6 or more ring atoms include:

lactone structures such as a hexanolactone structure and a norbornanelactone structure;

sultone structures such as a hexanosultone structure and a norbornanesultone structure;

oxygen atom-containing heterocyclic structures such as an oxacycloheptane structure and an oxanorbornane structure;

nitrogen atom-containing heterocyclic structures such as an azacyclohexane structure and a diazabicyclooctane structure;

sulfur atom-containing heterocyclic structures such as a thiacyclohexane structure and a thianorbornane structure; and the like.

Examples of the aromatic ring structure having 6 or more ring atoms include: a benzene structure, a naphthalene structure, a phenanthrene structure, an anthracene structure and the like.

Examples of the aromatic heterocyclic structure having 6 or more ring atoms include: oxygen atom-containing heterocyclic structures such as a pyran structure and a benzopyran structure; nitrogen atom-containing heterocyclic structures such as a pyridine structure, a pyrimidine structure and an indole structure; and the like.

The lower limit of the number of ring atoms of the ring structure in $R^{p1}$ is preferably 7, more preferably 8, still more preferably 9, and particularly preferably 10. On the other hand, the upper limit of the number of ring atoms of the ring structure in $R^{p1}$ is preferably 15, more preferably 14, still more preferably 13, and particularly preferably 12. When the number of ring atoms falls within the above range, the abovementioned diffusion length of the acid can be decreased further moderately, and consequently LWR performances and the like of the resist material of the embodiment of the present invention can be more improved.

A part or all of hydrogen atoms included in the ring structure in $R^{p1}$ may be substituted with a substituent. Examples of the substituent include halogen atoms such as a fluorine atom, a chlorine atom, a bromine atom and an iodine atom, a hydroxy group, a carboxy group, a cyano group, a nitro group, an alkoxy group, an alkoxycarbonyl group, an alkoxycarbonyloxy group, an acyl group, an acyloxy group, and the like. Of these, a hydroxy group is preferred.

Of these, $R^{p1}$ represents preferably a monovalent group that includes an alicyclic structure having 6 or more ring atoms or a monovalent group that includes an aliphatic heterocyclic structure having 6 or more ring atoms, more preferably a monovalent group that includes an alicyclic structure having 9 or more ring atoms or a monovalent group that includes an aliphatic heterocyclic structure having 9 or more ring atoms, still more preferably an adamantyl group, a hydroxyadamantyl group, a norbornanelacton-yl group, a norbornanesultone-yl group or a 5-oxo-4-oxatricyclo[4.3.1.1$^{3,8}$]undecan-yl group, and particularly preferably an adamantyl group.

Examples of the divalent linking group represented by $R^{p2}$ include a carbonyl group, an ether group, a carbonyloxy group, a sulfide group, a thiocarbonyl group, a sulfonyl group, a divalent hydrocarbon group, and the like. The divalent linking group represented by $R^{p2}$ is preferably a carbonyloxy group, a sulfonyl group, an alkanediyl group or a cycloalkanediyl group, more preferably a carbonyloxy group or a cycloalkanediyl group, still more preferably a carbonyloxy group or a norbornanediyl group, and particularly preferably a carbonyloxy group.

The monovalent hydrocarbon group having 1 to 20 carbon atoms which may be represented by $R^{p3}$ or $R^{p4}$ is exemplified by an alkyl group having 1 to carbon atoms, and the like. The monovalent fluorinated hydrocarbon group having 1 to 20 carbon atoms which may be represented by $R^{p3}$ or $R^{p4}$ is exemplified by a fluorinated alkyl group having 1 to 20 carbon atoms, and the like. $R^{p3}$ and $R^{p4}$ each independently represent preferably a hydrogen atom, the fluorine atom or the fluorinated alkyl group, more preferably the fluorine atom or the perfluoroalkyl group, and still more preferably the fluorine atom or the trifluoromethyl group.

The monovalent fluorinated hydrocarbon group having 1 to 20 carbon atoms which may be represented by $R^{p5}$ or $R^{p6}$ is exemplified by a fluorinated alkyl group having 1 to 20 carbon atoms, and the like. $R^{p5}$ and $R^{p6}$ each independently represent preferably a fluorine atom or a fluorinated alkyl group, more preferably a fluorine atom or a perfluoroalkyl group, still more preferably a fluorine atom or a trifluoromethyl group, and particularly preferably a fluorine atom.

The lower limit of $n^{p1}$ is preferably 0. On the other hand, the upper limit of $n^{p1}$ is preferably 5, more preferably 3, still more preferably 2, and particularly preferably 1.

The lower limit of $n^{p2}$ is preferably 0. On the other hand, the upper limit of $n^{p2}$ is preferably 5, more preferably 2, and still more preferably 1.

The lower limit of $n^{p3}$ is preferably 1. On the other hand, the upper limit of $n^{p3}$ is preferably 5, more preferably 4, still more preferably 3, and particularly preferably 2.

Examples of the acid anion include, but not limited to, anions represented by the following formulae.

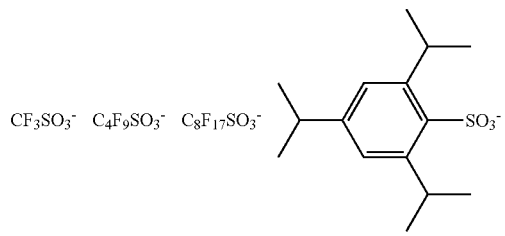

-continued
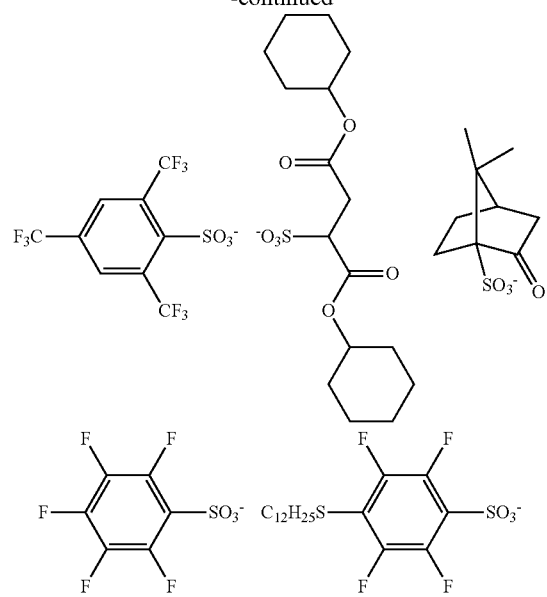
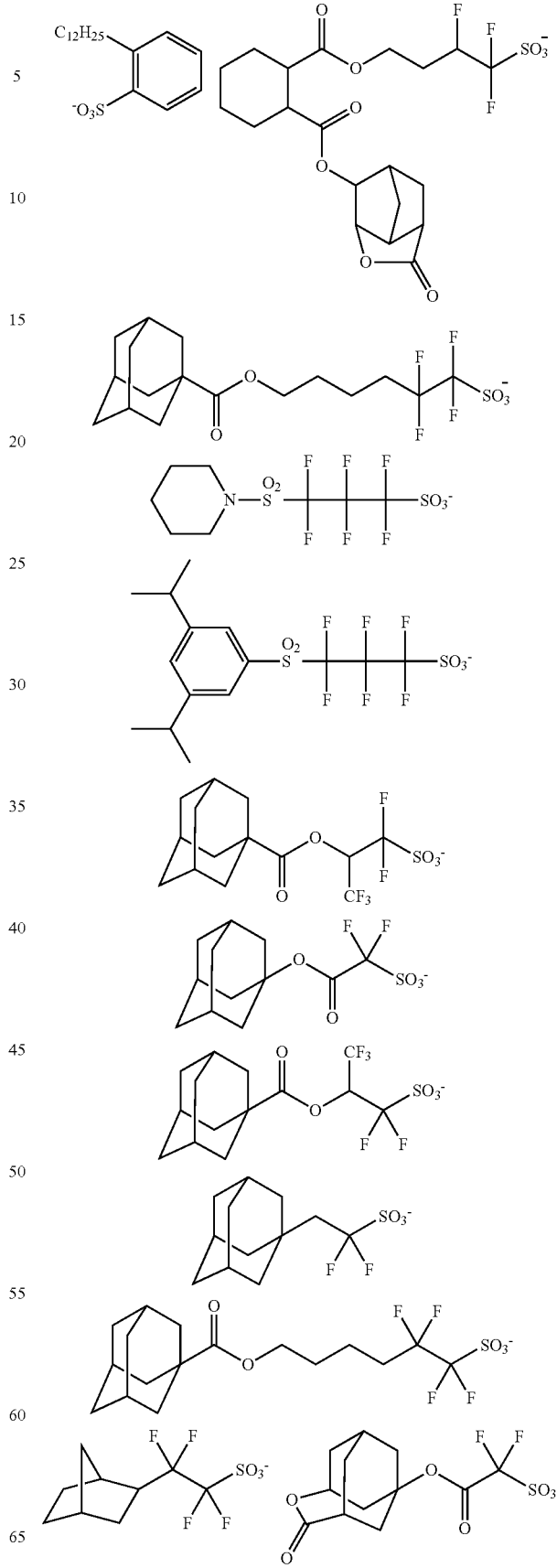
In addition, the anion shown in the above formula (1) preferred as the acid anion of the compound that functions as the acid generating compound is exemplified by the following anions.

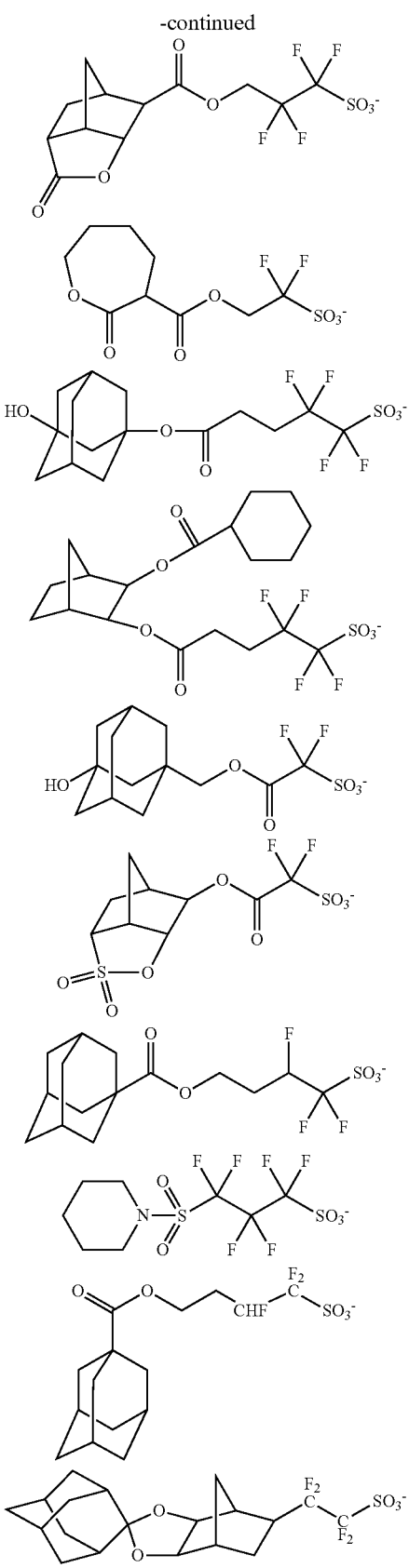

Examples of the compound (C1) and the compound (C2) include:

triphenylsulfonium trifluoromethanesulfonate, triphenylsulfonium nonafluoro-n-butanesulfonate, triphenylsulfonium perfluoro-n-octanesulfonate, triphenylsulfonium 2-bicyclo[2.2.1]hept-2-yl-1,1,2,2-tetrafluoroethanesulfonate, triphenylsulfonium 6-(adamantan-1-ylcarboxyoxy)-1,1,2,2-tetrafluorohexane-1-sulfonate, triphenylsulfonium adamantan-1-yloxycarbonylcarboxylate, 4-methoxyphenyldiphenylsulfonium 1,2-di(cyclohexyloxycarbonyl)ethane-1-sulfonate, and the like.

The lower limit of the content of the compound that is capable of generating the acid having a smaller pKa, of the compound (C1) and the compound (C2), with respect to 100 parts by mass of the component (a) or the component (c) is preferably 50% by mass, and more preferably 60% by mass. On the other hand, the upper limit of the content is preferably 90% by mass, and more preferably 80% by mass. Further, the lower limit of the content of the compound that is capable of generating the acid having a greater pKa, of the compound (C1) and the compound (C2), with respect to 100 parts by mass of the component (a) or the component (c) is preferably 5% by mass, and more preferably 10% by mass. On the other hand, the upper limit of the content is preferably 50% by mass, and more preferably 40% by mass. When each content of the compound that is capable of generating the acid having a smaller pKa and the compound that is capable of generating the acid having a greater pKa falls within the above range, the sensitivity and lithography performances of the chemically amplified resist material can be more improved.

(a) Radiation-Sensitive Acid-and-Sensitizer Generating Agent

The radiation-sensitive acid-and-sensitizer generating agent (a) is capable of generating, upon the irradiation with a first radioactive ray having a wavelength of no greater than 250 nm without the irradiation with a second radioactive ray having a wavelength of greater than 250 nm, an acid and a radiation-sensitive sensitizer that absorbs the second radioactive ray, but the radiation-sensitive acid-and-sensitizer generating agent (a) substantially does not generate the acid and the radiation-sensitive sensitizer upon an irradiation with the second radioactive ray without an irradiation with the first radioactive ray.

The compound (C1) and the compound (C2) that serve in the radiation-sensitive acid-and-sensitizer generating agent (a) are exemplified by an onium salt compound, of the compound (C1) and the compound (C2). Also, examples of the onium salt compound include a sulfonium salt compound, a tetrahydrothiophenium salt compound, and the like.

The cation (I) and the cation (II) in the compound (C1) and the compound (C2) are exemplified by triphenylsulfonium, and the like.

The radiation-sensitive acid-and-sensitizer generating agent (a) may include a compound other than the compound (C1) and the compound (C2), and such a compound is exemplified by other onium salt compound, a diazomethane compound, a sulfonimide compound, and the like. The onium salt compound is exemplified by an iodonium salt compound, and the like. As the radiation-sensitive acid-and-sensitizer generating agent (a) other than the compound (C1) and the compound (C2), an iodonium salt compound is preferred.

The sulfonium salt compound as referred to is constituted with a sulfonium cation and an acid anion. As the sulfonium salt compound, compounds represented by the following formulae (I) to (III) are preferred.

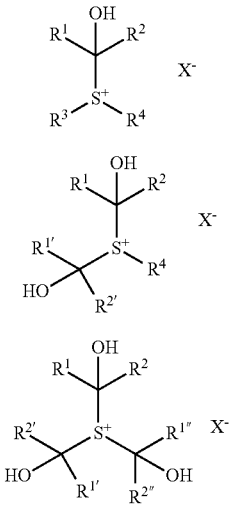

In the above formulae (I) to (III), $R^1$, $R^2$, $R^{1'}$, $R^{2'}$, $R^{1''}$, $R^{2''}$, $R^3$ and $R^4$ each independently represent: a hydrogen atom; a phenyl group; a naphthyl group; an anthracenyl group; a phenoxy group; a naphthoxy group; an anthracenoxy group; an amino group; an amide group; a halogen atom; a saturated or unsaturated linear, branched or cyclic hydrocarbon group, preferably an alkyl group, having 1 to 30 carbon atoms, preferably 1 to 5 carbon atoms; a phenoxy group substituted with an alkoxy group having 1 to 5 carbon atoms, a hydroxy group, an amino group, an amide group, or an alkyl group having 1 to 5 carbon atoms; a phenyl group substituted with a saturated or unsaturated linear, branched or cyclic hydrocarbon group, preferably an alkyl group, having 1 to 30 carbon atoms, preferably 1 to 5 carbon atoms, an alkoxy group having 1 to 5 carbon atoms, an amino group, an amide group, or a hydroxy group; a naphthoxy group substituted with an alkoxy group having 1 to carbon atoms, an alkyl group having 1 to 5 carbon atoms, an amino group, an amide group, or a hydroxy group; an anthracenoxy group substituted with an alkoxy group having 1 to 5 carbon atoms, an alkyl group having 1 to 5 carbon atoms, an amino group, an amide group, or a hydroxy group; a saturated or unsaturated linear, branched or cyclic hydrocarbon group, preferably an alkyl group, having 1 to 30 carbon atoms, preferably 1 to 5 carbon atoms, substituted with an alkoxy group having 1 to 5 carbon atoms, a phenoxy group, a naphthoxy group, an anthracenoxy group, an amino group, an amide group, or a hydroxy group; or a carbonyl group to which an alkyl group having 1 to 12 carbon atoms bonds. In the above formulae (I) to (III), the hydrogen atom of the hydroxy group may be substituted with: a phenyl group; a halogen atom; a saturated or unsaturated linear, branched or cyclic hydrocarbon group, preferably an alkyl group, having 1 to 30 carbon atoms, preferably 1 to 5 carbon atoms; or a phenyl group substituted with a saturated or unsaturated linear, branched or cyclic hydrocarbon group, preferably an alkyl group, having 1 to 30 carbon atoms, preferably 1 to 5 carbon atoms, an alkoxy group having 1 to 5 carbon atoms, or a hydroxy group. In a case where the hydrogen atom of the hydroxy group is substituted, the sulfonium salt compound shall include a ketal compound group or an acetal compound group. In the formula (I), any at least two of the groups represented by $R^1$, $R^2$, $R^3$, and $R^4$ may taken together form a ring structure via a single bond or a double bond, or via a bond that includes —$CH_2$—, —O—, —S—, —$SO_2$—, —$SO_2NH$—, —C(=O)—, —C(=O)O—, —NHCO—, —NHC(=O)NH—, —$CHR^e$—, —$CR^e_2$—, —NH— or —$NR^e$—. In the formulae (II), any at least two of the groups represented by $R^1$, $R^2$, $R^{1'}$, $R^{2'}$ and $R^4$ may taken together form a ring structure via a single bond or a double bond, or via a bond that includes —$CH_2$—, —O—, —S—, —$SO_2$—, —$SO_2NH$—, —C(=O)—, —C(=O)O—, —NHCO—, —NHC(=O)NH—, —$CHR^e$—, —$CR^e_2$—, —NH— or —$NR^e$—. In the formula (III), any at least two of the groups represented by $R^1$, $R^2$, $R^{1'}$, $R^{2'}$, $R^{1''}$ and $R^{2''}$ may taken together form a ring structure via a single bond or a double bond, or via a bond that includes —$CH_2$—, —O—, —S—, —$SO_2$—, —$SO_2NH$—, —C(=O)—, —C(=O)O—, —NHCO—, —NHC(=O)NH—, —$CHR^e$—, —$CR^e_2$—, —NH— or —$NR^e$—. $R^e$ represents: a phenyl group; a phenoxy group; a halogen atom; a saturated or unsaturated linear, branched or cyclic hydrocarbon group, preferably an alkyl group, having 1 to 30 carbon atoms, preferably 1 to 5 carbon atoms; a phenoxy group substituted with an alkoxy group having 1 to 5 carbon atoms, a hydroxy group, or an alkyl group having 1 to 5 carbon atoms; or a phenyl group substituted with a saturated or unsaturated linear, branched or cyclic hydrocarbon group, preferably an alkyl group, having 1 to 30 carbon atoms, preferably 1 to 5 carbon atoms, an alkoxy group having 1 to 5 carbon atoms, or a hydroxy group. $R^1$, $R^2$, $R^{1'}$, $R^{2'}$, $R^{1''}$, $R^{2''}$, $R^3$ and $R^4$ each independently represent preferably: a phenyl group; a phenoxy group; a phenoxy group substituted with an alkyl group having 1 to 5 carbon atoms; or a phenyl group substituted with an alkoxy group having 1 to 5 carbon atoms or a hydroxy group. In the formulae (I) to (III), $X^-$ represents an anion derived from an acid, preferably a strong acid, and more preferably a superacid.

In the above formulae (I) to (III), examples of the group represented by —C(—OH)$R^1R^2$, —C(—OH)$R^{1'}R^{2'}$, —C(—OH)$R^{1''}R^{2''}$ or the like include groups represented by the following formulae. It is to be noted that * in the formulae denotes a binding site to the sulfur ion in the above formulae (I) to (III). In the group represented by —C(—OH)$R^1R^2$, —C(—OH)$R^{1'}R^{2'}$, or —C(—OH)$R^{1''}R^{2''}$, the hydroxy group and the carbon atom to which the hydroxy group bonds are to give a carbonyl group upon the patternwise exposure. Thus, in the compounds represented by the above formulae (I) to (III), the group represented by —C(—OH)$R^1R^2$, —C(—OH)$R^{1'}R^{2'}$, or —C(—OH)$R^{1''}R^{2''}$ is dissociated after the patternwise exposure to generate the radiation-sensitive sensitizer.

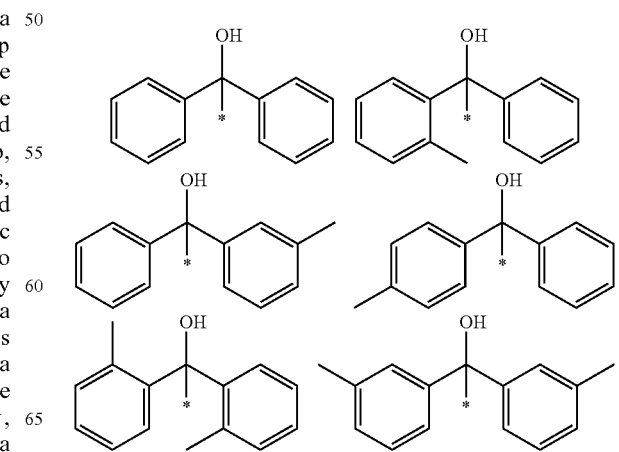

-continued
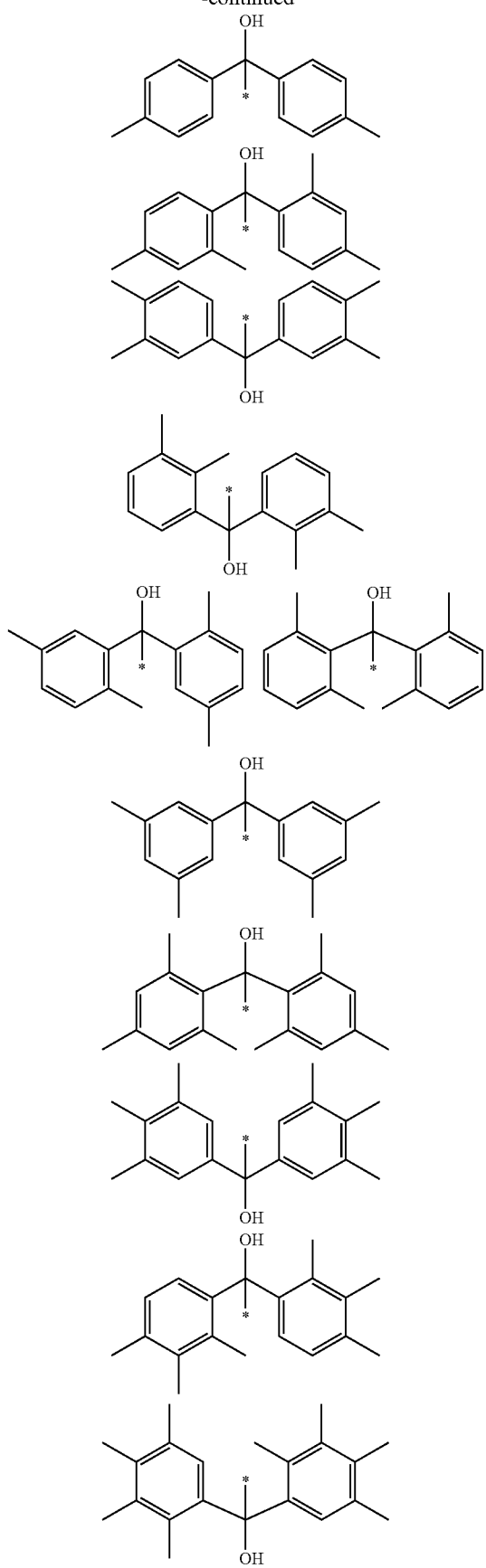
-continued
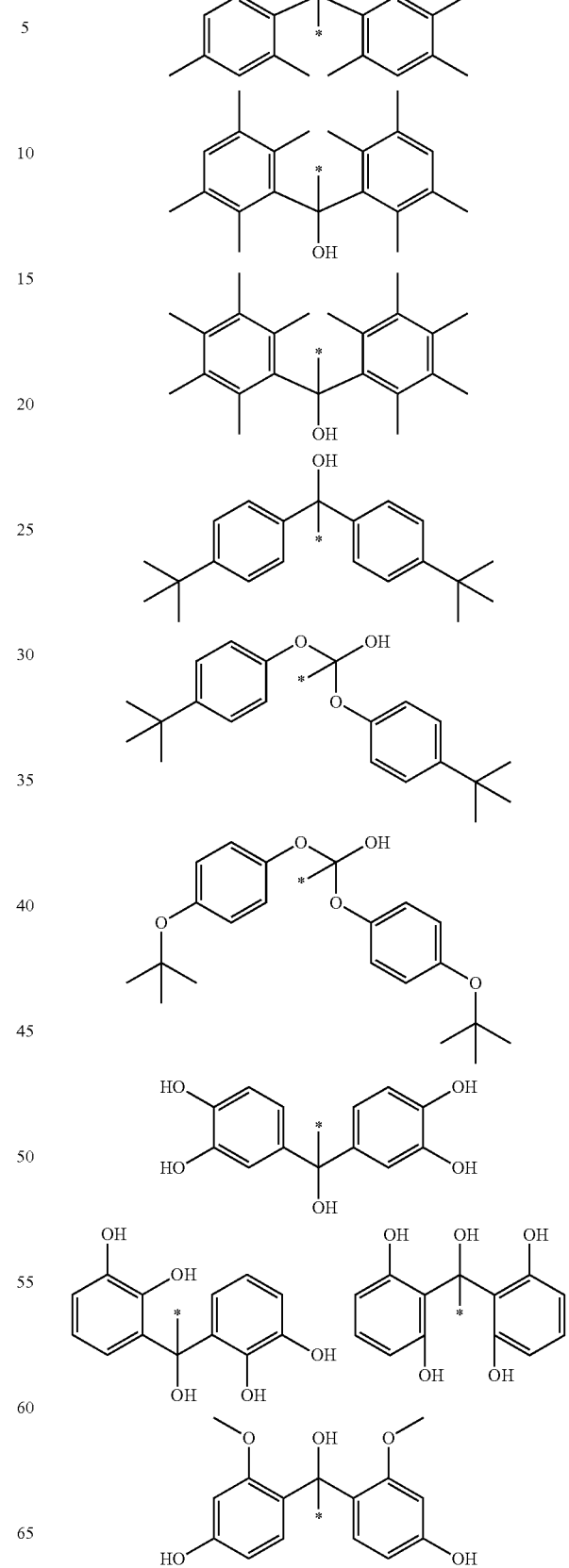

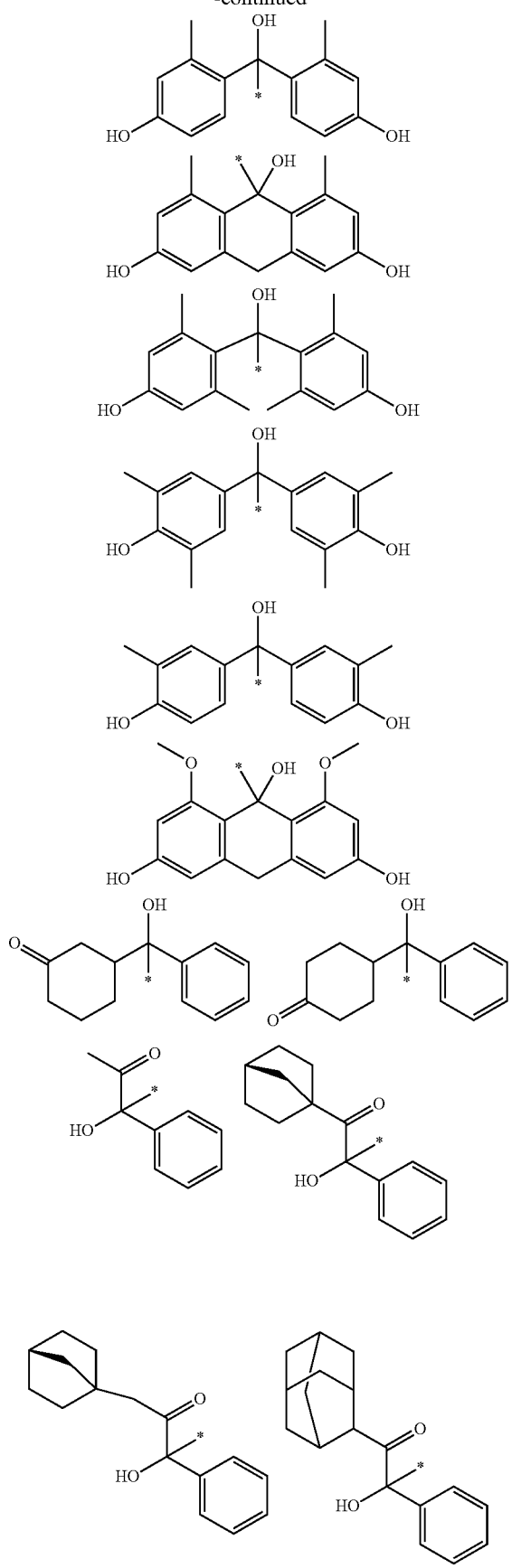
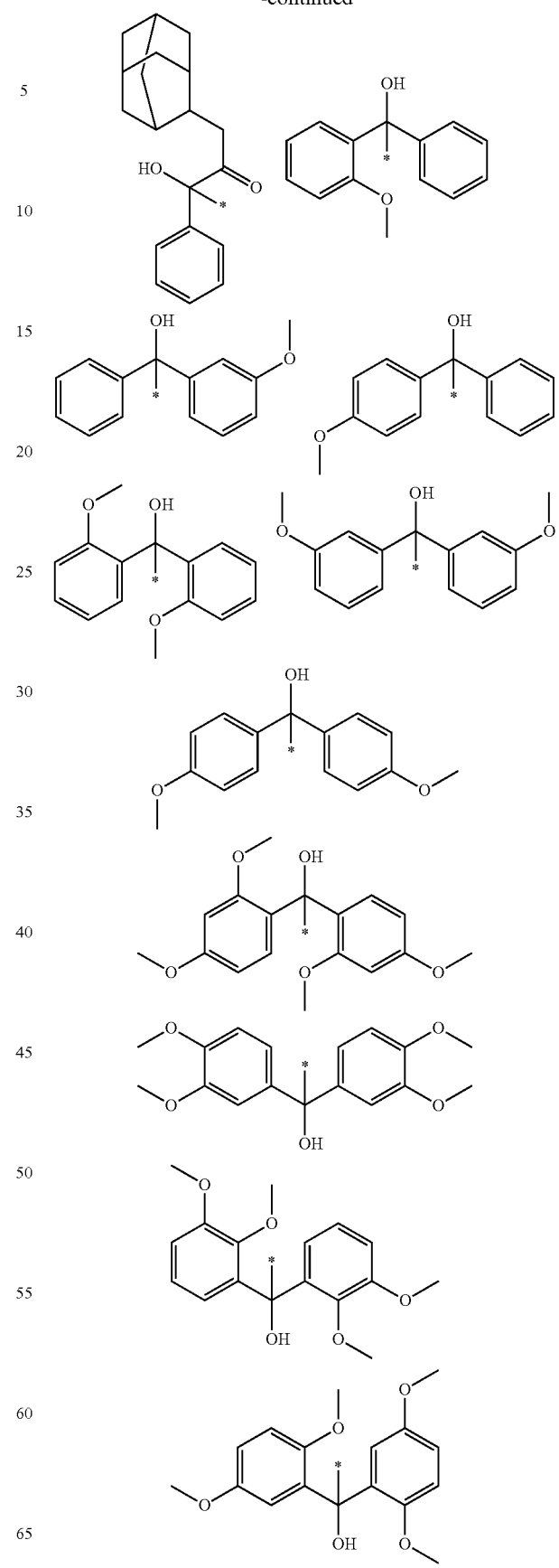

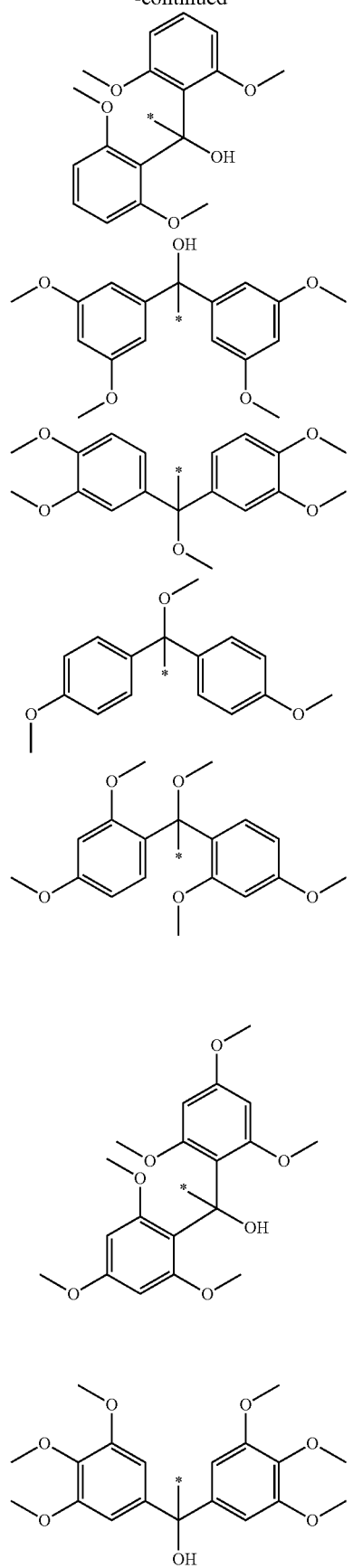
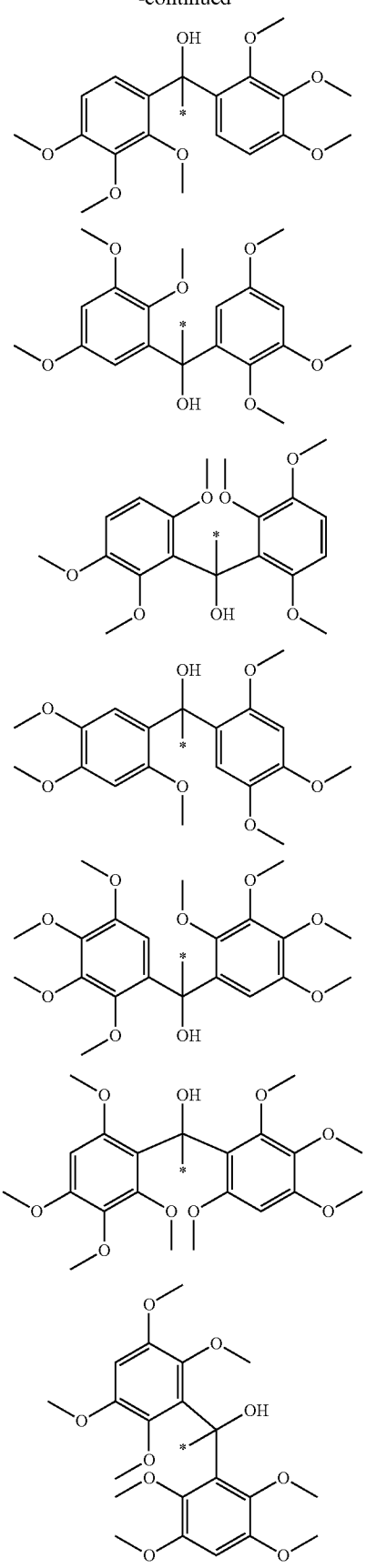

47
-continued
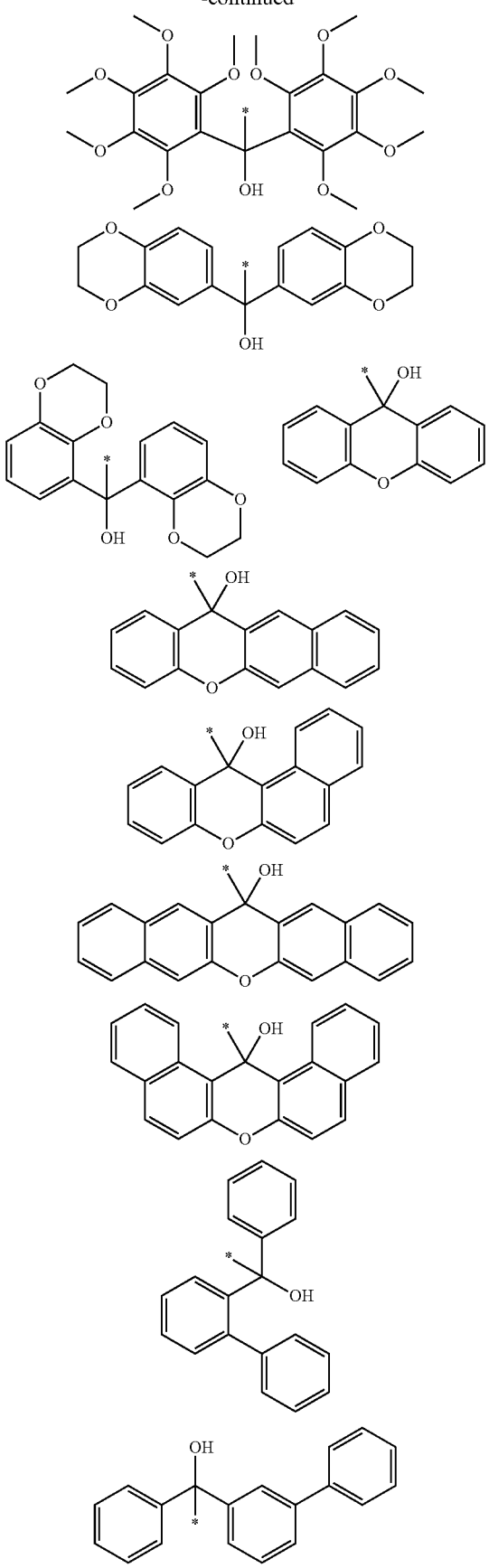
48
-continued
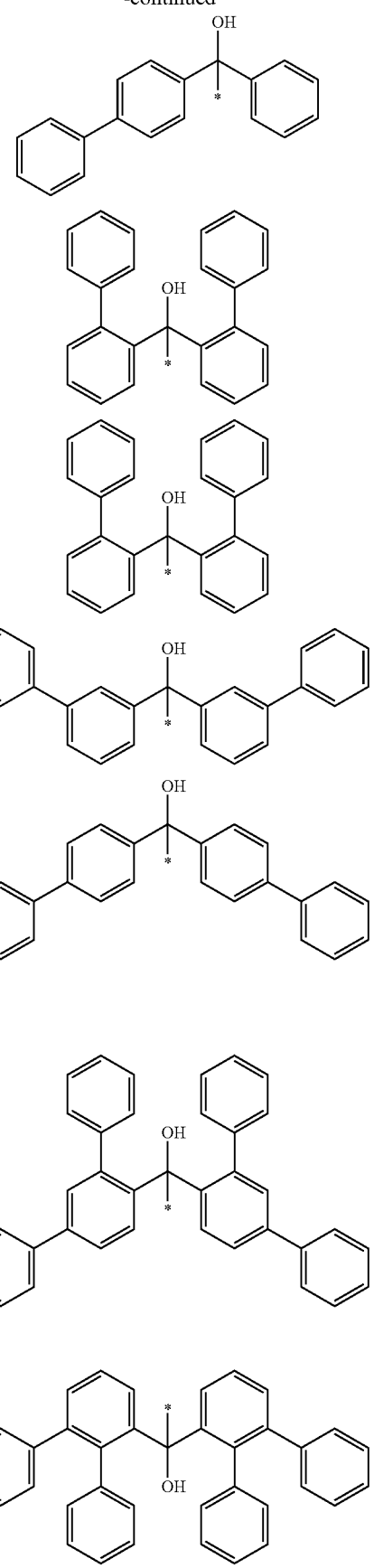

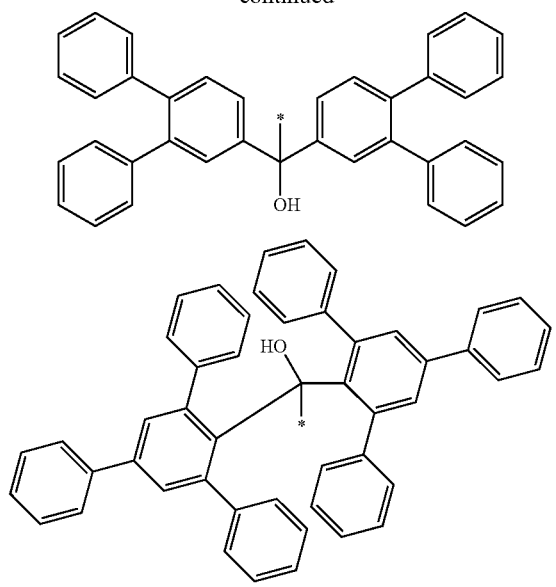
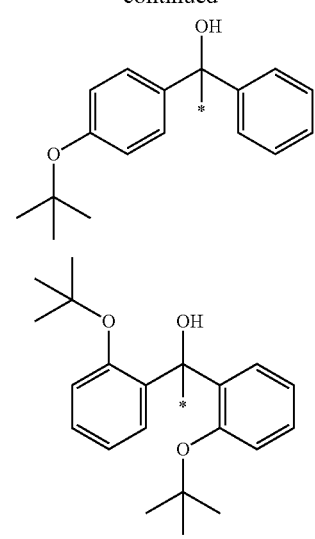
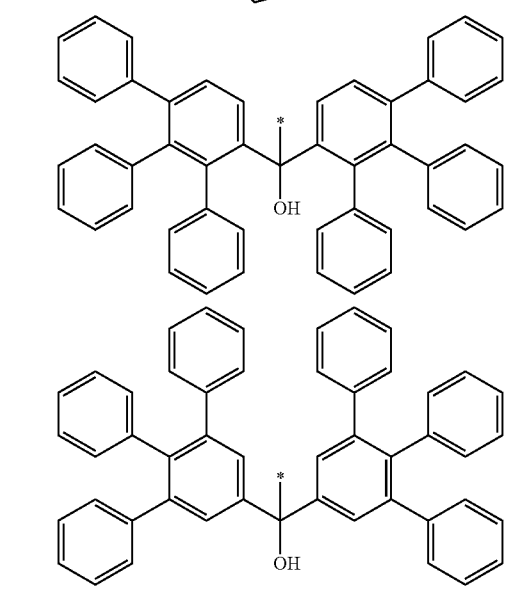
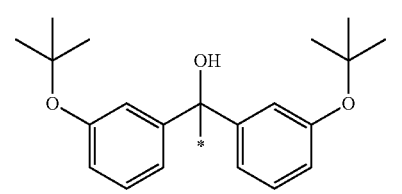
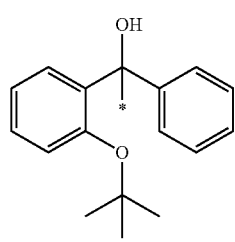
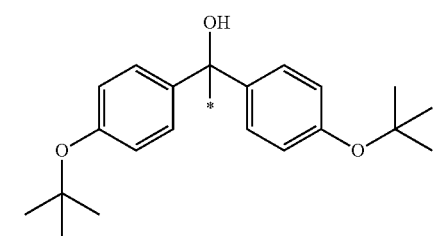
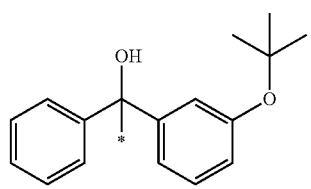
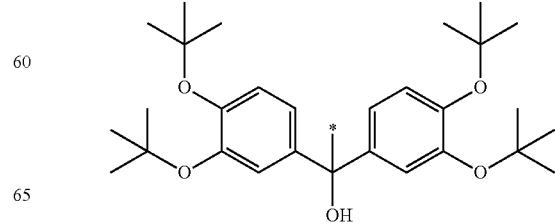

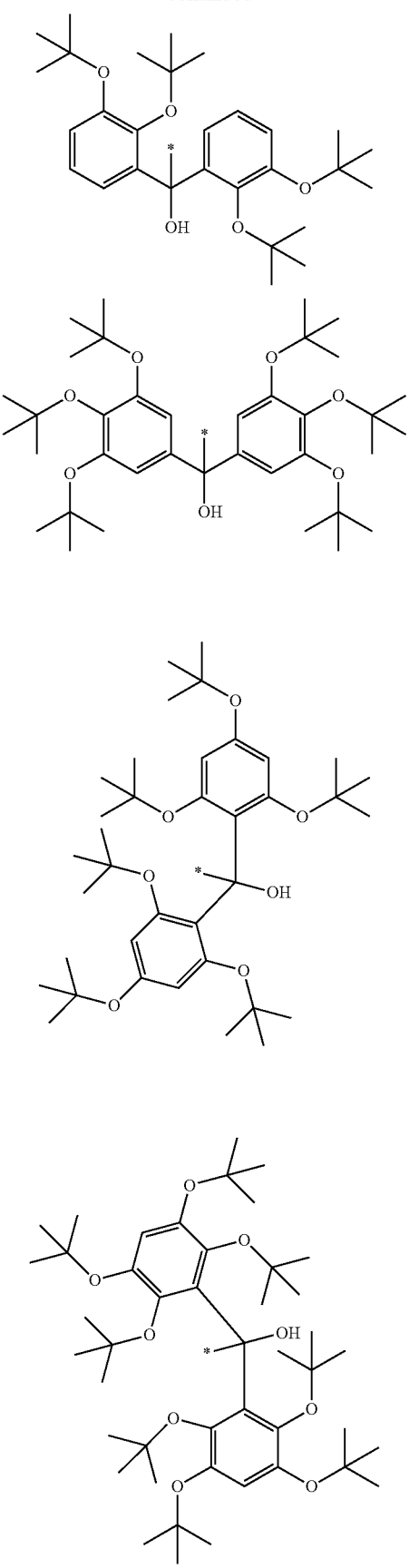
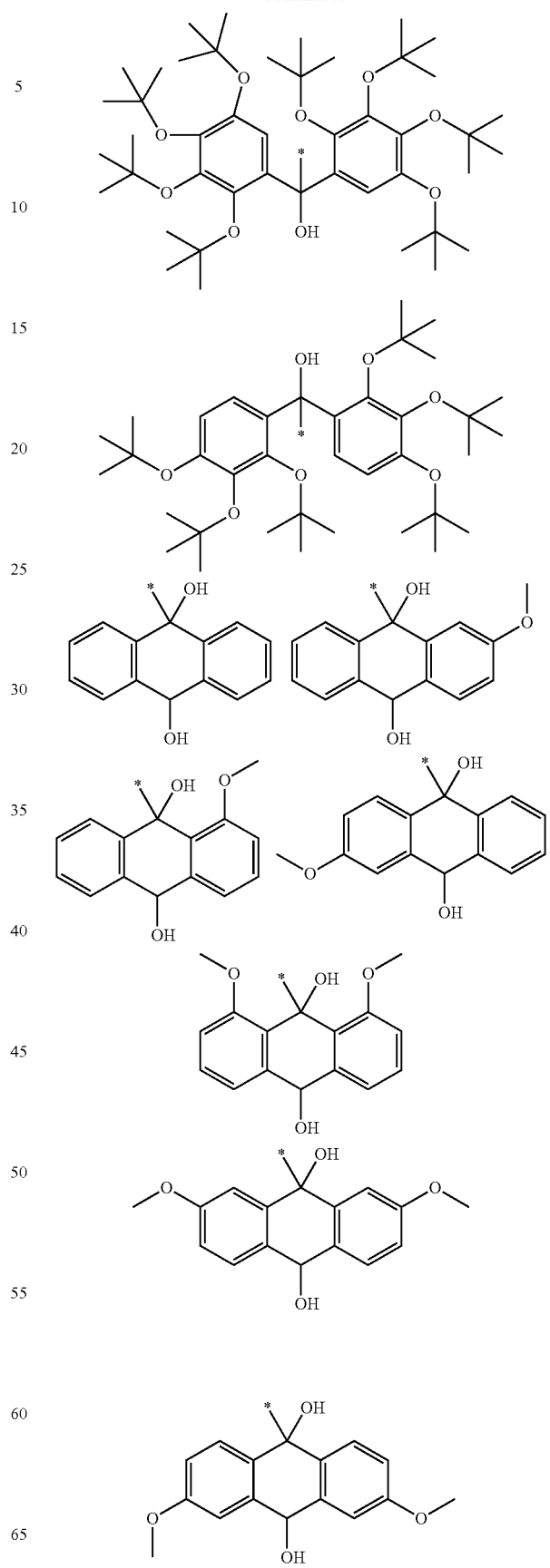

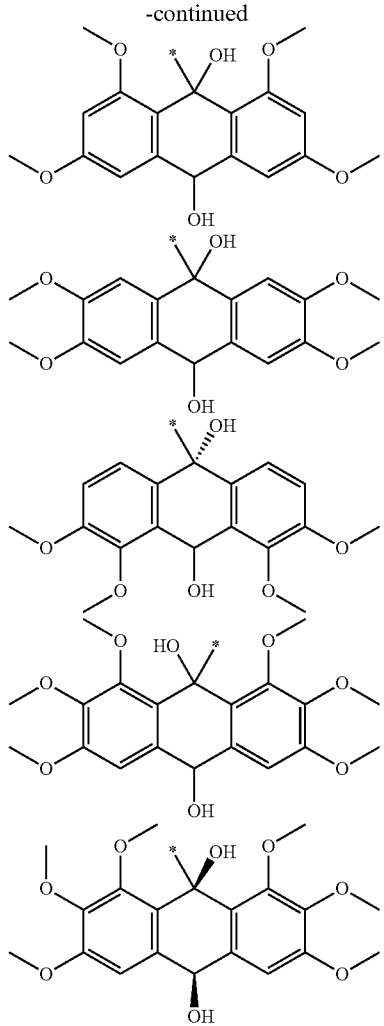

The iodonium salt compound is constituted with an iodonium cation and an acid anion. As the iodonium salt compound, compounds represented by the following formulae (IV) to (V) are preferred.

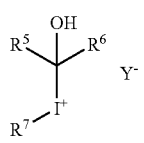 (IV)

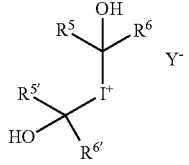 (V)

In the above formulae (IV) to (V), $R^5$, $R^6$, $R^{5'}$, $R^{6'}$, and $R^7$ each independently represent: a hydrogen atom; a phenyl group; a naphthyl group; an anthracenyl group; a phenoxy group; a naphthoxy group; an anthracenoxy group; an amino group; an amide group; a halogen atom; a saturated or unsaturated linear, branched or cyclic hydrocarbon group, preferably an alkyl group, having 1 to 30 carbon atoms, preferably 1 to 5 carbon atoms; a phenoxy group substituted with an alkoxy group having 1 to 5 carbon atoms, a hydroxy group, an amino group, an amide group, or an alkyl group having 1 to 5 carbon atoms; a phenyl group substituted with a saturated or unsaturated linear, branched or cyclic hydrocarbon group, preferably an alkyl group, having 1 to 30 carbon atoms, preferably 1 to 5 carbon atoms, an alkoxy group having 1 to 5 carbon atoms, an amino group, an amide group, or a hydroxy group; a naphthoxy group substituted with an alkoxy group having 1 to 5 carbon atoms, an alkyl group having 1 to 5 carbon atoms, an amino group, an amide group, or a hydroxy group; an anthracenoxy group substituted with an alkoxy group having 1 to 5 carbon atoms, an alkyl group having 1 to 5 carbon atoms, an amino group, an amide group, or a hydroxy group; a saturated or unsaturated linear, branched or cyclic hydrocarbon group, preferably an alkyl group, having 1 to 30 carbon atoms, preferably 1 to 5 carbon atoms, substituted with an alkoxy group having 1 to 5 carbon atoms, a phenoxy group, a naphthoxy group, an anthracenoxy group, an amino group, an amide group, or a hydroxy group; or a carbonyl group to which an alkyl group having 1 to 12 carbon atoms bonds. In the above formulae (IV) to (V), the hydrogen atom of the hydroxy group may be substituted with: a phenyl group; a halogen atom; a saturated or unsaturated linear, branched or cyclic hydrocarbon group, preferably an alkyl group, having 1 to 30 carbon atoms, preferably 1 to 5 carbon atoms; or a phenyl group substituted with a saturated or unsaturated linear, branched or cyclic hydrocarbon group, preferably an alkyl group, having 1 to 30 carbon atoms, preferably 1 to 5 carbon atoms, an alkoxy group having 1 to 5 carbon atoms, or a hydroxy group. In a case where the hydrogen atom of the hydroxy group is substituted, the iodonium salt compound shall include a ketal compound group or an acetal compound group. In the formula (IV), any at least two of the groups represented by $R^5$, $R^6$ and $R^7$ may taken together form a ring structure via a single bond or a double bond, or via a bond that includes —CH$_2$—, —O—, —S—, —SO$_2$NH—, —C(=O)—, —C(=O)O—, —NHCO—, —NHC(=O)NH—, —CHR$^f$—, —CR$^f_2$—, —NH— or —NR$^f$—. In the formula (V), any at least two of the groups represented by $R^5$, $R^6$, $R^{5'}$ and $R^{6'}$ may taken together form a ring structure via a single bond or a double bond, or via a bond that includes —CH$_2$—, —O—, —S—, —SO$_2$NH—, —C(=O)—, —C(=O)O—, —NHCO—, —NHC(=O)NH—, —CHR$^f$—, —CR$^f_2$—, —NH— or —NR$^f$—. R$^f$ represents: a phenyl group; a phenoxy group; a halogen atom; a saturated or unsaturated linear, branched or cyclic hydrocarbon group, preferably an alkyl group, having 1 to 30 carbon atoms, preferably 1 to 5 carbon atoms; a phenoxy group substituted with an alkoxy group having 1 to 5 carbon atoms, a hydroxy group, or an alkyl group having 1 to 5 carbon atoms; or a phenyl group substituted with a saturated or unsaturated linear, branched or cyclic hydrocarbon group, preferably an alkyl group, having 1 to 30 carbon atoms, preferably 1 to 5 carbon atoms, an alkoxy group having 1 to 5 carbon atoms, or a hydroxy group. $R^5$, $R^6$, $R^{5'}$, $R^{6'}$, and $R^7$ each independently represent preferably: a phenyl group; a phenoxy group; a phenoxy group substituted with an alkoxy group having 1 to 5 carbon atoms, a hydroxy group, or an alkyl group having 1 to 5 carbon atoms; or a phenyl group substituted with an alkoxy group having 1 to 5 carbon atoms or a hydroxy group. In the formulae (IV) to (V), Y$^-$ represents an anion derived from an acid, preferably a strong acid, and more preferably a superacid.

In the above formulae (IV) to (V), examples of the group represented by —C(—OH)R$^5$R$^6$ or —C(—OH)R$^{5'}$R$^{6'}$ include groups similar to those exemplified as the group represented by —C(—OH)R¹R², —C(—OH)R¹'R²', —C(—OH)R¹"R²" or the like in connection with the above formulae (I) to (III).

The radiation-sensitive acid-and-sensitizer generating agent (a) may be a part of the polymer constituting the polymer component (1). In this case, the radiation-sensitive acid-and-sensitizer generating agent (a) is present in the form of a group obtained by eliminating one hydrogen atom from the aforementioned compound and bound to the polymer.

In the case where the radiation-sensitive acid-and-sensitizer generating agent (a) is the component different from the polymer component (1), the lower limit of the amount of the radiation-sensitive acid-and-sensitizer generating agent (a) blended with respect to 100 parts by mass of the polymer component (1) is preferably 0.005 parts by mass, and more preferably 0.1 parts by mass. On the other hand, the upper limit of the amount of the radiation-sensitive acid-and-sensitizer generating agent (a) blended is preferably 50 parts by mass, and more preferably 30 parts by mass.

In the case where the radiation-sensitive acid-and-sensitizer generating agent (a) is a part of the polymer constituting the polymer component (1), the proportion of the radiation-sensitive acid-and-sensitizer generating agent (a) contained with respect to 1 mol of the polymer component (1) is preferably 0.001 mol, more preferably 0.002 mol, and still more preferably 0.01 mol. On the other hand, the upper limit of the proportion of the radiation-sensitive acid-and-sensitizer generating agent (a) is preferably 0.5 mol, and more preferably 0.3 mol.

When the amount of the radiation-sensitive acid-and-sensitizer generating agent (a) blended or the proportion of the radiation-sensitive acid-and-sensitizer generating agent (a) contained is less than the lower limit, the sensitivity may be deteriorated. To the contrary, when the amount of the radiation-sensitive acid-and-sensitizer generating agent (a) blended or the proportion of the radiation-sensitive acid-and-sensitizer generating agent (a) contained is greater than the upper limit, it may be difficult to form the resist material film, and/or the rectangularity of the cross-sectional shape of the resist pattern may be deteriorated.

(b) Radiation-Sensitive Sensitizer Generating Agent

The radiation-sensitive sensitizer generating agent (b) is a component that is capable of generating, upon the irradiation with the first radioactive ray without the irradiation with the second radioactive ray, the radiation-sensitive sensitizer that absorbs the second radioactive ray, but the radiation-sensitive sensitizer generating agent (b) substantially does not generate the radiation-sensitive sensitizer upon the irradiation with the second radioactive ray without the irradiation with the first radioactive ray, and is different from the radiation-sensitive acid-and-sensitizer generating agent (a).

According to the chemically amplified resist material, the chemical structure of the radiation-sensitive sensitizer generating agent (b) is altered through a direct or indirect reaction upon the irradiation with the first radioactive ray to generate a radiation-sensitive sensitizer that assists in the generation of the acid upon the irradiation with the second radioactive ray. Since the radiation-sensitive sensitizer absorbs the second radioactive ray more readily as compared with the radiation-sensitive sensitizer generating agent (b), the absorption capacity with respect to the second radioactive ray differs significantly upon the patternwise exposure with the first radioactive ray between the light-exposed regions where the radiation-sensitive sensitizer is generated and the patternwise unexposed regions where the radiation-sensitive sensitizer is not generated, whereby a contrast of the absorption capacity can be attained more easily.

The radiation-sensitive sensitizer generating agent (b) is preferably converted, upon the irradiation with the first radioactive ray, into a carbonyl compound having a carbonyl group absorbing the second radioactive ray. Examples of the carbonyl compound include aldehydes, ketones, carboxylic acids, carboxylic acid esters, and the like. By the above-described reaction, shift of the peak of absorption wavelength of the radioactive ray takes place only with the radiation-sensitive sensitizer generating agent (b) in the patternwise exposed regions. Therefore, following the patternwise exposure, by performing the floodwise exposure with the radioactive ray having a wavelength that can be absorbed only by the patternwise exposed regions, selective sensitization of the patternwise exposed regions alone is enabled. The radiation-sensitive sensitizer generating agent (b) is preferably an alcohol compound represented by the following formula (VI), and may also be a secondary alcohol compound. It is to be noted that as referred to herein, the "alcohol compound" as referred to means not only a compound containing an alcoholic hydroxyl group, but may also be a ketal compound and an acetal compound as well as an ortho ester compound and the like, which are obtained by substitution of an hydrogen atom in the alcoholic hydroxyl group. In the case of the radiation-sensitive sensitizer generating agent (b) being a ketal compound or an acetal compound, heating may take place between the patternwise exposure and the floodwise exposure, in order to accelerate a hydrolysis reaction of a carbonyl compound by an acid catalyst generated upon the patternwise exposure.

(VI)

In the formula (VI), $R^8$, $R^9$ and $R^{10}$ each independently represent: a hydrogen atom; a phenyl group; a naphthyl group; an anthracenyl group; an alkoxy group having 1 to 5 carbon atoms; an alkylthio group having 1 to 5 carbon atoms; a phenoxy group; a naphthoxy group; an anthracenoxy group; an amino group; an amide group; a halogen atom; a saturated or unsaturated linear, branched or cyclic hydrocarbon group, preferably an alkyl group, having 1 to 30 carbon atoms, preferably 1 to 5 carbon atoms; an alkoxy group having 1 to 5 carbon atoms substituted with a saturated or unsaturated linear, branched or cyclic hydrocarbon group, preferably an alkyl group, having 1 to 30 carbon atoms, preferably 1 to 5 carbon atoms, an alkoxy group having 1 to 5 carbon atoms, an amino group, an amide group, or a hydroxyl group; an alkylthio group having 1 to 5 carbon atoms substituted with a saturated or unsaturated linear, branched or cyclic hydrocarbon group, preferably an alkyl group, having 1 to 30 carbon atoms, preferably 1 to 5 carbon atoms, an alkoxy group having 1 to 5 carbon atoms, an amino group, an amide group, or a hydroxyl group; a phenoxy group substituted with an alkoxy group having 1 to 5 carbon atoms, a hydroxyl group, an amino group, an amide group, or an alkyl group having 1 to 5 carbon atoms; a phenyl group substituted with a saturated or unsaturated linear, branched or cyclic hydrocarbon group, preferably an alkyl group, having 1 to 30 carbon atoms, preferably 1 to 5 carbon atoms, an alkoxy group having 1 to 5 carbon atoms, an amino group, an amide group, or a hydroxyl group; a naphthoxy group substituted with an alkoxy group having 1 to 5 carbon atoms, an alkyl group having 1 to 5 carbon atoms, an amino group, an amide group, or a hydroxyl group; an anthracenoxy group substituted with an alkoxy group having 1 to 5 carbon atoms, an alkyl group having 1 to 5 carbon atoms, an amino group, an amide group, or a hydroxyl group; a saturated or unsaturated linear, branched or cyclic hydrocarbon group, preferably an alkyl group, having 1 to 30 carbon atoms, preferably 1 to 5 carbon atoms, substituted with an alkoxy group having 1 to 5 carbon atoms, a phenoxy group, a naphthoxy group, an anthracenoxy group, an amino group, an amide group, or a hydroxyl group; or a carbonyl group to which an alkyl group having 1 to 12 carbon atoms bonds. The alcohol compound may be a thiol compound having a thiol group in place of the alcoholic hydroxyl group (hydroxyl group) in the formula (VI). In the above formula (VI), the hydrogen atom of the hydroxyl group or the thiol group may be substituted with: a phenyl group; a halogen atom; a saturated or unsaturated linear, branched or cyclic hydrocarbon group, preferably an alkyl group, having 1 to 30 carbon atoms, preferably 1 to 5 carbon atoms; or a phenyl group substituted with a saturated or unsaturated linear, branched or cyclic hydrocarbon group, preferably an alkyl group, having 1 to 30 carbon atoms, preferably 1 to 5 carbon atoms, an alkoxy group having 1 to 5 carbon atoms, or a hydroxyl group. In the formula, any at least two of the groups represented by $R^8$, $R^9$ and $R^{10}$ may taken together form a ring structure via a single bond or a double bond, or via a bond that includes —$CH_2$—, —O—, —S—, —$SO_2$—, —$SO_2NH$—, —C(=O)—, —C(=O)O—, —NHCO—, —NHC(=O)NH—, —$CHR^g$—, —$CR^g_2$—, —NH— or —$NR^g$—, wherein $R^g$ represents: a phenyl group; a phenoxy group; a halogen atom; a saturated or unsaturated linear, branched or cyclic hydrocarbon group, preferably an alkyl group, having 1 to 30 carbon atoms, preferably 1 to 5 carbon atoms; a phenoxy group substituted with an alkoxy group having 1 to 5 carbon atoms, a hydroxyl group, or an alkyl group having 1 to 5 carbon atoms; or a phenyl group substituted with a saturated or unsaturated linear, branched or cyclic hydrocarbon group, preferably an alkyl group, having 1 to 30 carbon atoms, preferably 1 to 5 carbon atoms, an alkoxy group having 1 to 5 carbon atoms, or a hydroxyl group. $R^8$, $R^9$ and $R^{10}$ each independently represent preferably: a hydrogen atom; a phenyl group; a phenoxy group; a phenoxy group substituted with an alkoxy group having 1 to 5 carbon atoms, a hydroxyl group, or an alkyl group having 1 to 5 carbon atoms; or a phenyl group substituted with an alkoxy group having 1 to 5 carbon atoms or a hydroxyl group.

It is to be noted that the ketal compound or the acetal compound, in which a hydrogen atom in the hydroxyl group in the formula (VI) is substituted, is preferably a compound represented by the following formula (XXXVI). In other words, the radiation-sensitive sensitizer generating agent (b) may also be a compound represented by the following formula (XXXVI). In the case of any one of $R^9$ and $R^{10}$ being a hydrogen atom, a compound represented by the following formula (XXXVI) can be considered to be an acetal compound.

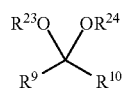

(XXXVI)

In the above formula (XXXVI), $R^9$ and $R^{10}$ are as defined in $R^9$ and $R^{10}$ in the above formula (VI), respectively. $R^9$ and $R^{10}$ may taken together represent a ring structure, similarly to $R^9$ and $R^{10}$ in the above formula (VI). In the formula (XXXVI), $R^{23}$ and $R^{24}$ each independently represent: a phenyl group; a halogen atom; a saturated or unsaturated linear, branched or cyclic hydrocarbon group, preferably an alkyl group, having 1 to 30 carbon atoms, preferably 1 to 5 carbon atoms; or a phenyl group substituted with a saturated or unsaturated linear, branched or cyclic hydrocarbon group, preferably an alkyl group, having 1 to 30 carbon atoms, preferably 1 to 5 carbon atoms, an alkoxy group having 1 to 5 carbon atoms, or a hydroxyl group, wherein $R^{23}$ and $R^{24}$ may taken together represent a ring structure via a single bond or a double bond, or via a bond that includes —$CH_2$—, —O—, —S—, —$SO_2$—, —$SO_2NH$—, —C(=O)—, —C(=O)O—, —NHCO—, NHC(=O)NH—, —$CHR^g$—, —$CR^g_2$—, —NH— or —$NR^g$—, wherein $R^g$ is as defined in $R^g$ in the above formula (VI). The ketal compound or acetal compound may be a thioketal compound or thioacetal compound having sulfur atoms in place of the oxygen atoms that bond to $R^{23}$ and/or $R^{24}$ in the above formula (XXXVI).

The ketal compound and the acetal compound can be obtained by reacting the carbonyl compound with alcohol. The reaction can be considered as a reaction of protecting a carbonyl group contributing to radioactive ray sensitization action, and $R^{23}$ and $R^{24}$ in the above formula (XXXVI) may be referred to as a protecting group for the carbonyl group. In this case, a reaction by which the radiation-sensitive sensitizer generating agent (b) gives the radiation-sensitive sensitizer by the radioactive ray and the like may be referred to as a deprotection reaction. An example of reactivity (likelihood of the deprotection reaction) of the protecting group is shown below. The reactivity of the protecting group increases from left to right. For example, in the case of a methoxy group being used as the protecting group of the carbonyl group, the reactivity toward the deprotection reaction is high and the deprotection reaction under an acid catalyst tends to proceed even at normal temperature. The deprotection reaction proceeding at normal temperature has an advantage that blurring of an image can be prevented. On the other hand, if the deprotection reaction takes place in the patternwise unexposed regions and the radiation-sensitive sensitizer is generated upon the patternwise exposure, contrast of the resist may be deteriorated. In order to prevent generation of the radiation-sensitive sensitizer in the patternwise unexposed regions, the protecting group may be selected such that activation energy of the deprotection reaction increases (such that reactivity of the protecting group decreases). In light of decreasing reactivity of the protecting group, a cyclic protecting group in which $R^{23}$ and $R^{24}$ in the formula (XXXVI) bind with each other to form a ring structure is more preferred. Examples of the ring structure include a 6-membered ring and a 5-membered ring, and the 5-membered ring is preferred. In the case of using the protecting group of low reactivity, the resist material preferably contain a first trapping agent as described later, and it is desirable to bake the resist material film between the patternwise exposure and the floodwise exposure. In the baking, an unnecessary acid in the patternwise unexposed regions is neutralized by the trapping agent and contrast of a latent image can be increased. In addition, the baking can compensate reduction in reactivity of the protecting group, and can diffuse a substance to reduce roughness of a latent image of an acid in the resist material film.

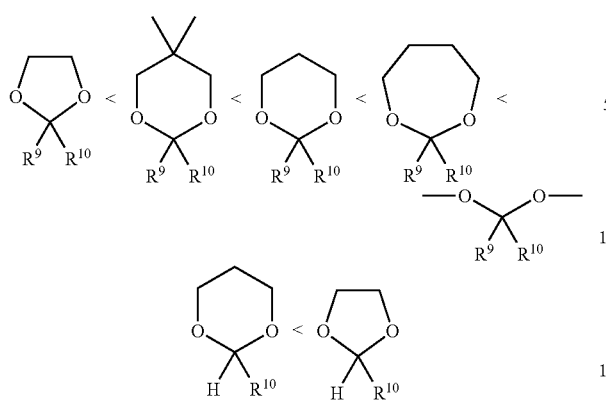

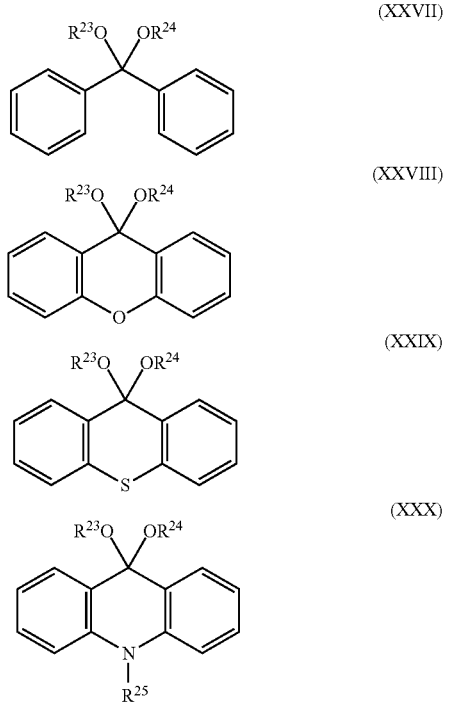

The ketal type radiation-sensitive sensitizer generating agent (b) may also be compounds represented by the following formulae (XXVII) to (XXX).

In the formulae (XXVII) to (XXX), $R^{23}$ and $R^{24}$ are respectively as defined in $R^{23}$ and $R^{24}$ in the formula (XXXVI). In the formulae (XXVII) to (XXX), a hydrogen atom in the aromatic ring may be substituted with an alkoxy group having 1 to 5 carbon atoms or an alkyl group having 1 to 5 carbon atoms, or the aromatic ring may be fused with another aromatic ring to form a naphthalene ring or an anthracene ring. $R^{25}$ represents an alkyl group having 1 to 5 carbon atoms. In the case of using a compound represented by the above formulae (XXVII) to (XXX) as the radiation-sensitive sensitizer generating agent (b), greater shift of radioactive ray absorption wavelength is realized upon transformation from the radiation-sensitive sensitizer generating agent (b) to the radiation-sensitive sensitizer, and more selective sensitization reaction may take place in the patternwise exposed regions.

It is to be noted that the ortho ester compound, in which a hydrogen atom in the hydroxyl group in the formula (VI) is substituted, is preferably a compound represented by the following formula (XLVI). In other words, the radiation-sensitive sensitizer generating agent (b) may also be a compound represented by the following formula (XLVI).

(XLVI)

In the formula (XLVI), $R^9$ is as defined in $R^9$ in the above formula (VI). In the formula (XLVI), $R^{38}$ to $R^{40}$ each independently represent: a phenyl group; a halogen atom; a saturated or unsaturated linear, branched or cyclic hydrocarbon group (preferably alkyl group) having 1 to 30 carbon atoms (preferably having 1 to 5 carbon atoms); or a phenyl group substituted with a linear, branched (chain) or cyclic saturated or unsaturated hydrocarbon group (preferably alkyl group) having 1 to 30 carbon atoms (preferably having 1 to 5 carbon atoms), an alkoxy group having 1 to 5 carbon atoms, or a hydroxyl group. $R^{38}$ to $R^{40}$ may form a ring structure via a single bond or a double bond, or via a bond including —$CH_2$—, —O—, —S—, —$SO_2$—, —$SO_2NH$—, —C(=O)—, —C(=O)O—, —NHCO—, —NHC(=O)NH—, —$CHR^g$—, —$CR^g{}_2$—, —NH— or —$NR^g$—. $R^g$ is as defined in $R^g$ in the above formula (VI).

The ortho ester compound degrades in the deprotection reaction upon the patternwise exposure, to transform into carboxylic acid ester or carboxylic acid containing for example a carbonyl group. The ortho ester compound is preferably an OBO ester compound represented by the following formula (XLVII) in which a carboxyl group moiety in the radiation-sensitive sensitizer containing a carboxyl group is substituted (protected) by OBO (e.g., 4-methyl-2,6,7-trioxabicyclo[2.2.2]octan-1-yl). The radiation-sensitive sensitizer generating agent (b) in which the carboxyl group is protected by OBO generates carboxylic acid by an acid catalyst generated upon the patternwise exposure, shifts the absorption wavelength of the radioactive ray, thereby functioning as the radiation-sensitive sensitizer upon the floodwise exposure. As carboxylic acid is generated from the radiation-sensitive sensitizer generating agent (b), in the patternwise exposed regions, the polarity of the resist is altered, for example from non-polar to polar. Given this, the ortho ester compound also functions as a dissolution accelerator in the development step, contributing to improvement of resist contrast. The radiation-sensitive sensitizer generating agent (b) containing the OBO ester compound can generate the radiation-sensitive sensitizer and cause a polarity changing reaction simultaneously.

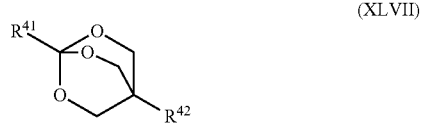

(XLVII)

In the formula (XLVII), $R^{41}$ and $R^{42}$ each independently represent a hydrogen atom; a phenyl group; a naphthyl group; an anthracenyl group; a phenoxy group; a naphthoxy group; an anthracenoxy group; an amino group; an amide group; a halogen atom; a saturated or unsaturated linear, branched or cyclic hydrocarbon group (preferably alkyl group) having 1 to 30 carbon atoms (preferably having 1 to 5 carbon atoms); a phenoxy group substituted with an alkoxy group having 1 to 5 carbon atoms, a hydroxyl group, an amino group, an amide group, or an alkyl group having 1 to 5 carbon atoms; a phenyl group substituted with a saturated or unsaturated linear, branched or cyclic hydrocarbon group (preferably alkyl group) having 1 to 30 carbon atoms (preferably having 1 to 5 carbon atoms), an alkoxy group having 1 to 5 carbon atoms, an amino group, an amide group, or a hydroxyl group; a naphthoxy group substituted with an alkoxy group having 1 to 5 carbon atoms, an alkyl group having 1 to 5 carbon atoms, or a hydroxyl group; an anthracenoxy group substituted with an alkoxy group having 1 to 5 carbon atoms, an alkyl group having 1 to 5 carbon atoms, an amino group, an amide group, or a hydroxyl group; a saturated or unsaturated linear, branched or cyclic hydrocarbon group (preferably alkyl group) having 1 to 30 carbon atoms (preferably having 1 to 5 carbon atoms) substituted with an alkoxy group having 1 to 5 carbon atoms, a phenoxy group, a naphthoxy group, an anthracenoxy group, an amino group, an amide group, or a hydroxyl group; or a carbonyl group to which an alkyl group having 1 to 12 carbon atoms bonds. $R^{41}$ and $R^{42}$ each independently represent: preferably a hydrogen atom; a phenyl group; a phenoxy group; a phenoxy group substituted with an alkoxy group having 1 to 5 carbon atoms, a hydroxyl group, or an alkyl group having 1 to 5 carbon atoms; or a phenyl group substituted with an alkoxy group having 1 to 5 carbon atoms, or a hydroxyl group.

Examples of the radiation-sensitive sensitizer generating agent (b) include the compounds represented by the following formulae. These compounds are alcohol compounds in which a hydrogen atom in an alcoholic hydroxyl group is not substituted, and transform into ketone compounds by a reaction upon the patternwise exposure.

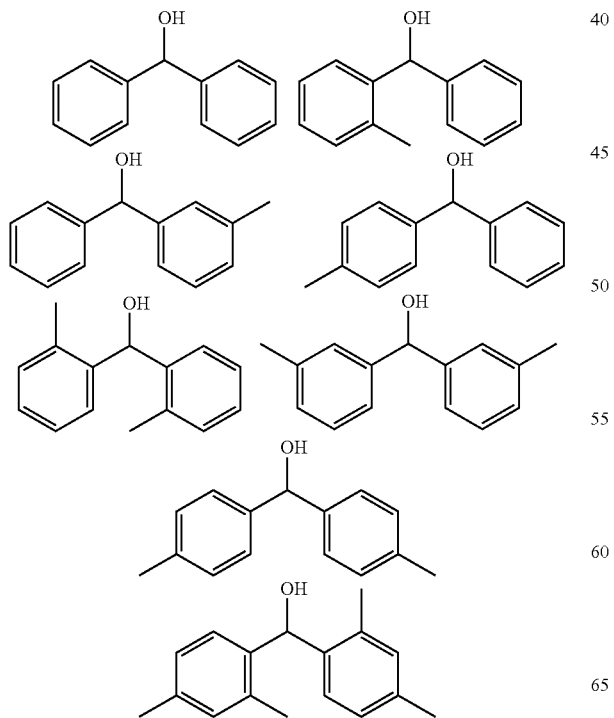

-continued

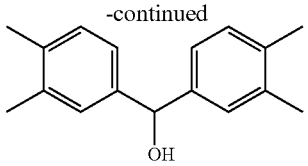

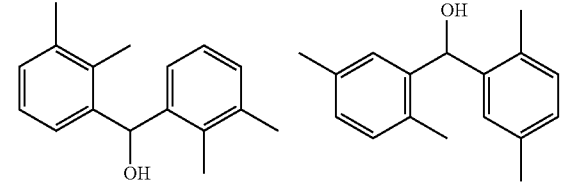

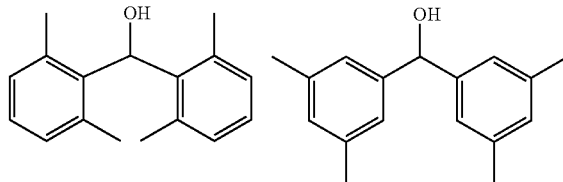

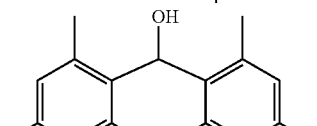

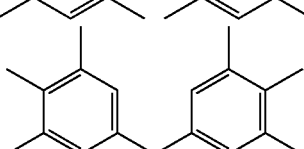

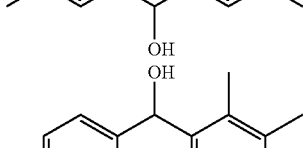

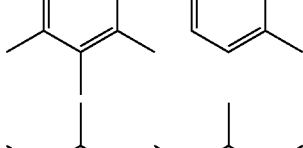

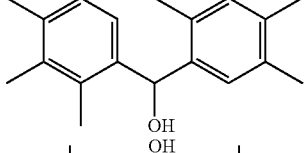

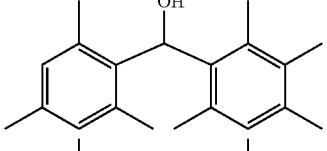

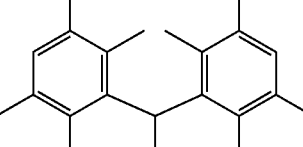

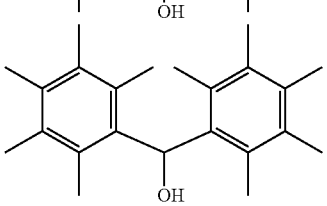

-continued
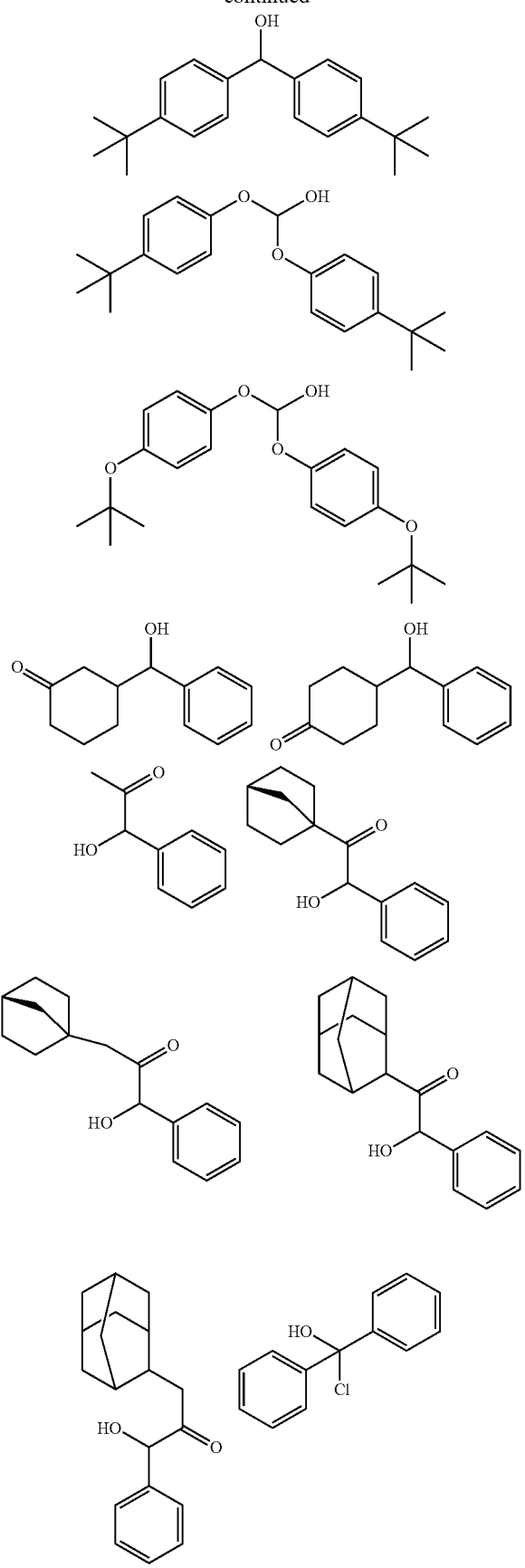
-continued
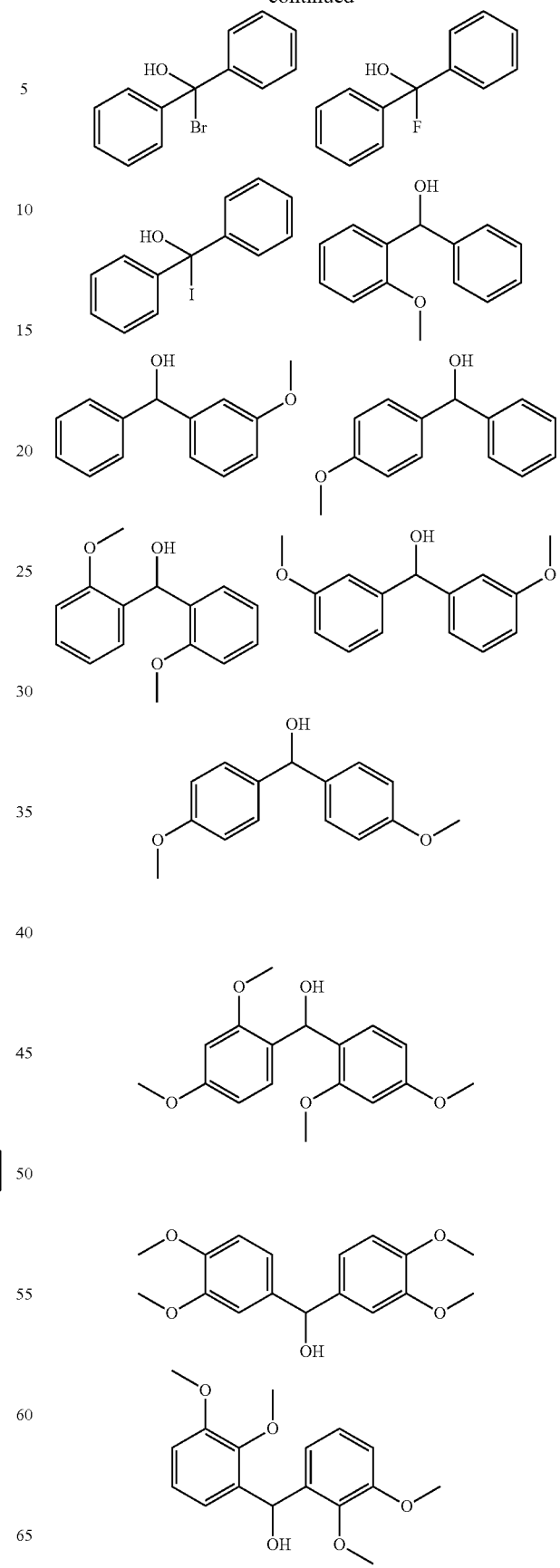

-continued
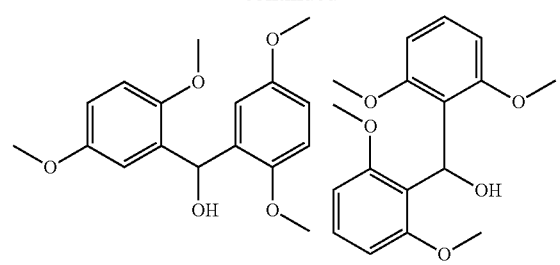
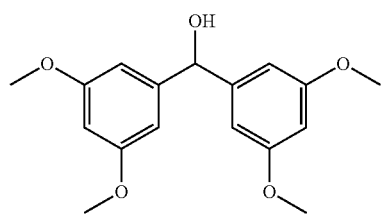
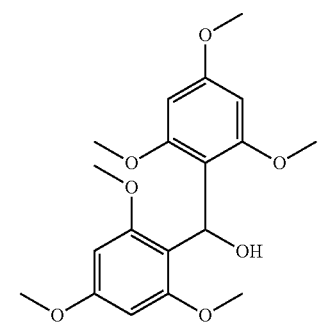
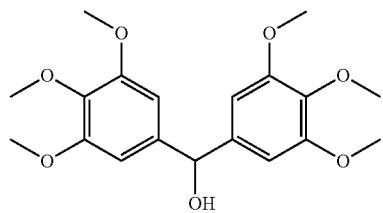
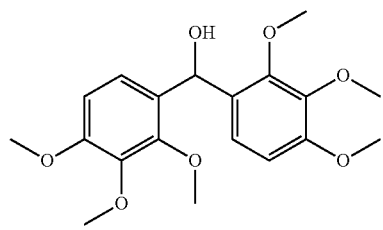
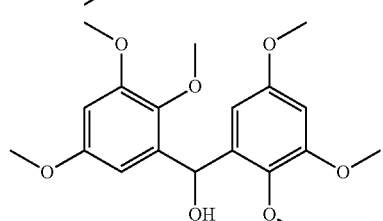
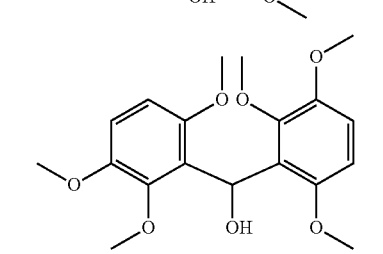
-continued
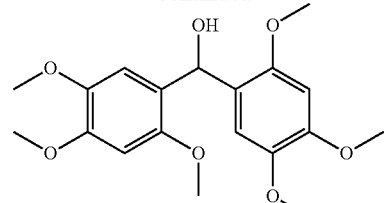
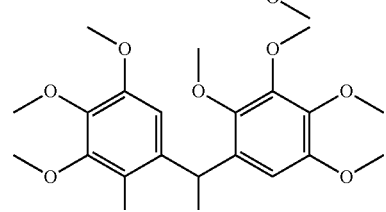
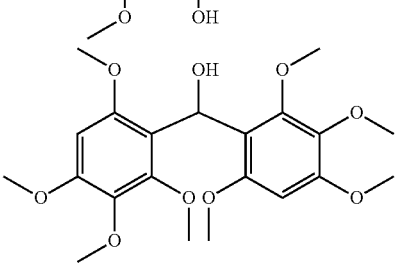
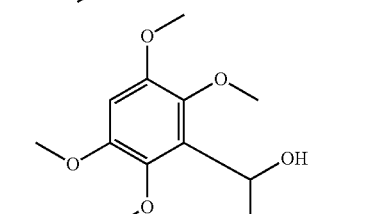
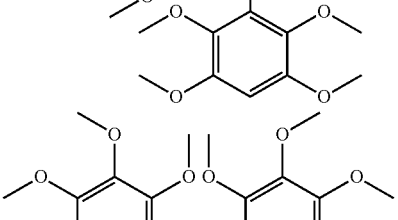
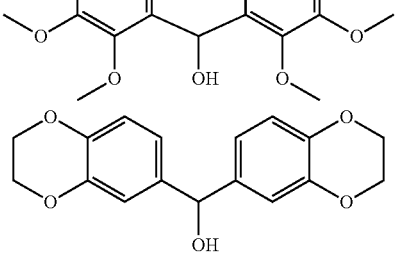
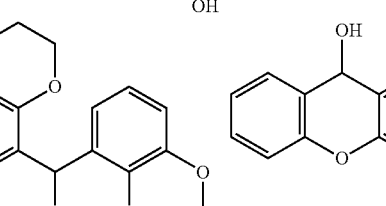
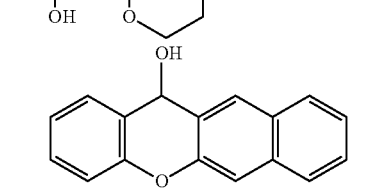

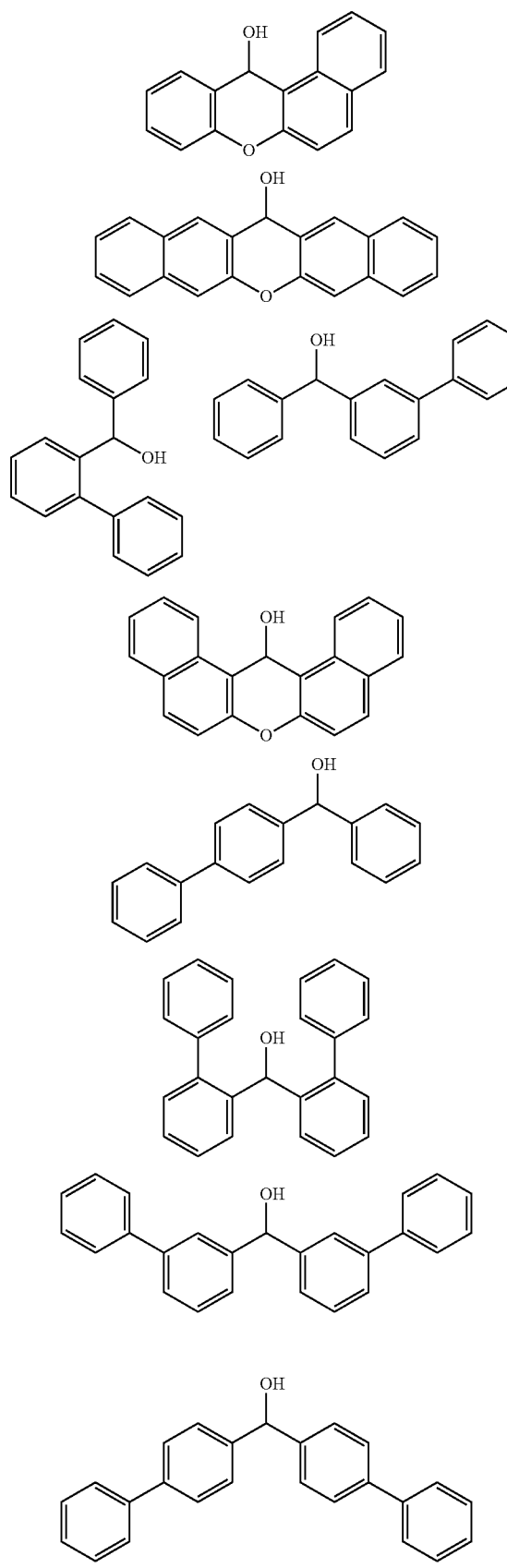
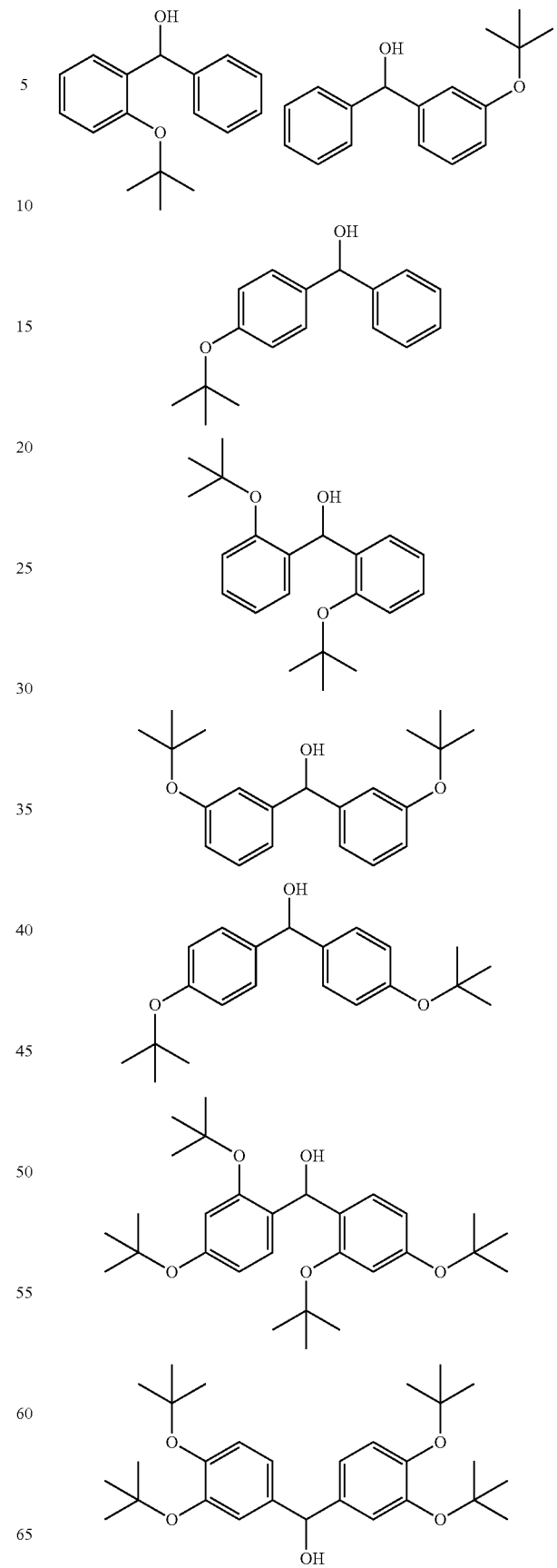

69
-continued
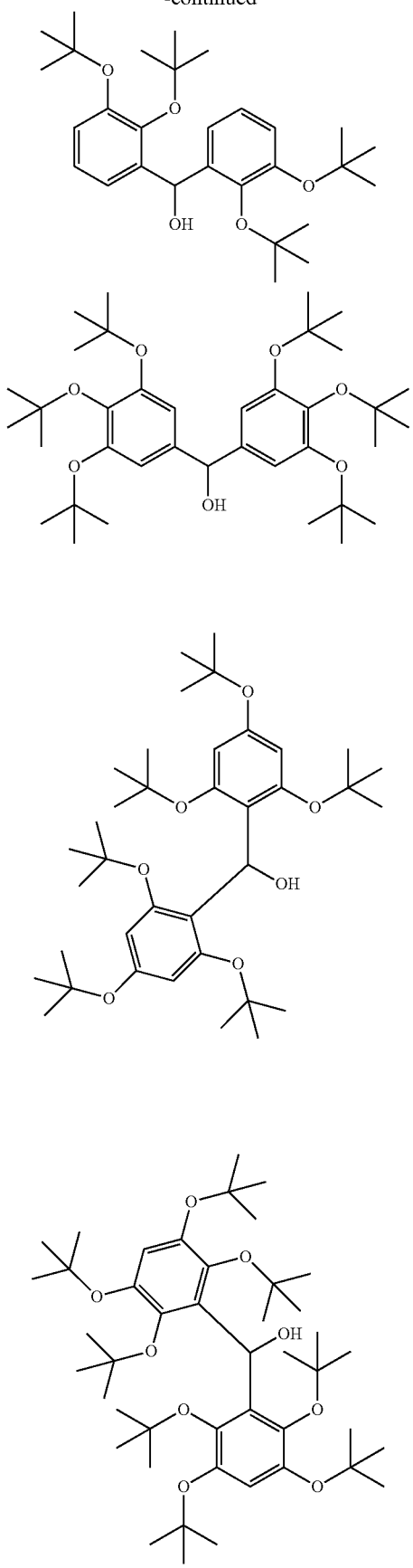
70
-continued
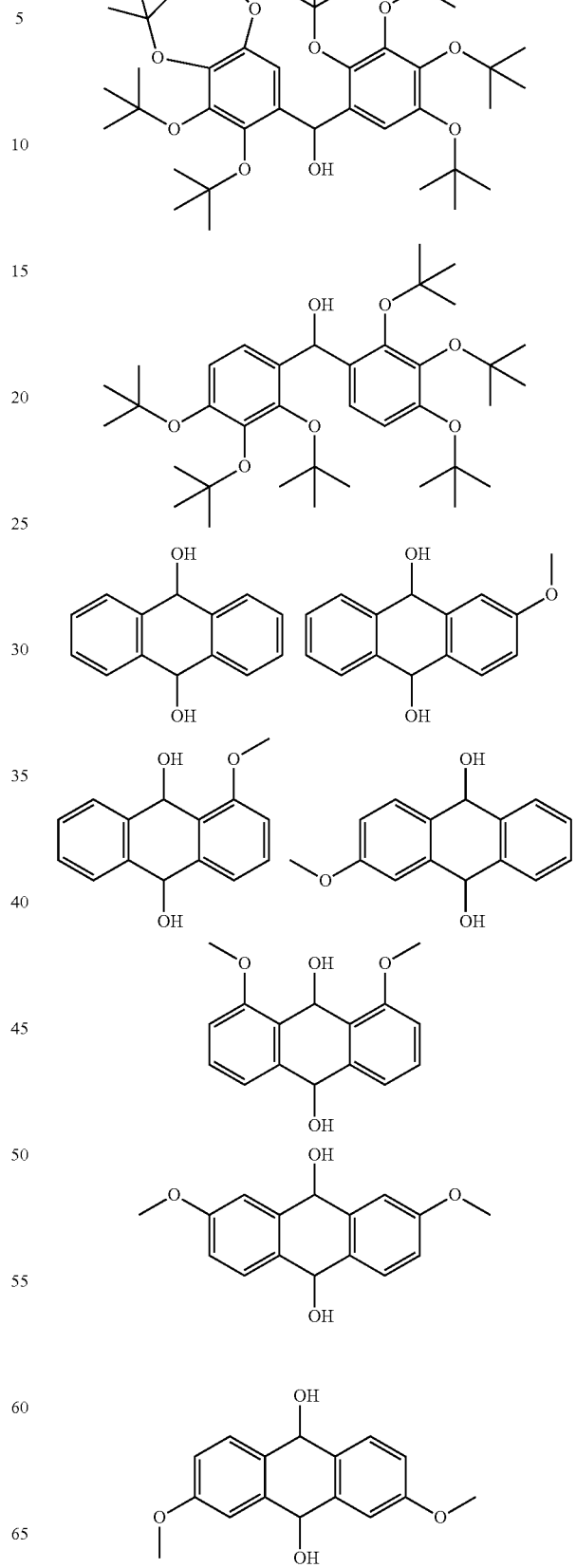

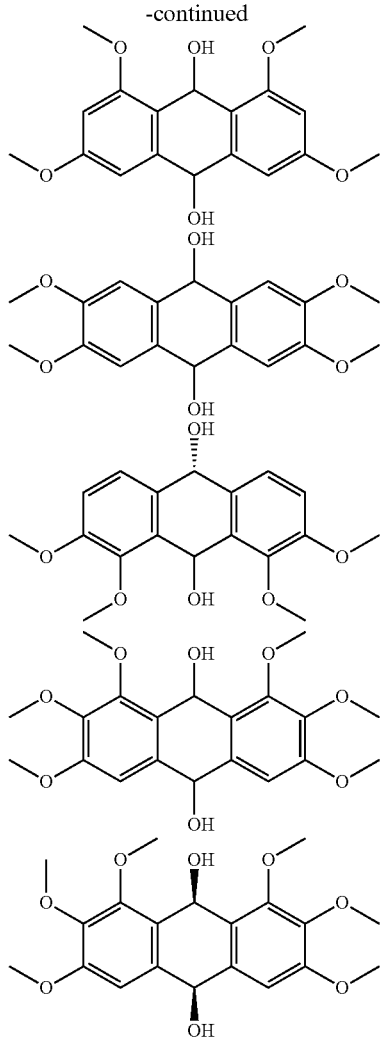
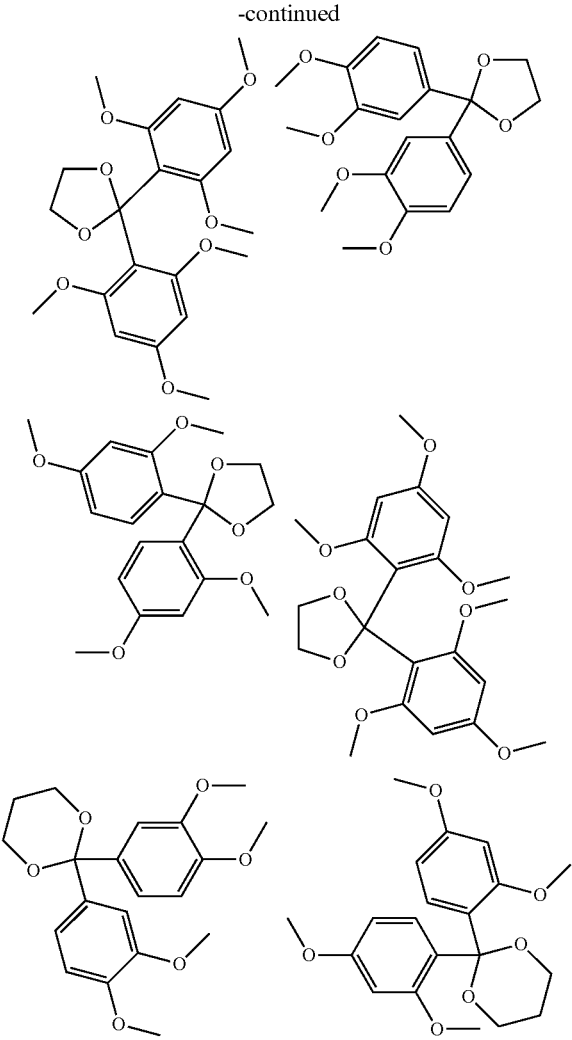
The following compounds are examples of the ketal compound or the acetal compound in which a carbonyl group in the radiation-sensitive sensitizer is protected. These compounds transform into radiation-sensitive sensitizer containing ketone in the patternwise exposed regions, under a catalytic action of an acid generated upon the patternwise exposure.
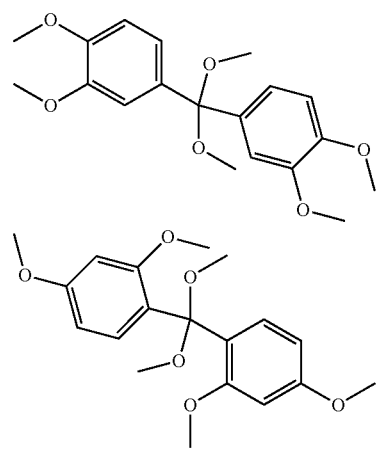
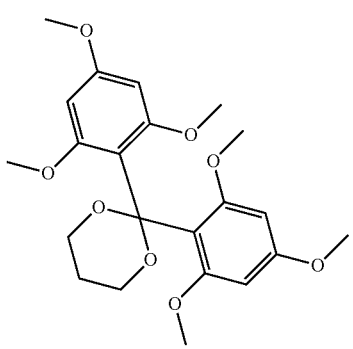
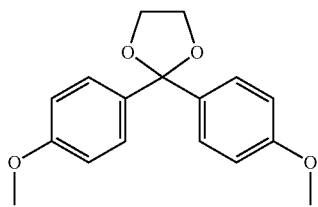

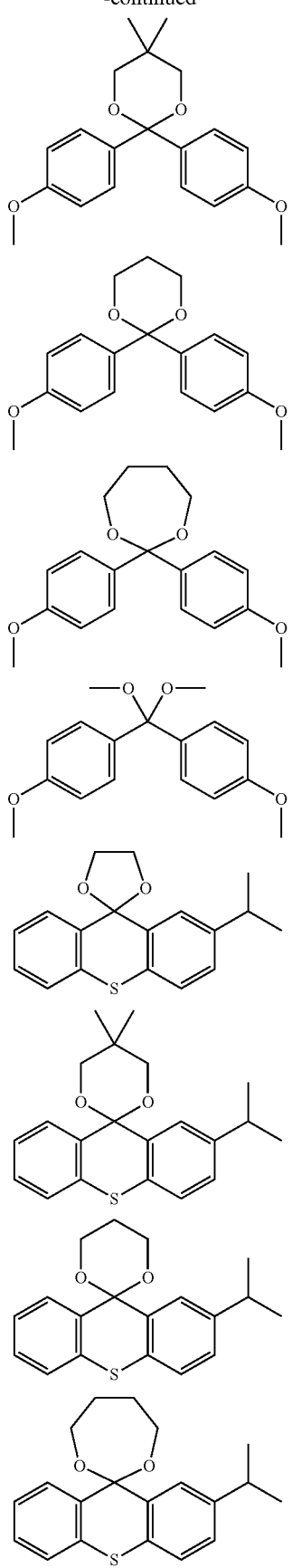
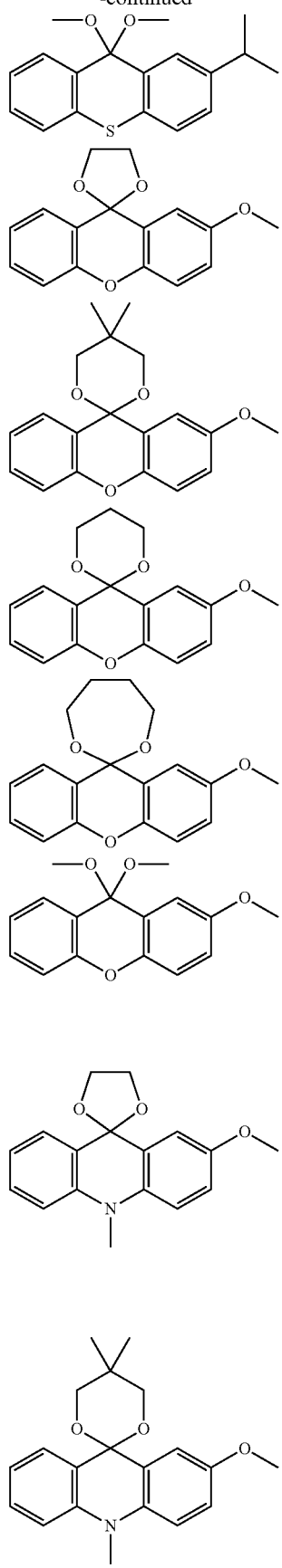

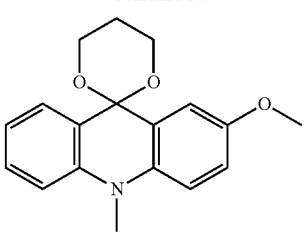
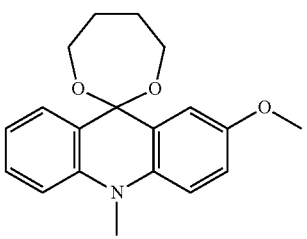
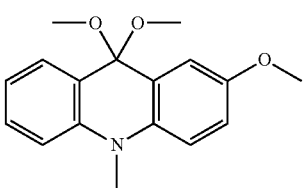
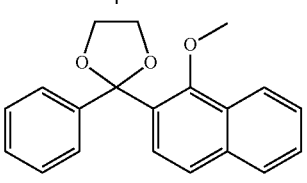
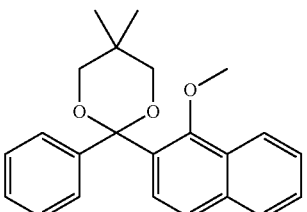
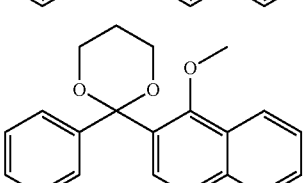
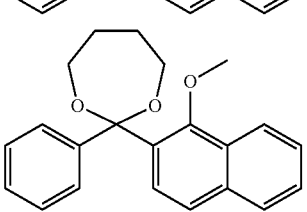
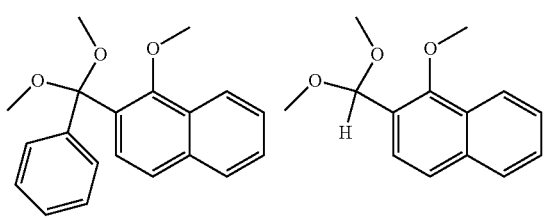
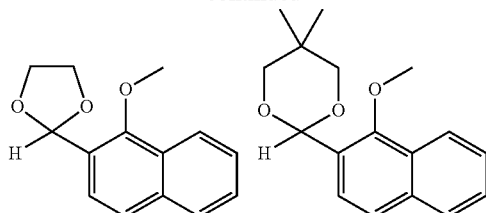
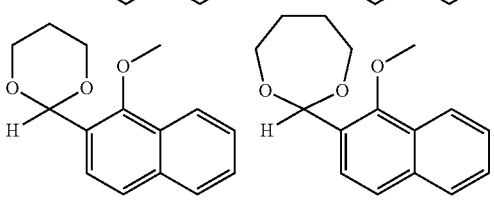
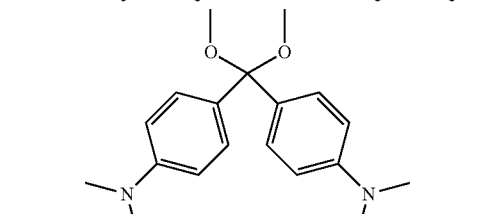
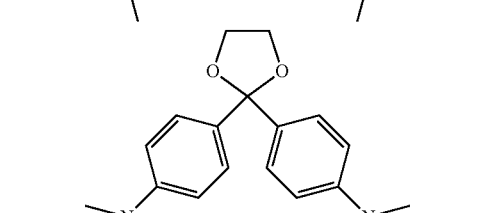
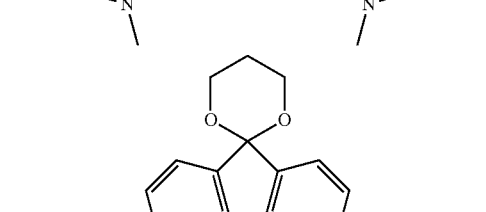
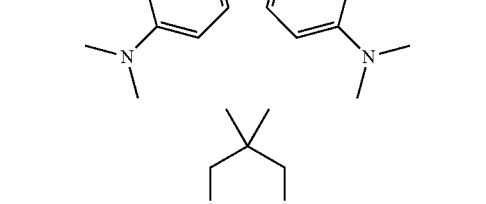
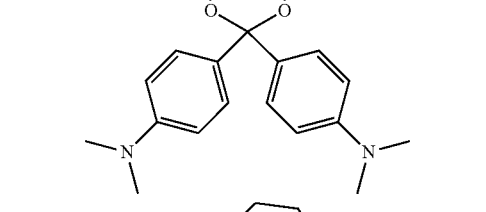
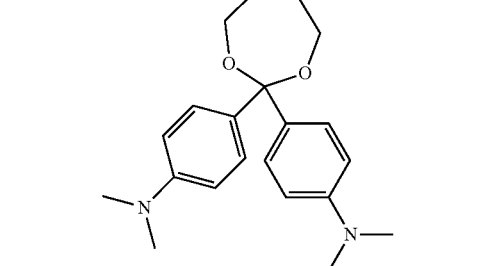

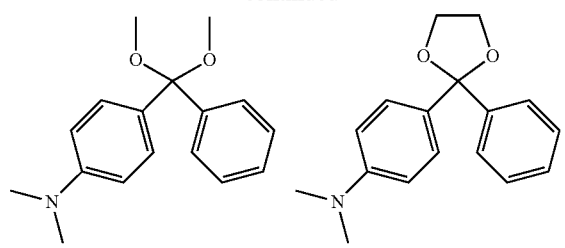
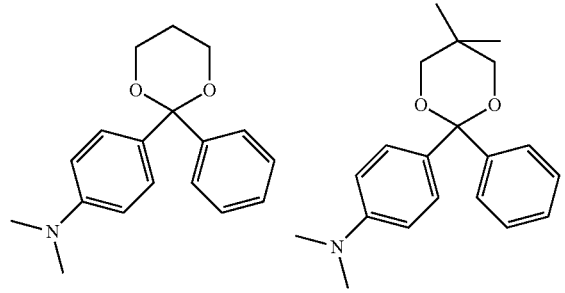
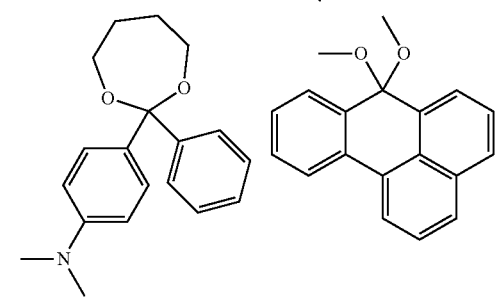
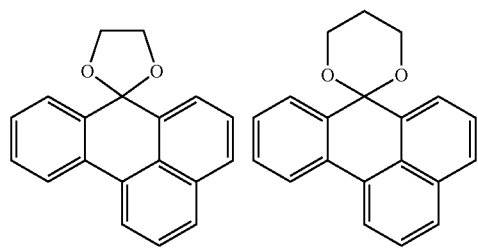
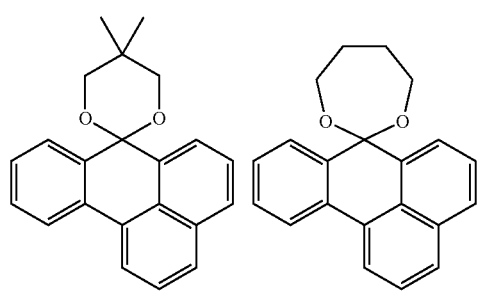
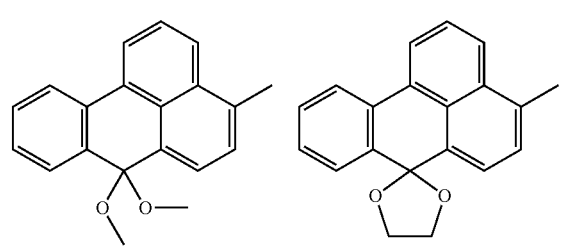
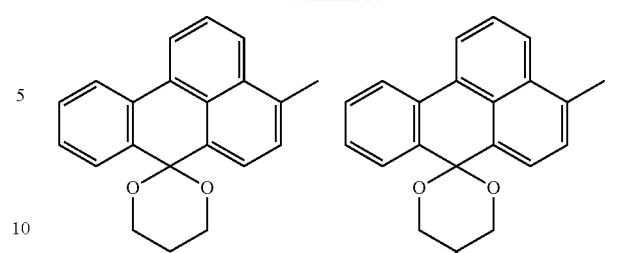
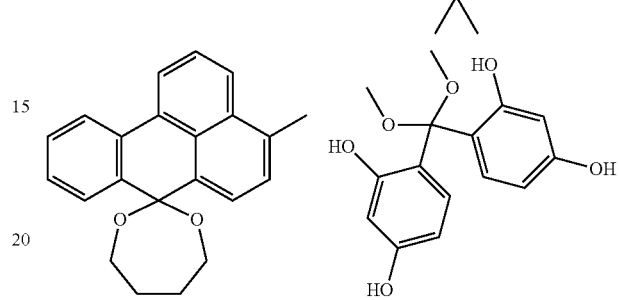
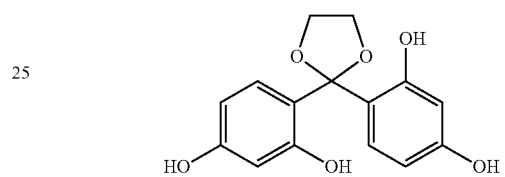
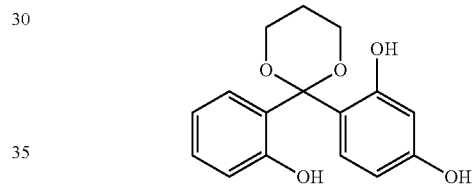
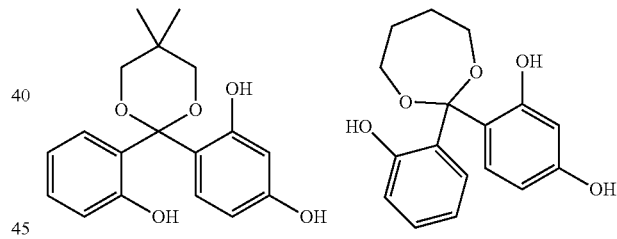
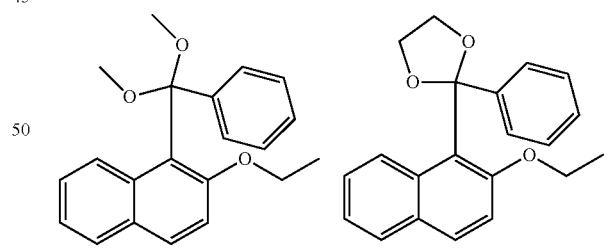
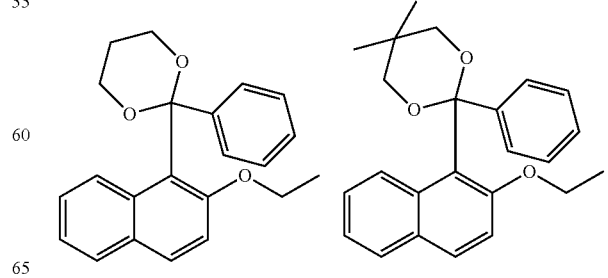

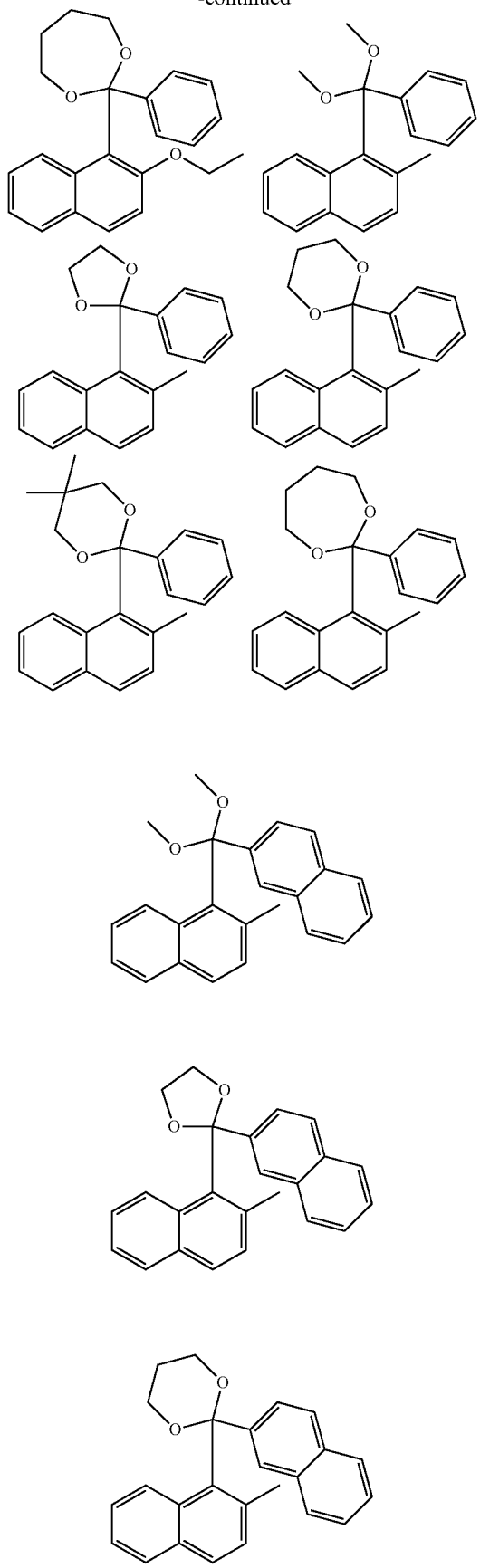
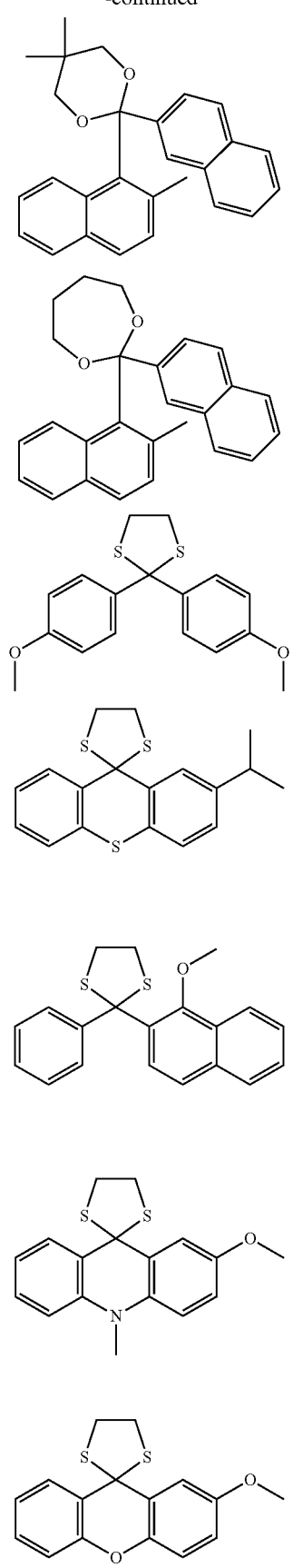

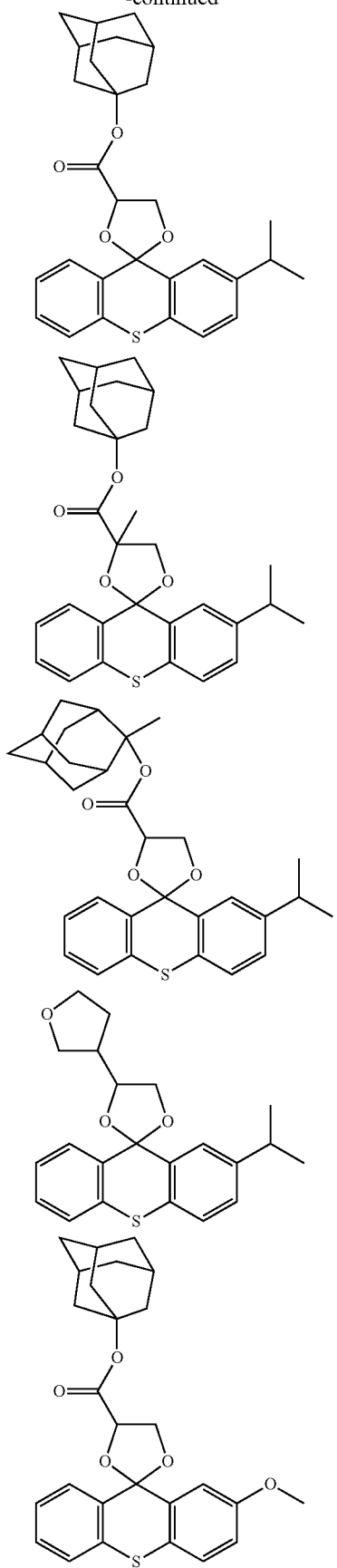
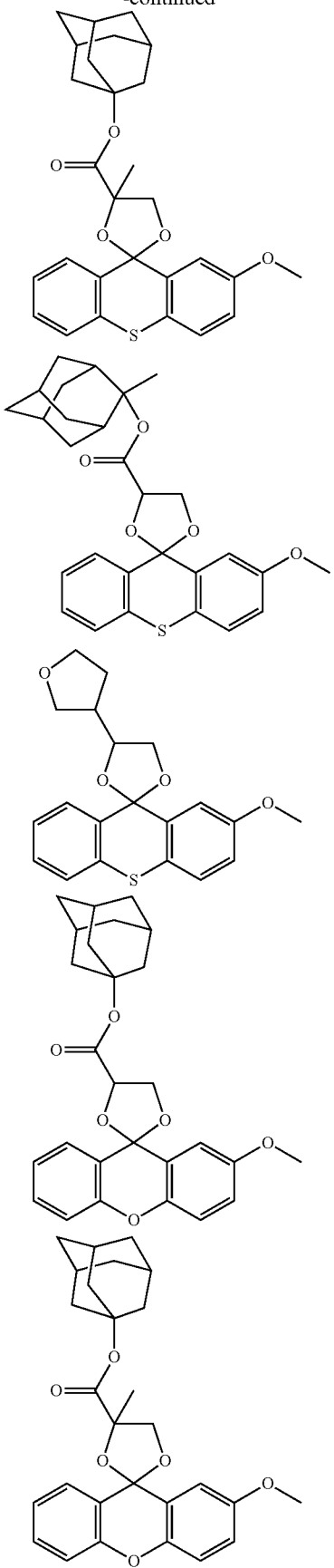

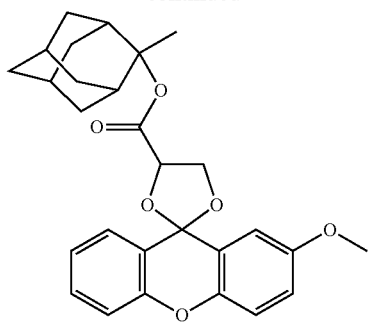
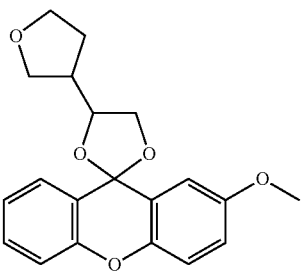
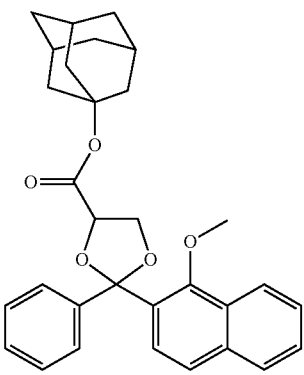
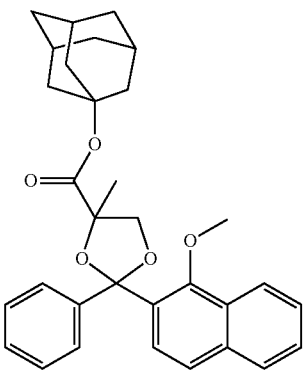
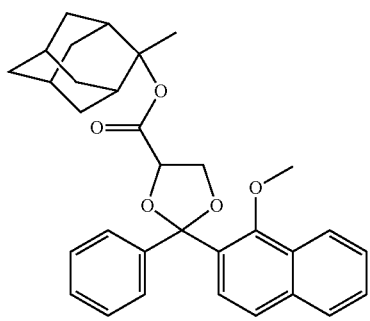
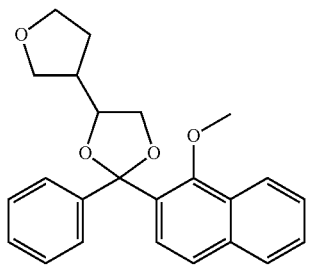
The following compounds are examples of the ortho ester compound containing a carbon atom substituted with 3 alkoxy groups.
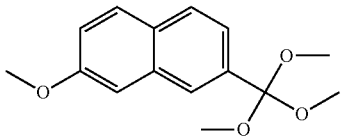
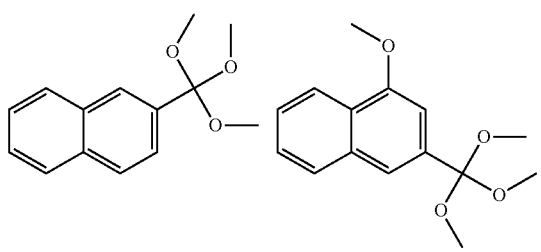
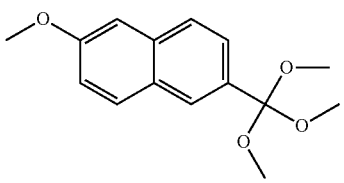
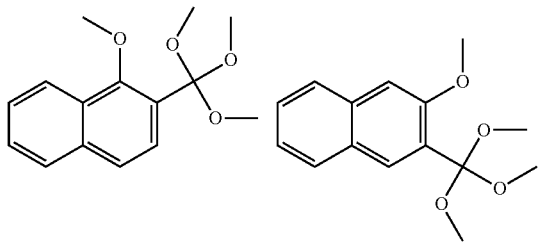
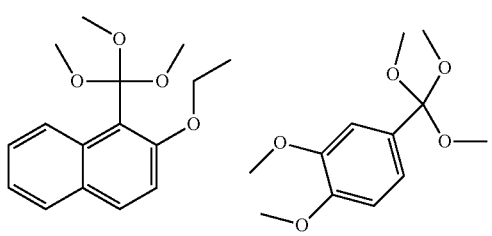
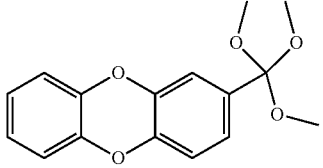

-continued
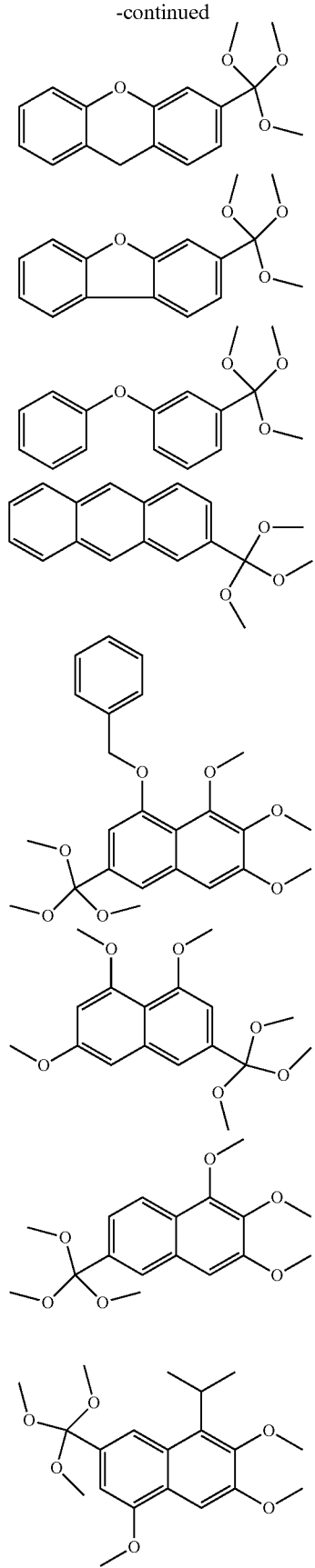
The ortho ester compound deprotects by the acid catalyst generated upon the patternwise exposure, to generate an ester containing a carbonyl group (in the following example, methyl carboxylate).
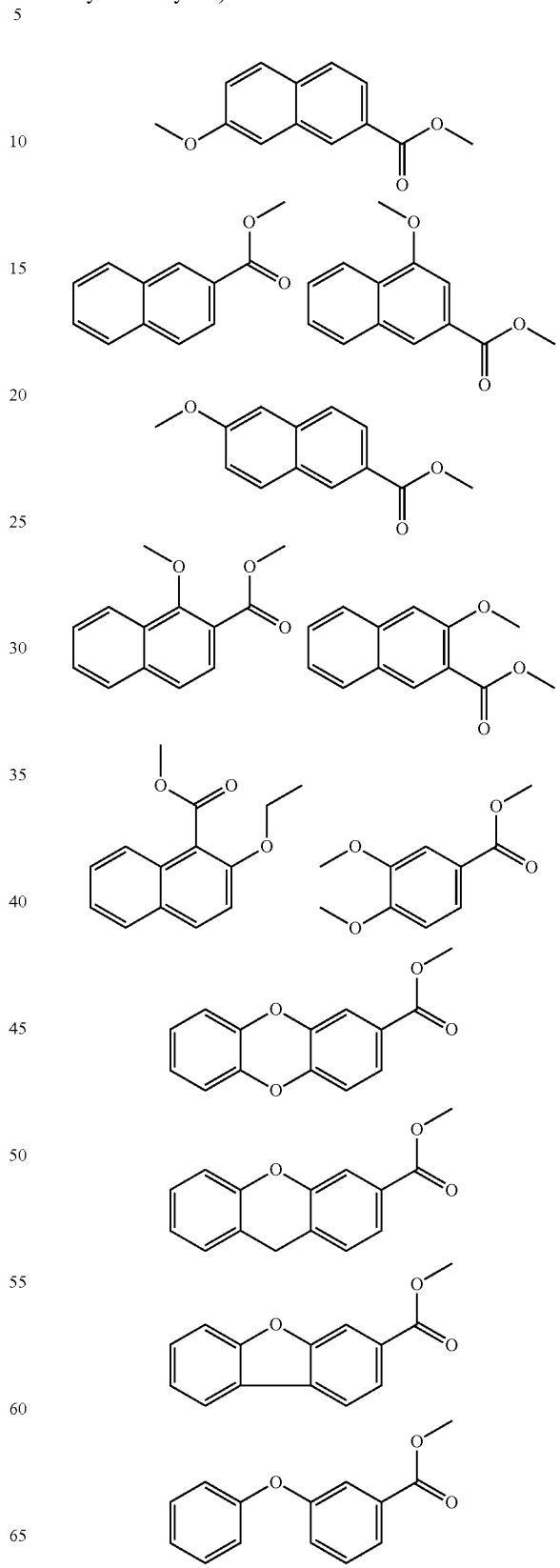

87
-continued
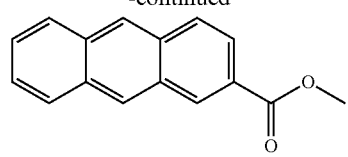
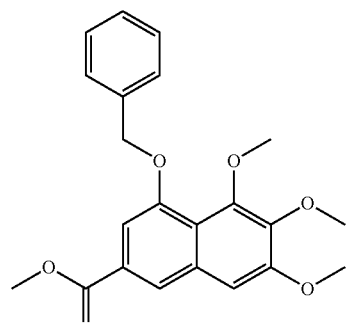
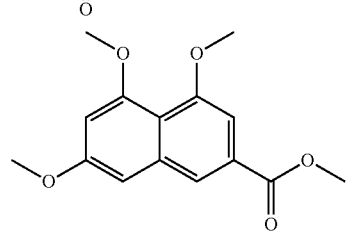
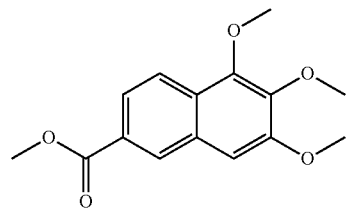
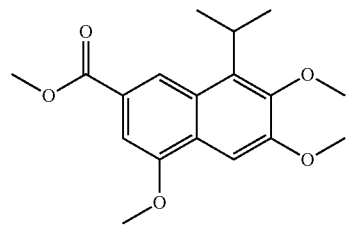
The following chemical formulae show examples of the OBO ester compound, which is a derivative in which a carboxyl group moiety of a carboxyl group-containing radiation-sensitive sensitizer is protected by OBO (e.g. 4-methyl-2,6,7-trioxabicyclo[2.2.2]octan-1-yl).
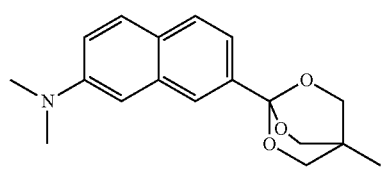
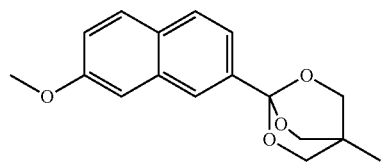
88
-continued
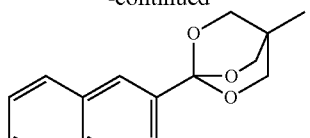
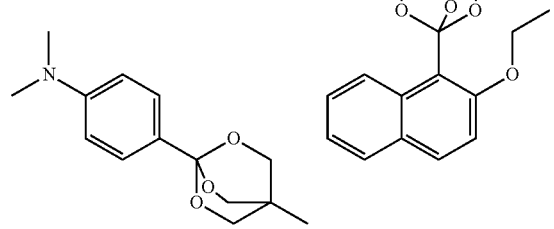
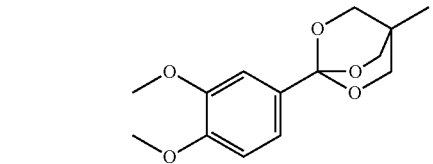
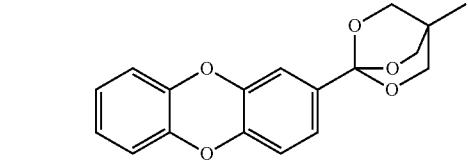

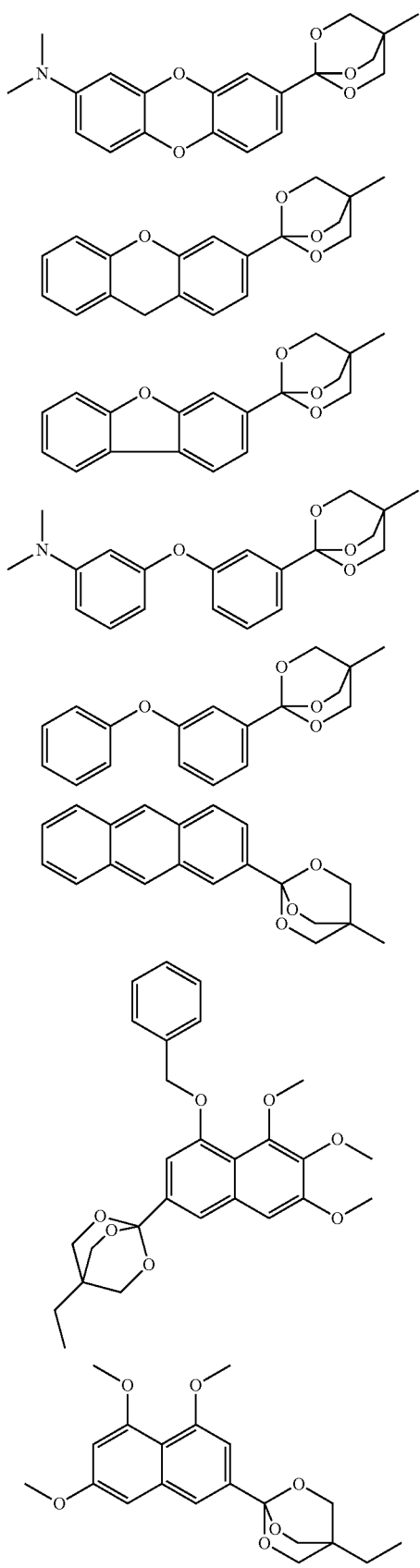
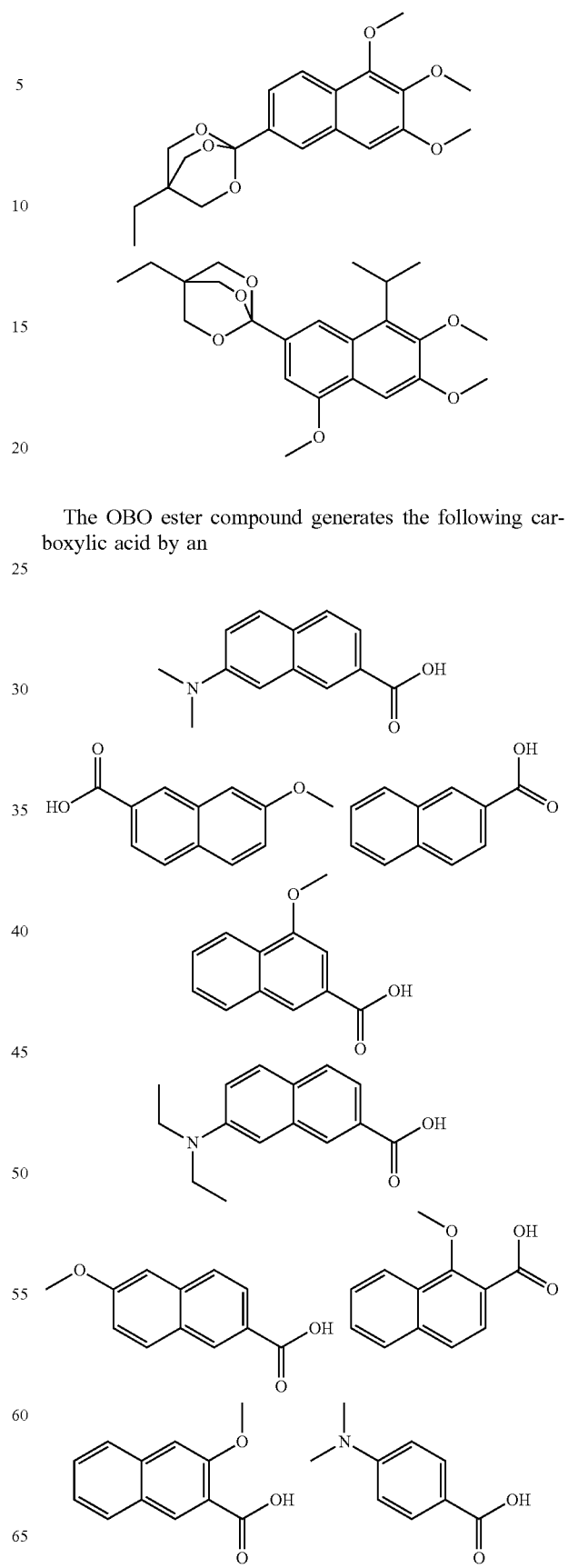
The OBO ester compound generates the following carboxylic acid by an -continued

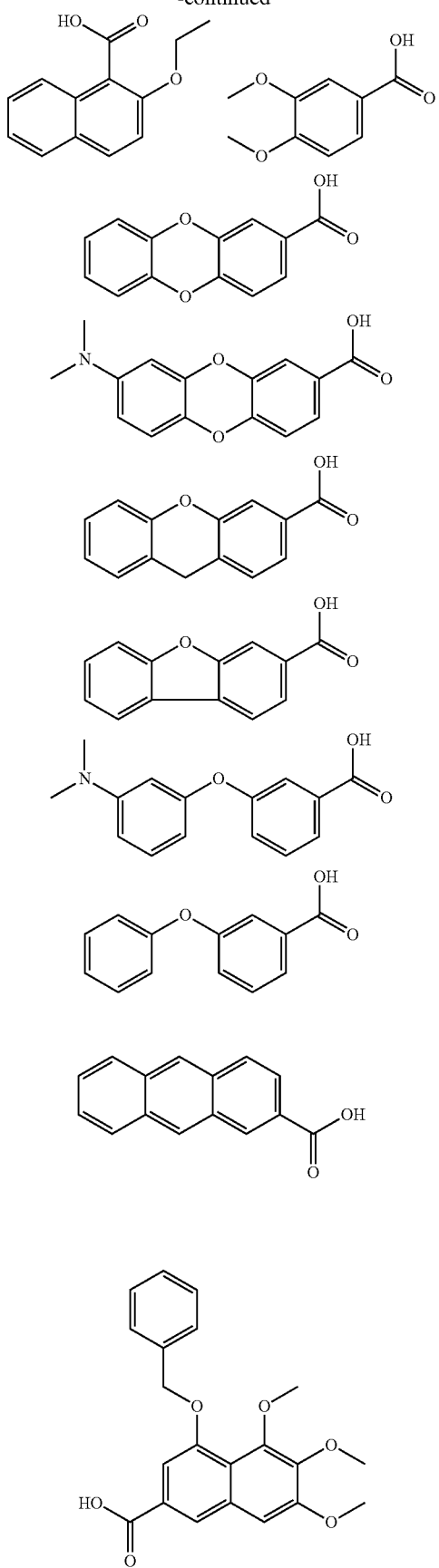

-continued

Examples of the radiation-sensitive sensitizer generated from the component (2) (i.e., the radiation-sensitive acid-and-sensitizer generating agent (a) and the radiation-sensitive sensitizer generating agent (b)) upon the exposure include chalcone, 1,2-diketone, benzoin, benzophenone, fluorene, naphthoquinone, anthraquinone, xanthene, thioxanthene, xanthone, thioxanthone, cyanine, merocyanine, naphthalocyanine, subphthalocyanine, pyrylium, thiopyrylium, tetraphylline, annulene, spiropyran, spirooxazine, thiospiropyran, oxole, azine, thiazine, oxazine, indoline, azulene, azulenium, squarylium, porphyrin, porphyrazine, triarylmethane, phthalocyanine, acridone, coumarin, ketocoumarin, quinolinone, benzoxazole, acridine, thiazine, benzothiazole, phenothiazine, benzotriazole, perylene, naphthalene, anthracene, phenanthrene, pyrene, naphthacene, pentacene, coronene, and derivatives of these, and the like. In addition, the radiation-sensitive sensitizer generated from the component (2) upon the exposure preferably contains a carbonyl compound. The carbonyl compound preferably contains ketone, aldehyde, carboxylic acid, ester, amide, enone, carboxylic acid chloride, carboxylic anhydride, and the like as a carbonyl group. As the carbonyl compound, in light of separating the wavelength of the radioactive ray for the floodwise exposure sufficiently from the wavelength of the radioactive ray for the patternwise exposure to thereby improve resist contrast, a compound that absorbs the radioactive ray on the long-wavelength side of greater than 250 nm is preferred. Examples of the carbonyl compound include: a benzophenone derivative, a xanthone derivative, a thioxanthone derivative, a coumarin derivative, and an acridone derivative. The carbonyl compound may also be a naphthalene derivative or an anthracene derivative, and may also be an acridone derivative. In the radiation-sensitive sensitizer, hydrogen in the aromatic ring is preferably substituted with an electron-donating group. Substitution of hydrogen in the aromatic ring of the radiation-sensitive sensitizer by an electron-donating group tends to improve electron transfer efficiency by the sensitization reaction upon the floodwise exposure, and improve sensitivity of the resist. In addition, a difference between the radioactive ray absorption wavelength of the radiation-sensitive sensitizer (b) and the radioactive ray absorption wavelength of the radiation-sensitive sensitizer can be made greater and the radiation-sensitive sensitizer can be excited more selectively upon the floodwise exposure, and contrast of the latent image of the acid in the resist material thus tends to be improved. Examples of the electron-donating group include: a hydroxyl group, a methoxy group, an alkoxy group, an amino group, an alkylamino group, and an alkyl group.

Examples of benzophenone and its derivatives include the following compounds.

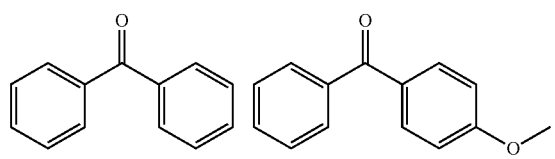
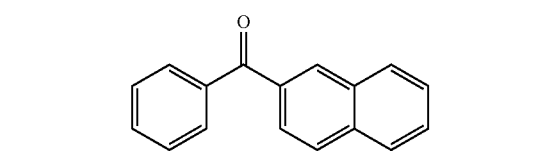
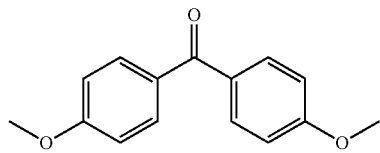
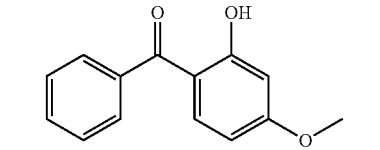
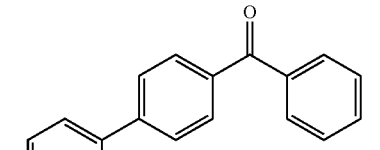
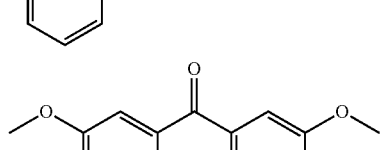
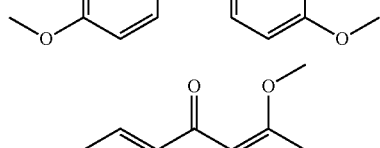
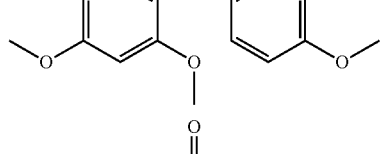
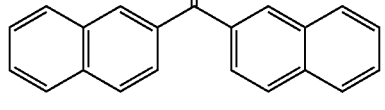

-continued

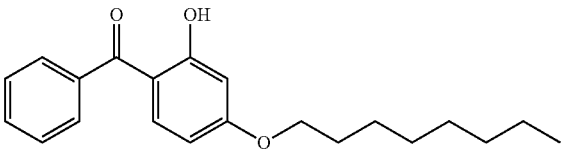
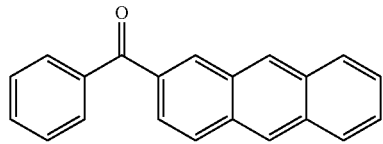
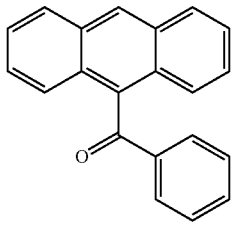
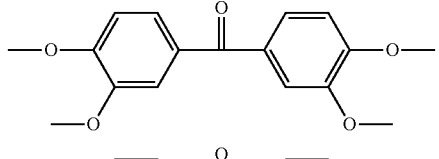
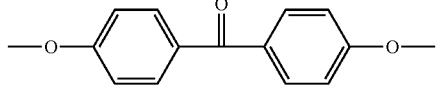
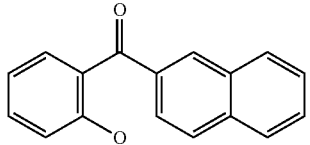
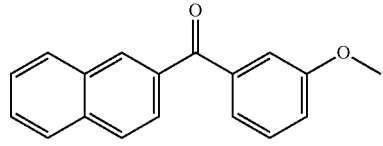
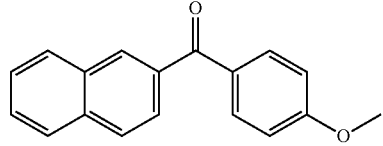
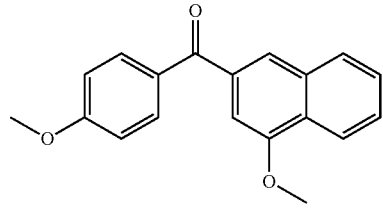
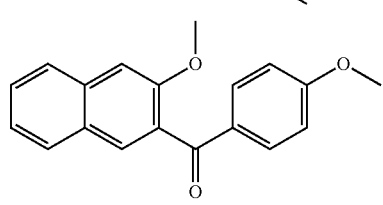

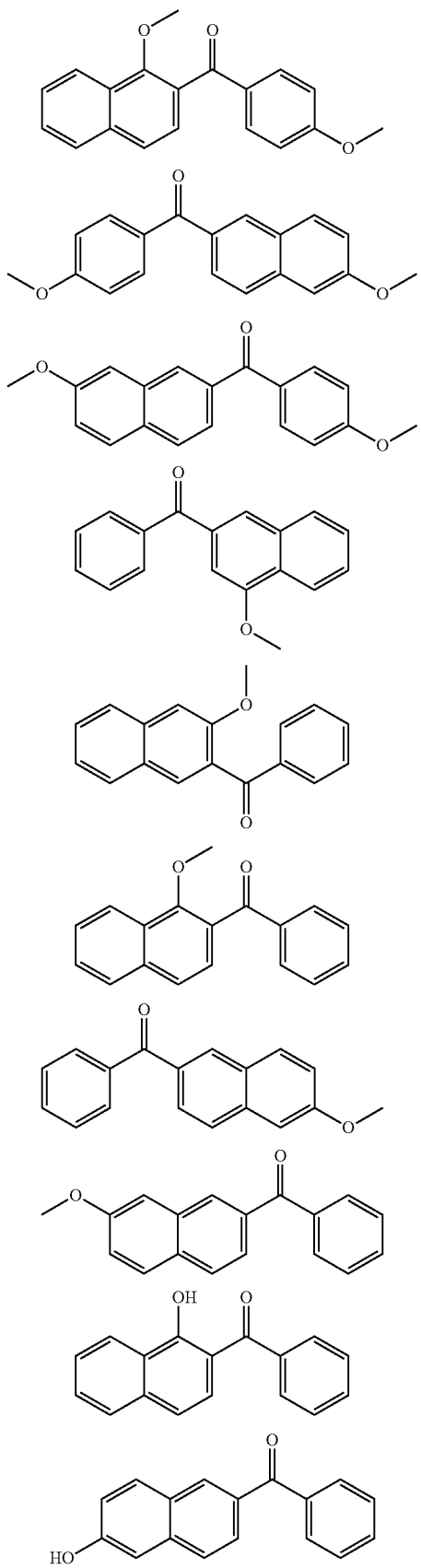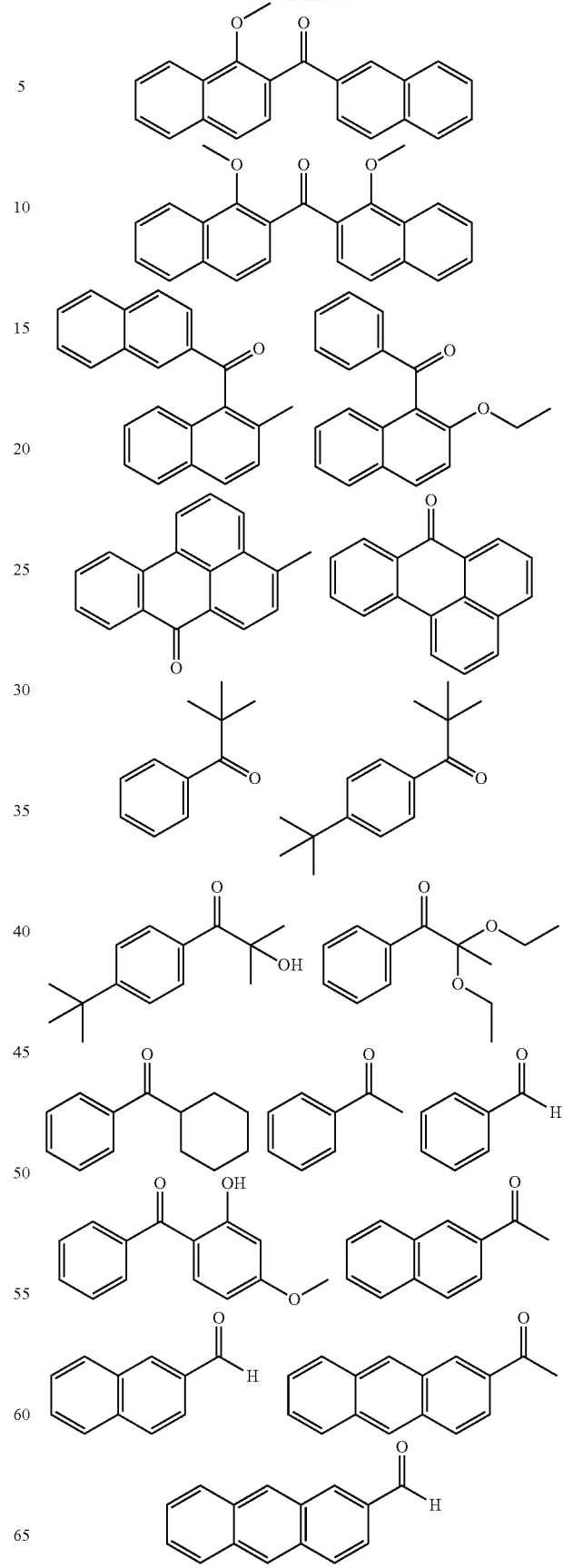

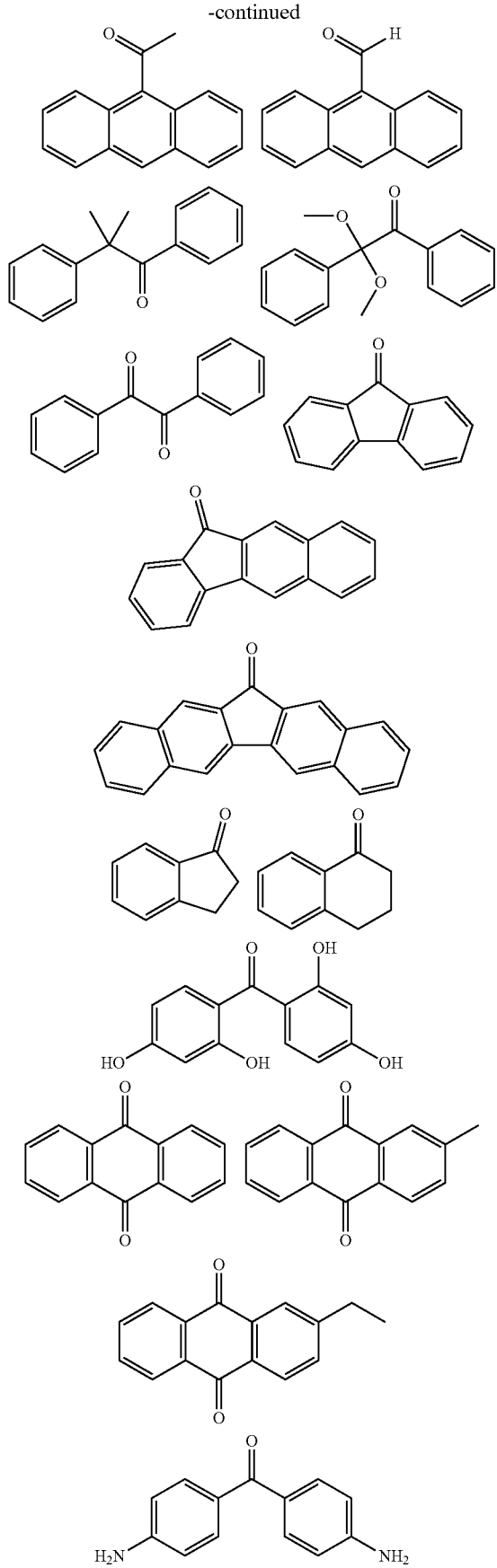
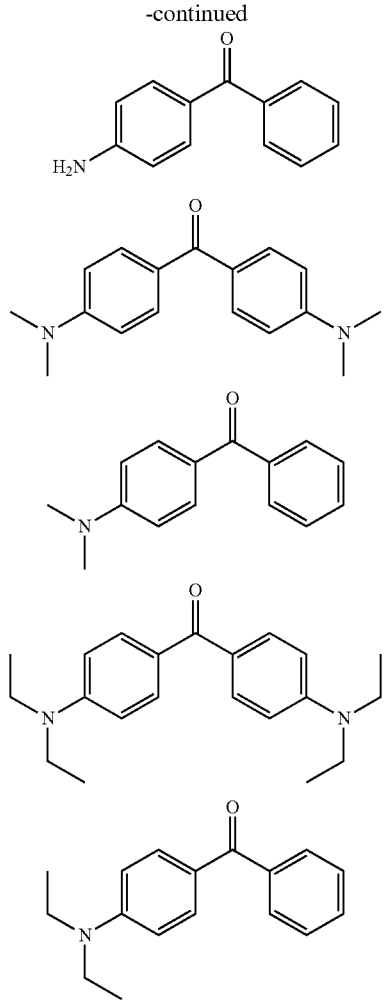
Examples of the thioxanthone and its derivatives include the following compounds.
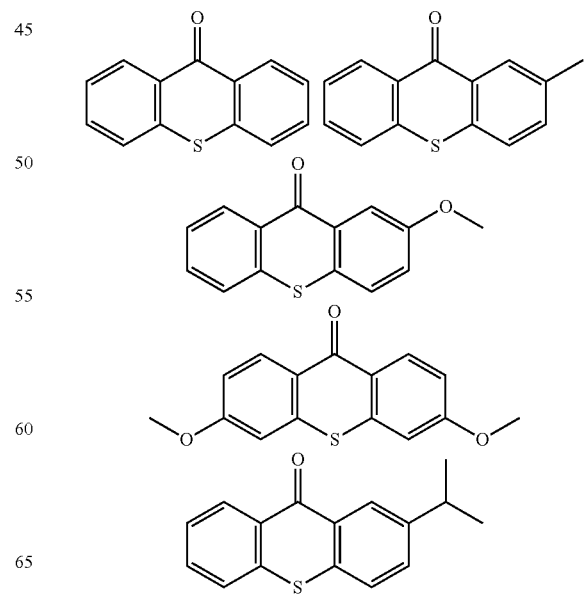

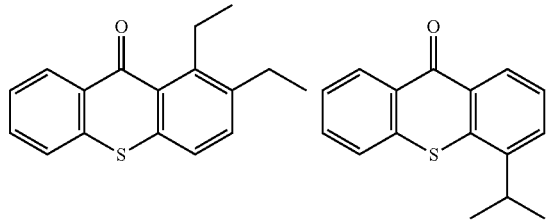
Examples of the xanthone and its derivatives include the following compounds.
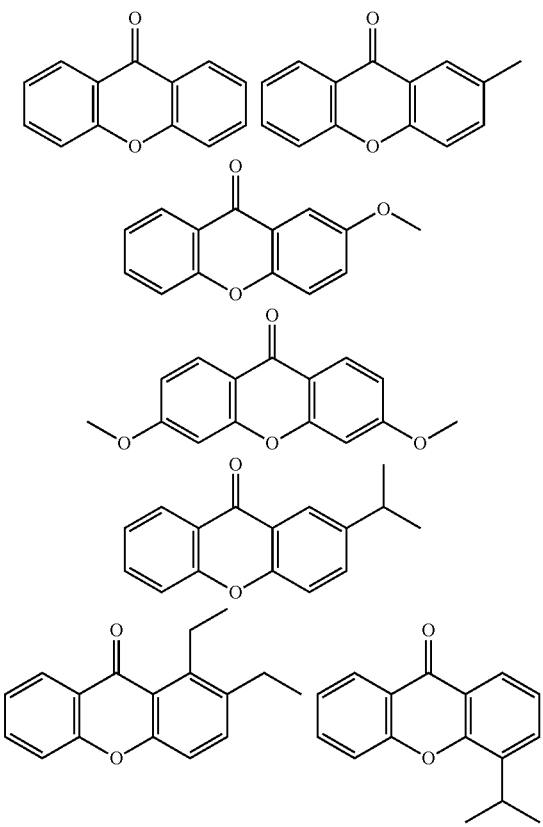
Examples of the acridone and its derivatives include the following compounds.
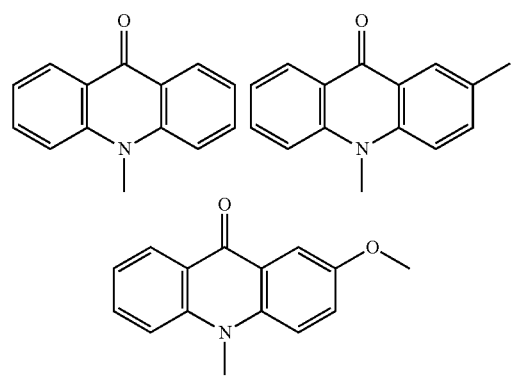
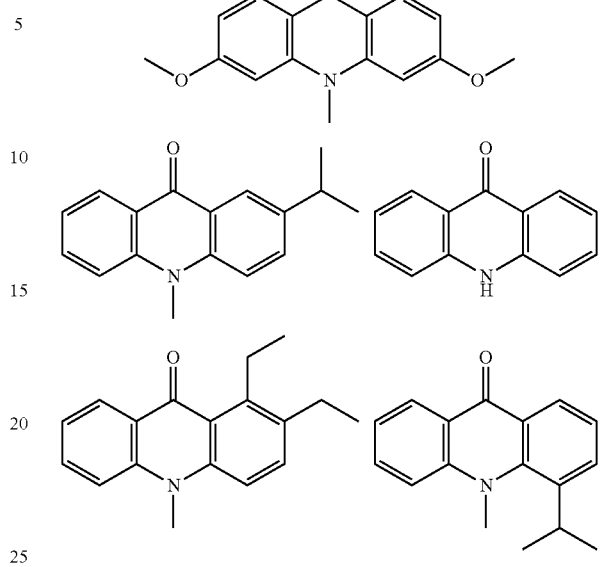
Examples of the coumarin and its derivatives include the following compounds.
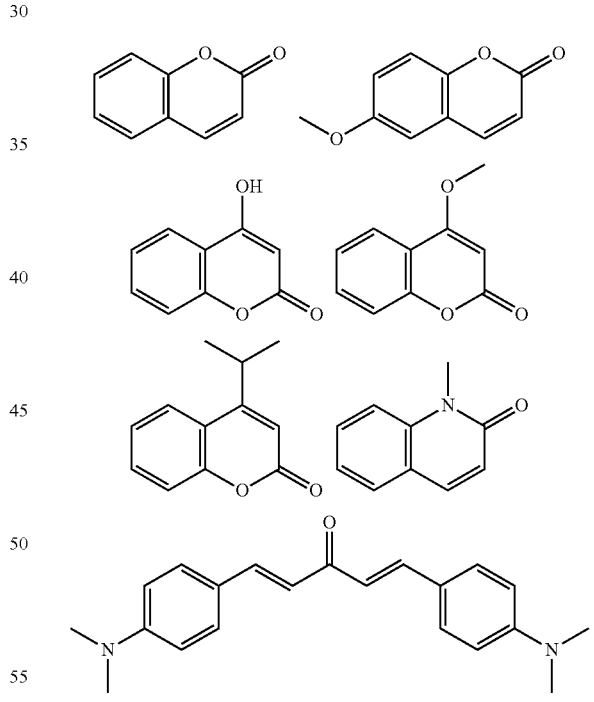
The radiation-sensitive sensitizer may also contain the following compounds.
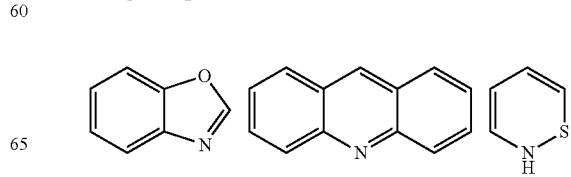

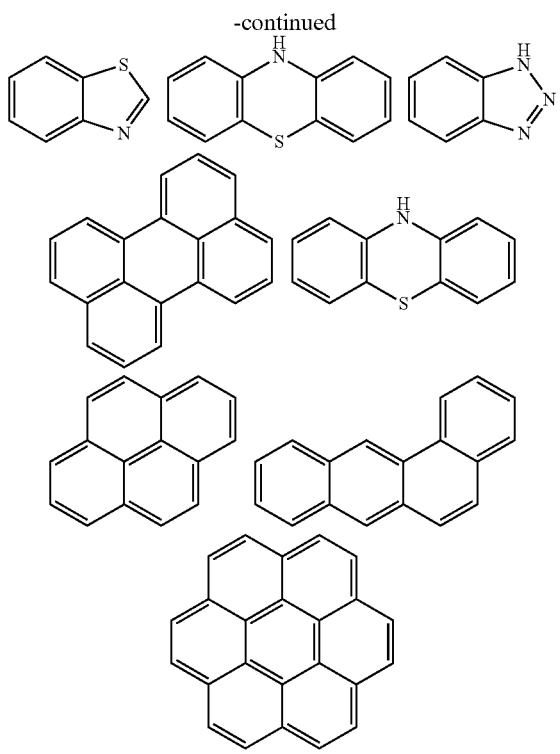

Examples of the radiation-sensitive sensitizer include acetophenone, 2,2-dimethoxy-2-phenylacetophenone, diethoxyacetophenone, 1-hydroxycyclohexyl phenyl ketone, 1,2-hydroxy-2-methyl-1-phenylpropan-1-one, α-hydroxycyclohexyl phenyl ketone, 2-hydroxy-2-methyl-1-phenylpropanone, 2-hydroxy-2-methyl-1-(4-isopropylphenyl)propanone, 2-hydroxy-2-methyl-1-(4-dodecylphenyl)propanone, 2-hydroxy-2-methyl-1-[(2-hydroxyethoxy)phenyl]propanone, benzophenone, 2-methylbenzophenone, 3-methylbenzophenone, 4-methylbenzophenone, 4-methoxybenzophenone, 2-chlorobenzophenone, 4-chlorobenzophenone, 4-bromobenzophenone, 2-carboxybenzophenone, 2-ethoxycarbonylbenzophenone, 4-benzoyl-4'-methyldiphenyl sulfide, benzophenonetetracarboxylic acid or the tetramethyl ester thereof, 4,4'-bis(dimethylamino) benzophenone, 4,4'-bis(dicyclohexylamino)benzophenone, 4,4'-bis(diethylamino)benzophenone, 4,4'-bis(dihydroxyethylamino)benzophenone, 4-methoxy-4'-dimethylaminobenzophenone, 4,4'-dimethoxybenzophenone, 4-dimethylaminobenzophenone, 4-dimethylaminoacetophenone, benzil, anthraquinone, 2-t-butylanthraquinone, 2-methylanthraquinone, phenanthraquinone, fluorenone, 2-benzyl-2-dimethylamino-1-(4-morpholinophenyl)-1-butanone, 2-(dimethylamino)-2-[(4-methylphenyl)methyl]-1-[4-(4-morpholinyl)phenyl]-1-butanone, 2-methyl-1-[4-(methylthio)phenyl]-2-morpholino-1-propanone, 2-hydroxy-2-methyl-[4-(1-methylvinyl)phenyl]propanol oligomer, benzoin, benzoin methyl ether, benzoin ethyl ether, benzoin propyl ether, benzoin isopropyl ether, benzoin isobutyl ether, benzoin phenyl ether, benzil dimethyl ketal, acridone, chloroacridone, N-methylacridone, N-butylacridone, N-butyl-chloroacridone, 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, bis-(2,6-dichloro benzoyl)phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, bis-(2,6-dimethoxybenzoyl)phenylphosphine oxide, bis-(2,6-dimethoxybenzoyl)-2,4,4-trimethylpentylphosphine oxide, bis-(2,6-dimethoxybenzoyl)-2,5-dimethylphenylphosphine oxide, bis-(2,4,6-trimethylbenzoyl)phenylphosphine oxide, (2,5,6-trimethylbenzoyl)-2,4,4-trimethylpentylphosphine oxide, 2-isopropylthioxanthone, 4-isopropylthioxanthone, 2,4-diethylthioxanthone, 2,4-dichlorothioxanthone, 1-chloro-4-propoxythioxanthone, benzoyl di-(2,6-dimethylphenyl)phosphonate, 1-[4-(phenylthio)phenyl]-1,2-octanedione-2-(O-benzoyloxime), 1-[9-ethyl-6-(2-methylbenzoyl)-9H-carbazol-3-yl]ethanone-1-(O-acetyloxime), 1-[9-ethyl-6-(2-methylbenzoyl)-9H-carbazol-3-yl]-3-cyclopentylpropanone-1-(O-acetyloxime), 1-[4-(phenylthio)phenyl]-3-cyclopentylpropane-1,2-dione-2-(O-benzoyloxime), 2,2-dimethoxy-1,2-diphenylethan-1-one, 1-[4-(2-hydroxyethoxy)-phenyl]-2-hydroxy-2-methyl-1-propan-1-one, 2-hydroxy-1-{4-[4-(2-hydroxy-2-methyl-propionyl)-benzyl]phenyl}-2-methyl-propan-1-one, phenylglyoxylic acid methyl ester, 2-methyl-1-(4-methylthiophenyl)-2-morpholinopropan-1-one, 2-benzyl-2-dimethylamino-1-(4-morpholinophenyl)-butanone-1, 1-[4-(phenylthio)phenyl]-1,2-octanedione 2-(O-benzoyloxime)], 1-[9-ethyl-6-(2-methylbenzoyl)-9H-carbazol-3-yl]ethanone 1-(O-acetyloxime), and the like.

The radiation-sensitive sensitizer generating agent (b) may be a part of the polymer constituting the polymer component (1). In this case, the radiation-sensitive sensitizer generating agent (b) is contained in the form of a group obtained by eliminating one hydrogen atom from the aforementioned compound and bound to the polymer.

In the case where the radiation-sensitive sensitizer generating agent (b) is the component different from the polymer component (1), the lower limit of the amount of the radiation-sensitive sensitizer generating agent (b) blended with respect to 100 parts by mass of the polymer component (1) is preferably 0.005 parts by mass, and more preferably 0.1 parts by mass. On the other hand, the upper limit of the amount of the radiation-sensitive sensitizer generating agent (b) blended is preferably 50 parts by mass, and more preferably 30 parts by mass.

In the case where the radiation-sensitive sensitizer generating agent (b) is a part of the polymer constituting the polymer component (1), the lower limit of the proportion of the radiation-sensitive sensitizer generating agent (b) contained with respect to 1 mol of the polymer component (1) is preferably 0.001 mol, more preferably 0.002 mol, and still more preferably 0.01 mol. On the other hand, the upper limit of the radiation-sensitive sensitizer generating agent (b) contained is preferably 0.95 mol, and more preferably 0.3 mol.

When the amount of the radiation-sensitive sensitizer generating agent (b) blended or the proportion of the radiation-sensitive sensitizer generating agent (b) contained is less than the lower limit, the sensitivity may be deteriorated. To the contrary, when the amount of the radiation-sensitive sensitizer generating agent (b) blended or the proportion of the radiation-sensitive sensitizer generating agent (b) contained is greater than the upper limit, it may be difficult to form the resist material film, and/or the rectangularity of the cross-sectional shape of the resist pattern may be deteriorated.

(c) Radiation-Sensitive Acid Generating Agent

The radiation-sensitive acid generating agent (c) is a component that is capable of generating an acid upon the irradiation with the first radioactive ray without the irradiation with the second radioactive ray, but the radiation-sensitive acid generating agent (c) substantially does not generate the acid upon the irradiation with the second radioactive ray without the irradiation with the first radioactive ray, and is different from the radiation-sensitive acid-and-sensitizer generating agent (a). Since the radiation-sensitive acid generating agent (c) has the aforementioned characteristics, the acid can be generated only in the patternwise exposed regions of the resist material film through a radioactive ray sensitization reaction upon the floodwise exposure.

The cation (I) and the cation (II) in the compound (C1) and the compound (C2) are exemplified by the monovalent onium cation represented by $X^+$ as the cation (I) and cation (II) described above, and are degraded through the irradiation with the exposure light. In the light-exposed regions, a sulfonic acid is generated from the sulfonate anion, and a proton generated through the degradation of the onium cation. The cation does not generate the radiation-sensitive sensitizer.

Examples of the monovalent onium cation represented by $X^+$ include the cations represented by the above formulae (X-1) and (X-2).

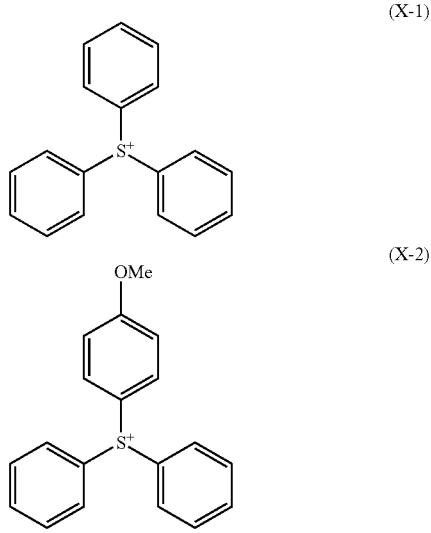

Of these, $X^+$ preferably represents a triphenylsulfonium cation.

Examples of the anion (I) and the anion (II) in the compound (C1) and the compound (C2) include anions similar to those exemplified in connection with the anion (I) and anion (II) described above.

The compound (C1) and the compound (C2) that serve in the radiation-sensitive acid generating agent (c) are exemplified by a sulfonium salt compound corresponding to the aforementioned onium salt compound.

Examples of the sulfonium salt compound include, among those exemplified in connection with the compound (C1) and the compound (C2), triphenylsulfonium trifluoromethanesulfonate, triphenylsulfonium nonafluoro-n-butanesulfonate, triphenylsulfonium perfluoro-n-octanesulfonate, triphenylsulfonium 2-bicyclo[2.2.1]hept-2-yl-1,1,2,2-tetrafluoroethanesulfonate, triphenylsulfonium 6-(adamantan-1-ylcarboxyoxy)-1,1,2,2-tetrafluorohexane-1-sulfonate, triphenylsulfonium adamantan-1-yloxycarbonylcarboxylate, triphenylsulfonium 4-trifluoromethyl salicylate, 4-methoxyphenyldiphenylsulfonium 1,2-di(cyclohexyloxycarbonyl)ethane-1-sulfonate, and the like.

The radiation-sensitive acid generating agent (c) may also include a compound other than the compound (C1) and the compound (C2), and the radiation-sensitive acid generating agent (c) other than the compound (C1) and the compound (C2) is exemplified by other onium salt compound, a diazomethane compound, a sulfonimide compound, and the like. Examples of the onium salt compound include, in addition to the sulfonium salt compound, a tetrahydrothiophenium salt compound, an iodonium salt compound, and the like.

Examples of the other sulfonium salt compound include 4-cyclohexylphenyldiphenylsulfonium trifluoromethanesulfonate, 4-cyclohexylphenyldiphenylsulfonium nonafluoro-n-butanesulfonate, 4-cyclohexylphenyldiphenylsulfonium perfluoro-n-octanesulfonate, 4-cyclohexylphenyldiphenylsulfonium2-bicyclo[2.2.1]hept-2-yl-1,1,2,2-tetrafluoroethanesulfonate, 4-methanesulfonylphenyldiphenylsulfonium trifluoromethanesulfonate, 4-methanesulfonylphenyldiphenylsulfonium nonafluoro-n-butanesulfonate, 4-methanesulfonylphenyldiphenylsulfonium perfluoro-n-octanesulfonate, 4-methanesulfonylphenyldiphenylsulfonium 2-bicyclo[2.2.1]hept-2-yl-1,1,2,2-tetrafluoroethanesulfonate, and the like.

Examples of the tetrahydrothiophenium salt compound include 1-(4-n-butoxynaphthalen-1-yl)tetrahydrothiophenium trifluoromethanesulfonate, 1-(4-n-butoxynaphthalen-1-yl)tetrahydrothiophenium nonafluoro-n-butanesulfonate, 1-(4-n-butoxynaphthalen-1-yl)tetrahydrothiophenium perfluoro-n-octanesulfonate, 1-(4-n-butoxynaphthalen-1-yl)tetrahydrothiophenium 2-bicyclo[2.2.1]hept-2-yl-1,1,2,2-tetrafluoroethanesulfonate, 1-(6-n-butoxynaphthalen-2-yl)tetrahydrothiophenium trifluoromethanesulfonate, 1-(6-n-butoxynaphthalen-2-yl)tetrahydrothiophenium nonafluoro-n-butanesulfonate, 1-(6-n-butoxynaphthalen-2-yl)tetrahydrothiophenium perfluoro-n-octanesulfonate, 1-(6-n-butoxynaphthalen-2-yl)tetrahydrothiophenium 2-bicyclo[2.2.1]hept-2-yl-1,1,2,2-tetrafluoroethanesulfonate, 1-(3,5-dimethyl-4-hydroxyphenyl)tetrahydrothiophenium trifluoromethanesulfonate, 1-(3,5-dimethyl-4-hydroxyphenyl)tetrahydrothiophenium nonafluoro-n-butanesulfonate, 1-(3,5-dimethyl-4-hydroxyphenyl)tetrahydrothiophenium perfluoro-n-octanesulfonate, 1-(3,5-dimethyl-4-hydroxyphenyl)tetrahydrothiophenium 2-bicyclo[2.2.1]hept-2-yl-1,1,2,2-tetrafluoroethanesulfonate, and the like.

Examples of the iodonium salt compound include diphenyliodonium trifluoromethanesulfonate, diphenyliodonium nonafluoro-n-butanesulfonate, diphenyliodonium perfluoro-n-octanesulfonate, diphenyliodonium 2-bicyclo[2.2.1]hept-2-yl-1,1,2,2-tetrafluoroethanesulfonate, bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, bis(4-t-butylphenyl)iodonium 2-bicyclo[2.2.1]hept-2-yl-1,1,2,2-tetrafluoroethanesulfonate, and the like.

Examples of the sulfonimide compound include N-(trifluoromethanesulfonyloxy)bicyclo[2.2.1]hept-5-ene-2,3-dicarboxyimide, N-(nonafluoro-n-butanesulfonyloxy)bicyclo[2.2.1]hept-5-ene-2,3-dicarboxyimide, N-(perfluoro-n-octanesulfonyloxy)bicyclo[2.2.1]hept-5-ene-2,3-dicarboxyimide, N-(2-bicyclo[2.2.1]hept-2-yl-1,1,2,2-tetrafluoroethanesulfonyloxy)bicyclo[2.2.1]hept-5-ene-2,3-dicarboxyimide, and the like.

Examples of the diazomethane compound include bis(n-propylsulfonyl)diazomethane, bis(isopropylsulfonyl)diazomethane, bis(n-butylsulfonyl)diazomethane, bis(tert-butylsulfonium)diazomethane, bis(cyclopentylsulfonyl)diazomethane, bis(cyclohexylsulfonyl)diazomethane, bis (phenylsulfonyl)diazomethane, bis(4-chlorophenylsulfonyl)diazomethane, bis(p-tolylsulfonyl)diazomethane, bis(2,4-xylylsulfonyl)diazomethane, bis(4-isopropylphenylsulfonyl)diazomethane, bis(4-tert-butylphenylsulfonyl)diazomethane, bis(naphthylsulfonyl) diazomethane, bis(anthracenylsulfonyl)diazomethane, and the like.

The radiation-sensitive acid generating agent (c) may be a part of the polymer constituting the polymer component (1). In this case, the radiation-sensitive acid generating agent (c) is present in the form of a group obtained by eliminating one hydrogen atom from the aforementioned compound and bound to the polymer.

In the case where the radiation-sensitive acid generating agent (c) is the component different from the polymer component (1), the lower limit of the amount of the radiation-sensitive acid generating agent (c) blended with respect to 100 parts by mass of the polymer component (1) is preferably 0.1 parts by mass, and more preferably 1 part by mass. On the other hand, the upper limit of the amount of the radiation-sensitive acid generating agent (c) blended is preferably 50 parts by mass, and more preferably 30 parts by mass.

In the case where the radiation-sensitive acid generating agent (c) is a part of the polymer constituting the polymer component (1), the lower limit of the proportion of the radiation-sensitive acid generating agent (c) contained with respect to 1 mol of the polymer component (1) is preferably 0.01 mol, more preferably 0.02 mol, and still more preferably 0.1 mol. On the other hand, the upper limit of the proportion of the radiation-sensitive acid generating agent (c) contained is preferably 0.5 mol, and more preferably 0.3 mol.

When the amount of the radiation-sensitive acid generating agent (c) blended or the proportion of the radiation-sensitive acid generating agent (c) contained is less than the lower limit, the sensitivity may be deteriorated. To the contrary, when the amount of the radiation-sensitive acid generating agent (c) blended or the proportion of the radiation-sensitive acid generating agent (c) contained is greater than the upper limit, it may be difficult to form the resist material film, and/or the rectangularity of the cross-sectional shape of the resist pattern may be deteriorated.

In the case where the generative component (2) is different from the polymer component (1), the lower limit of the content of the generative component (2) with respect to the total solid content of the chemically amplified resist material is preferably 10% by mass, and more preferably 15% by mass. On the other hand, the upper limit of the content of the generative component (2) is preferably 30% by mass, and more preferably 25% by mass. When the content of the generative component (2) falls within the above range, the sensitivity and lithography performances of the chemically amplified resist material can be more improved. The term "content of the generative component (2)" as referred to herein means the total content of the component that is different from the polymer component (1), of the generative component (2).

Other Acid Diffusion Control Agent

The chemically amplified resist material may be blended with other acid diffusion control agent than the compound (C1) and the compound (C2). The other acid diffusion control agent traps an acid and a cation, and serves as a quencher. When the chemically amplified resist material contains the other acid diffusion control agent, a surplus acid generated in the resist material film can be neutralized, whereby a chemical contrast of the latent image of the acid between the patternwise exposed regions and the patternwise unexposed regions can be increased.

The acid diffusion control agent can be classified into a radiation-sensitive compound and a radiation-insensitive compound.

The radiation-insensitive compound is preferably a basic compound. The basic compound is exemplified by hydroxide compounds, carboxylate compounds, amine compounds, imine compounds, amide compounds, and the like, and more specifically, primary to tertiary aliphatic amines, aromatic amines, heterocyclic amines, nitrogen-containing compounds that include a carboxyl group, nitrogen-containing compounds that include a sulfonyl group, nitrogen-containing compounds that include a hydroxyl group, nitrogen-containing compounds that include a hydroxyphenyl group, alcoholic nitrogen-containing compounds, nitrogen-containing compounds that include a carbamate group, amide compounds, imide compounds, and the like. Of these, the nitrogen-containing compounds that include a carbamate group are preferred.

The basic compound may also be a Troger's base; a hindered amine such as diazabicycloundecene (DBU), diazabicyclononene (DBM) and the like; and an ionic quencher such as tetrabutylammonium hydroxide (TBAH), tetrabutylammonium lactate and the like.

Examples of the primary aliphatic amine include: ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, tetraethylenepentamine, and the like.

Examples of the secondary aliphatic amine include: dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyl tetraethylene pentamine, and the like.

Examples of the tertiary aliphatic amine include: trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, N,N,N',N'-tetramethyltetraethylenepentamine, and the like.

Examples of the aromatic amine and the heterocyclic amine include: an aniline derivative such as aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, N,N-dimethyltoluidine; diphenyl(p-tolyl)amine; methyldiphenylamine; triphenylamine; phenylenediamine; naphthylamine; diaminonaphthalene; a pyrrole derivative such as pyrrole, 2H-pyrrole, 1-methylpyrrole, 2,4-dimethylpyrrole, 2,5-dimethylpyrrole, N-methylpyrrole; an oxazole derivative such as oxazole and isoxazole; a thiazole derivative such as thiazole and isothiazole; an imidazole derivative such as imidazole, 4-methylimidazole, 4-methyl-2-phenylimidazole; pyrazole derivative; a furazane derivative; a pyrroline derivative such as pyrroline, 2-methyl-1-pyrroline; a pyrrolidine derivative such as pyrrolidine, N-methylpyrrolidine, pyrrolidinone, N-methylpyrrolidone; an imidazoline derivative; an imidazolidine derivative; a pyridine derivative such as pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 4-pyrrolidinopyridine, 2-(1-ethylpropyl)pyridine, aminopyridine, dimethylaminopyridine; a pyridazine derivative; a pyrimidine derivative; a pyrazine derivative; a pyrazoline derivative; a pyrazolidine derivative; a piperidine derivative; a piperazine derivative; a morpholine derivative; an indole derivative; an isoindole derivative; a 1H-indazole derivative; an indoline derivative; a quinolone derivative such as quinoline, 3-quinolinecarbonitrile; an isoquinoline derivative; a cinnoline derivative; a quinazoline derivative; a quinoxaline derivative; a phthalazine derivative; a purine derivative; a pteridine derivative; a carbazole derivative; a phenanthridine derivative; an acridine derivative; a phenazine derivative; a 1,10-phenanthroline derivative; an adenine derivative; an adenosine derivative; a guanine derivative; a guanosine derivative; an uracil derivative; an uridine derivative; and the like.

Examples of the nitrogen-containing compound containing a carboxy group include: aminobenzoic acid; indolecarboxylic acid; an amino acid derivative such as nicotinic acid, alanine, arginine, aspartic acid, glutamic acid, glycine, histidine, isoleucine, glycylleucine, leucine, methionine, phenylalanine, threonine, lysine, 3-aminopyrazine-2-carboxylic acid, methoxyalanine, and the like.

Examples of the nitrogen-containing compound containing a sulfonyl group include: 3-pyridinesulfonic acid, pyridinium p-toluenesulfonate, and the like.

Examples of the nitrogen-containing compound containing a hydroxyl group, of the nitrogen-containing compound containing a hydroxyphenyl group, and of the alcoholic nitrogen-containing compound include: 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidineethanol, 1-aziridineethanol, N-(2-hydroxyethyl)phthalimide, N-(2-hydroxyethyl)isonicotineamide, and the like.

Examples of the nitrogen-containing compound containing a carbamate group include: N-(tert-butoxycarbonyl)-L-alanine, N-(tert-butoxycarbonyl)-L-alanine methyl ester, (S)-(−)-2-(tert-butoxycarbonylamino)-3-cyclohexyl-1-propanol, (R)-(+)-2-(tert-butoxycarbonylamino)-3-methyl-1-butanol, (R)-(+)-2-(tert-butoxycarbonylamino)-3-phenyl-propanol, (S)-(−)-2-(tert-butoxycarbonylamino)-3-phenylpropanol, (R)-(+)-2-(tert-butoxycarbonylamino)-3-phenyl-1-propanol, (S)-(−)-2-(tert-butoxycarbonylamino)-3-phenyl-1-propanol, (R)-(+)-2-(tert-butoxycarbonylamino)-1-propanol, (S)-(−)-2-(tert-butoxycarbonylamino)-1-propanol, N-(tert-butoxycarbonyl)-L-asparatic acid 4-benzyl ester, N-(tert-butoxycarbonyl)-O-benzyl-L-threonine, (R)-(+)-1-(tert-butoxycarbonyl)-2-tert-butyl-3-methyl-4-imidazolidinone, (S)-(−)-1-(tert-butoxycarbonyl)-2-tert-butyl-3-methyl-4-imidazolidinone, N-(tert-butoxycarbonyl)-3-cyclohexyl-L-alanine methyl ester, N-(tert-butoxycarbonyl)-L-cysteine methyl ester, N-(tert-butoxycarbonyl)ethanolamine, N-(tert-butoxycarbonyl)ethylenediamine, N-(tert-butoxycarbonyl)-D-glucoseamine, Nα-(tert-butoxycarbonyl)-L-glutamine, 1-(tert-butoxycarbonyl)imidazole, N-(tert-butoxycarbonyl)-L-isoleucine, N-(tert-butoxycarbonyl)-L-isoleucine methyl ester, N-(tert-butoxycarbonyl)-L-leucinol, Nα-(tert-butoxycarbonyl)-L-lysine, N-(tert-butoxycarbonyl)-L-methionine, N-(tert-butoxycarbonyl)-3-(2-naphthyl)-L-alanine, N-(tert-butoxycarbonyl)-L-phenylalanine, N-(tert-butoxycarbonyl)-L-phenylalanine methyl ester, N-(tert-butoxycarbonyl)-D-prolinal, N-(tert-butoxycarbonyl)-L-proline, N-(tert-butoxycarbonyl)-L-proline-N'-methoxy-N'-methylamide, N-(tert-butoxycarbonyl)-1H-pyrazole-1-carboxyamidine, (S)-(−)-1-(tert-butoxycarbonyl)-2-pyrrolidinemethanol, (R)-(+)-1-(tert-butoxycarbonyl)-2-pyrrolidinemethanol, 1-(tert-butoxycarbonyl)3-[4-(1-pyrrolyl)phenyl]-L-alanine, N-(tert-butoxycarbonyl)-L-serine, N-(tert-butoxycarbonyl)-L-serine methyl ester, N-(tert-butoxycarbonyl)-L-threonine, N-(tert-butoxycarbonyl)-p-toluenesulfonamide, N-(tert-butoxycarbonyl)-S-trityl-L-cysteine, Nα-(tert-butoxycarbonyl)-L-tryptophan, N-(tert-butoxycarbonyl)-L-tyrosine, N-(tert-butoxycarbonyl)-L-tyrosine methyl ester, N-(tert-butoxycarbonyl)-L-valine, N-(tert-butoxycarbonyl)-L-valine methyl ester, N-(tert-butoxycarbonyl)-L-valinol, tert-butyl N-(3-hydroxypropyl)carbamate, tert-butyl N-(6-aminohexyl)carbamate, tert-butylcarbamate, tert-butyl carbazate, tert-butyl-N-(benzyloxy) carbamate, tert-butyl-4-benzyl-1-piperazinecarboxylate, tert-butyl (1S,4S)-(−)-2,5-diazabicyclo[2.2.1]heptane-2-carboxylate, tert-butyl-N-(2,3-dihydroxypropyl)carbamate, tert-butyl (S)-(−)-4-formyl-2,2-dimethyl-3-oxazolidinecarboxylate, tert-butyl[R—(R*,S*)]—N-[2-hydroxy-2-(3-hydroxyphenyl)-1-methylethyl] carbamate, tert-butyl-4-oxo-1-piperidinecarboxylate, tert-butyl 1-pyrrolecarboxylate, tert-butyl 1-pyrrolidinecarboxylate, tert-butyl (tetrahydro-2-oxo-3-furanyl)carbamate, and the like.

Examples of the amide compound include: formamide, N-methylformamide, N,N-dimethylformamide, acetamide, N-methylacetamide, N,N-dimethylacetamide, propionamide, benzamide, 1-cyclohexylpyrrolidone, and the like.

Examples of the imide compound include: phthalimide, succinimide, maleimide, and the like.

The radiation-sensitive compound is classified into a compound that is degraded by a radioactive ray to lose acid diffusion controllability (radioactive ray-degradable compound) and a compound that is generated by a radioactive ray to acquire acid diffusion controllability (radioactive ray-generable compound).

When the radioactive ray-degradable compound is degraded only in the patternwise exposed regions in the patternwise exposure step, the effect of trapping the acid and the cation is deteriorated in the patternwise exposed regions, whereas the effect of trapping the acid and the cation is maintained in the patternwise unexposed regions. Accordingly, a chemical contrast of the latent image of the acid between the light-exposed regions and the light-unexposed regions can be improved.

The radioactive ray-degradable compound is preferably a sulfonic acid salt or carboxylic acid salt containing a radioactive ray-degradable cation other than the compound (C1) and the compound (C2). As the sulfonic acid in the sulfonic acid salt, a weaker acid is preferred, and a sulfonic acid that includes a hydrocarbon group having 1 to 10 carbon atoms, and not having a fluorine atom is more preferred. Examples of the sulfonic acid include sulfonic acids such as alkylsulfonic acids, benzenesulfonic acid and 10-camphorsulfonic acid. As the carboxylic acid in the carboxylic acid salt, a weaker acid is preferred, and a carboxylic acid having 1 to 20 carbon atoms is more preferred. Examples of the carboxylic acid include carboxylic acids such as formic acid, acetic acid, propionic acid, tartaric acid, succinic acid, cyclohexylcarboxylic acid, benzoic acid and salicylic acid. The radioactive ray-degradable cation in the carboxylic acid salt containing the radioactive ray-degradable cation is preferably an onium cation, and examples of the onium cation include iodonium cations, and the like.

When the radioactive ray-generable compound is generated only in the patternwise exposed regions in the patternwise exposure step, the effect of trapping the acid and the cation is exerted in the patternwise exposed regions, but not in the patternwise unexposed regions.

The radioactive ray-generable compound may be a radioactive ray-generable compound that is not generated in the patternwise exposure step but is generated in the floodwise exposure step. In this case, the radiation-sensitive sensitizer can be generated efficiently in the regions light-exposed in the patternwise exposure step, and additionally an unnecessary acid and cation in the regions unexposed to light in floodwise exposure step can be trapped.

The radioactive ray-generable compound is preferably a compound that is capable of generating a base upon an exposure (radiation-sensitive base generating agent), and more preferably a nitrogen-containing organic compound that is capable of generating an amino group.

Examples of the radiation-sensitive base generating agent include compounds disclosed in Japanese Unexamined Patent Application, Publication Nos. H4-151156, H4-162040, H5-197148, H5-5995, H6-194834, H8-146608 and H10-83079, and European patent No. 622682.

The radiation-sensitive base generating agent is exemplified by a compound that includes a carbamate group (urethane bond), a compound that includes an acyloxyimino group, an ionic compound (anion-cation complex), a compound that includes a carbamoyloxyimino group, and the like, and a compound that includes a carbamate group (urethane bond), a compound that includes an acyloxyimino group, and an ionic compound (anion-cation complex) are preferred.

Further, as the radiation-sensitive base generating agent, a compound having a ring structure in a molecule thereof is preferred. Examples of the ring structure include a benzene ring structure, a naphthalene ring structure, an anthracene ring structure, a xanthone ring structure, a thiaxanthon ring structure, an anthraquinone ring structure, a fluorene ring structure, and the like.

Examples of the radiation-sensitive base generating agent include: 2-nitrobenzylcarbamate, 2,5-dinitrobenzyl cyclohexylcarbamate, N-cyclohexyl-4-methylphenylsulfonamide, 1,1-dimethyl-2-phenylethyl-N-isopropylcarbamate, and the like.

The acid diffusion control agent may be a compound that is generated through a thermal reaction to acquire acid diffusion controllability (thermally-generable compound). In this case, it is desired that the acid diffusion control agent is generated in the baking step performed after the floodwise exposure step. In light of the acid diffusion control agent thus acquiring the acid diffusion controllability in baking step, the heating temperature in the baking step described later is preferably higher than the heating temperatures in other steps.

In the case where the chemically amplified resist material contains the acid diffusion control agent, the lower limit of the content of the acid diffusion control agent with respect to 100 parts by mass of the polymer component (1) is preferably 0.001 parts by mass, and more preferably 0.01 parts by mass. On the other hand, the upper limit of the content of the acid diffusion control agent is preferably 20 parts by mass, and more preferably 10 parts by mass. When the content of the acid diffusion control agent is less than the lower limit, the acid diffusion control agent may not be capable of trapping the acid and the cation satisfactorily. To the contrary, when the content of the acid diffusion control agent is greater than the upper limit, the sensitivity may be unduly decreased.

Radical Trapping Agent

The radical trapping agent traps a free radical. When the chemically amplified resist material contains the radical trapping agent, the generation of the radiation-sensitive sensitizer through a reaction mediated by the radical in the patternwise unexposed regions can be reduced, leading to a greater improvement of a contrast in terms of acid concentration between the patternwise exposed regions and the light-unexposed regions after the floodwise exposure step described later. The radical trapping agent is exemplified by compounds such as phenol compounds, quinone compounds and amine compounds, and naturally occurring antioxidants such as rubber, and the like.

Crosslinking Agent

The crosslinking agent is used for triggering a crosslinking reaction between polymer component molecules in the baking step following the floodwise exposure through the acid-catalyzed reaction, to thereby increase the molecular weight of the polymer component and make the same insoluble to the developer solution, being different from the polymer component. As the resist material contains the crosslinking agent, a polar site is unpolarized simultaneously with crosslinking and the resist material is made insoluble to the developer solution, thereby enabling a negative resist material to be provided.

The crosslinking agent is a compound having at least two functional groups. The functional group is preferably at least one selected from the group consisting of a (meth)acryloyl group, a hydroxymethyl group, an alkoxymethyl group, an epoxy group and a vinyl ether group.

Other Additive

Other additive is exemplified by a surfactant, an antioxidant, a dissolution inhibitor, a plasticizer, a stabilizer, a colorant, a halation inhibitor, a dye, and the like. Well-known additives may be used as the other additive. As the surfactant, for example, an ionic and nonionic fluorochemical surfactant, a silicone surfactant, and the like may be used. Examples of the antioxidant include a phenol antioxidant, an antioxidant composed of an organic acid derivative, a sulfur-containing antioxidant, a phosphorus antioxidant, an amine antioxidant, an antioxidant composed of amine-aldehyde condensate, an antioxidant composed of amine-ketone condensate, and the like.

Solvent

The solvent is used for dissolving a composition of the resist material to facilitate formation of a resist material film by a coater by a method such as spin coating. It is to be noted that the compounds contained in the radiation-sensitive sensitizer generating agent (b) and the like are excluded from the solvent. Examples of the solvent include: ketones such as cyclohexanone and methyl 2-amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, diethylene glycol dimethyl ether; esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, propylene glycol monomethyl ether acetate, and propylene glycol mono-tert-butyl ether acetate; and the like.

Preparation Method of Chemically Amplified Resist Material

The chemically amplified resist material may be prepared by, for example, mixing the polymer component (1) and the component (2), and other optional component is necessary, at a predetermined ratio. The chemically amplified resist material is preferably filtered through a filter having a pore size of about 0.2 µm, for example, after the mixing. The lower limit of the total solid content concentration of the chemically amplified resist material is typically 0.1% by mass, preferably 0.5% by mass, and more preferably 1% by mass. On the other hand, the upper limit of the total solid content concentration is typically 50% by mass, preferably 30% by mass, and more preferably 20% by mass.

Resist Pattern-Forming Method

The resist material is suitably used in the two-step exposure lithography process. In other words, the lithography process (including the resist pattern-forming method) according to the embodiment of the present invention comprises: a film-forming step of forming a resist material film on a substrate using the resist material; a patternwise exposure step of patternwise exposing the resist material film to a first radioactive ray through a mask; a floodwise exposure step of floodwise exposing the resist material film obtained after the patternwise exposure step to a second radioactive ray; a baking step of baking the resist material film obtained after the floodwise exposure step; and a development step of developing the resist material film obtained after the baking step with a developer solution.

Figure 2:
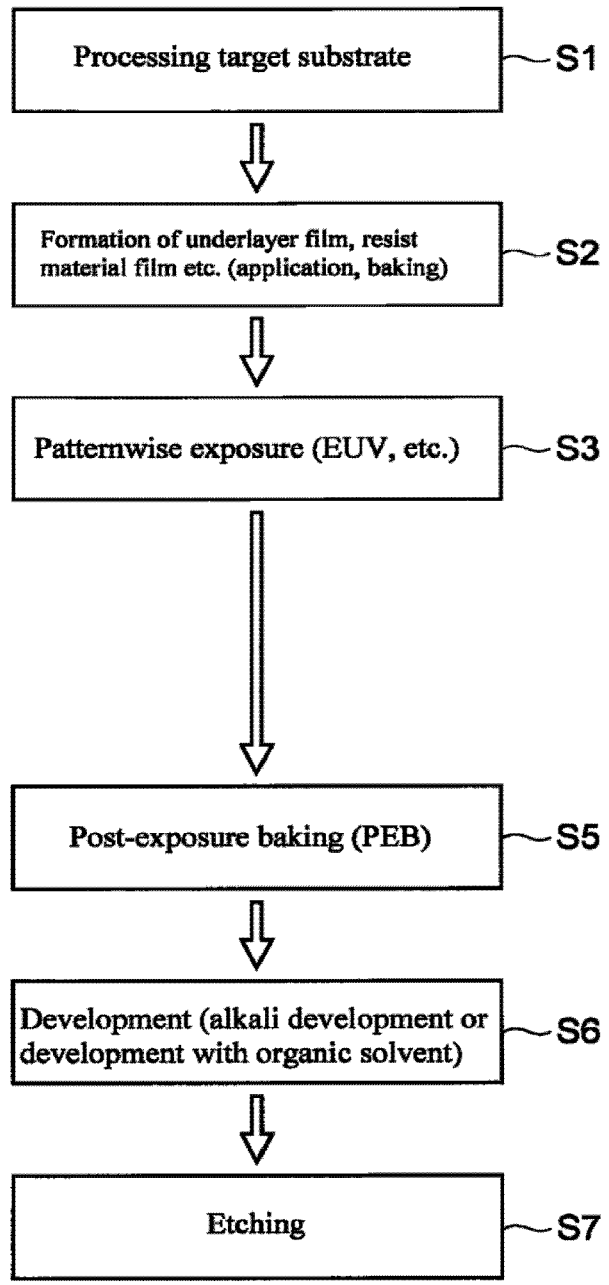
FIG. 2 shows a flow chart illustrating one example of the resist pattern-forming method employing a conventional chemically amplified resist material.

FIG. 1 shows a flow chart illustrating a lithographic process according to the embodiment of the present invention. FIG. 2 shows a flow chart illustrating an example of the resist pattern-forming method employing a conventional chemically amplified resist material.

As shown in FIG. 1, the lithographic process according to this embodiment includes the following steps.

Step S1: a step of preparing a substrate subjected to the process

Step S2: a step of forming an underlayer film and a resist material film (film-forming step)

Step S3: a step of generating an acid in light-exposed regions by patternwise exposure (patternwise exposure step)

Step S4: a step of proliferating the acid only in the patternwise exposed regions by the floodwise exposure (floodwise exposure step)

Step S5: a step of causing a polarity change reaction in the patternwise exposed regions by post-exposure baking (baking step)

Step S6: a step of forming a resist pattern by a developing treatment (development step)

Step S7: a step of transferring the pattern by etching (etching step)

Step S1

A substrate subjected to the process in the following steps (processing target substrate) may be constituted of a semiconductor wafer such as a silicon substrate, a silicon dioxide substrate, a glass substrate, and an ITO substrate, or can be the semiconductor wafer with an insulating film layer being formed thereon.

Step S2: Film-Forming Step

The resist material film is formed by using the resist material of the embodiment of the present invention. Examples of the forming method of the resist material film include: a method of applying a liquid resist material by spin coating and the like, and a method of attaching a film-like (solid) resist material. In the case of applying the liquid resist material, heating (prebaking) may take place following the application to volatilize the solvent in the resist material. Formation conditions of the resist material film are appropriately selected according to properties of the resist material, thickness of the resist material film to be obtained, and the like. An average thickness of the resist material film is preferably no less than 1 nm and no greater than 5,000 nm, more preferably no less than 10 nm and no greater than 1,000 nm, and still more preferably no less than 30 nm and no greater than 200 nm.

Prior to forming the resist material film on the substrate, an underlayer film (antireflective film, film for ameliorating resist adhesiveness, film for ameliorating resist shape etc.) may be formed on the substrate. By forming the antireflective film, generation of standing wave due to reflection of the radioactive ray from the substrate and the like in the patternwise exposure step can be inhibited. By forming a film for ameliorating resist adhesiveness, adhesiveness between the substrate and the resist material film can be improved. By forming the film for ameliorating resist shape, a post-development resist shape can be further improved. In other words, trailing or constriction of the resist can be reduced. On the other hand, in order to prevent deterioration of the resist shape due to generation of the standing wave of the radioactive ray of the floodwise exposure, it is preferable that the thickness of the underlayer film is designed to inhibit reflection of the radioactive ray of the floodwise exposure. It is desirable that the underlayer film does not absorb the radioactive ray of the floodwise exposure. If the underlayer film absorbs the radioactive ray of the floodwise exposure, a radioactive ray sensitization reaction would be caused in the resist material film due to energy transfer or electron transfer from the underlayer film, and an acid may thus be generated in the patternwise unexposed regions. Given this, a buffer layer that does not propagate the radioactive ray sensitization reaction may be provided between the resist material film and the underlayer film, to thereby prevent sensitization from the underlayer film having absorbed the radioactive ray.

A protective film may further be formed on the resist material film. By forming the protective film, deactivation of the radiation-sensitive sensitizer, the acid, and a reaction intermediate thereof generated in the patternwise exposure step S3 can be inhibited and process stability can be improved. The protective film may be an absorption film that absorbs at least a part of the wavelength of nonionizing radiation that is directly absorbed by the component (a) or (c) (radiation-sensitive acid generating agent) in order to prevent an acid generating reaction in the light-unexposed regions in the floodwise exposure step. By using the absorption film, out-of-band light (OOB light), which is a radioactive ray of an ultraviolet ray region generated upon exposure to EUV, is prevented from entering into the resist material film, and degradation of the radiation-sensitive acid generating agent or the radiation-sensitive acid generating group in the patternwise unexposed regions can also be prevented. In addition, in the case of the absorption film being formed directly on the resist material film, in order to inhibit generation of an acid in the resist material film by the radioactive ray sensitization reaction in the patternwise unexposed regions, it is preferable that the radioactive ray sensitization reaction from the protective film is not triggered by the wavelength of the second radioactive ray in the floodwise exposure step. In addition, a buffer layer may be provided between the resist material film and the protective film to prevent sensitization from the absorption film having absorbed the radioactive ray, such that the radiation-sensitive sensitizer in the resist material film is not sensitized by energy transfer or electron transfer and the like from the protective film. By forming the absorption film on the resist material film following the patternwise exposure step S3 and prior to the floodwise exposure step S4, generation of an acid directly from the radiation-sensitive acid generating agent or the radiation-sensitive acid generating group remaining on the resist material film obtained after the patternwise exposure step S3 through the irradiation with the second radioactive ray in the floodwise exposure step S4 can further be inhibited.

Step S3: Patternwise Exposure Step

In the patternwise exposure step S3, a light shielding mask having a predetermined pattern is disposed on the resist material film formed in the film-forming step S2. Thereafter, the resist material film is irradiated with the first radioactive ray from an exposure system (radioactive ray-irradiating module) including a projection lens, an electronic optics mirror, or a reflection mirror, through the mask (patternwise exposure).

The first radioactive ray used for the patternwise exposure is ionizing radiation or nonionizing radiation having a wavelength of no greater than 250 nm. The upper limit of the wavelength of the nonionizing radiation is preferably 250 nm, and more preferably 200 nm. On the other hand, the lower limit of the wavelength of the nonionizing radiation is preferably 150 nm, and more preferably 190 nm.

The ionizing radiation is a radioactive ray having a sufficient energy for ionizing an atom or a molecule. Meanwhile, the nonionizing radiation is a radioactive ray not having a sufficient energy for ionizing an atom or a molecule. Examples of the ionizing radiation include: gamma ray, X-ray, alpha ray, heavy particle ray, proton beam, beta ray, ion beam, electron beam, EUV, and the like. As the ionizing radiation used for the patternwise exposure, electron beam, EUV and ion beam are preferred, and electron beam and EUV are more preferred. Examples of the nonionizing radiation include those having a wavelength of no greater than 250 nm such as a KrF excimer laser beam and an ArF excimer laser beam.

As the light for the patternwise exposure, for example, electron beam of 1 keV to 200 keV, (EUV) having a wavelength of 13.5 nm, excimer laser beam (ArF excimer laser beam) of 193 nm, and excimer laser beam (KrF excimer laser beam) of 248 nm are frequently used. Exposure dose in the patternwise exposure may be smaller than in the case of floodwise exposure using the chemically amplified resist of the embodiment of the present invention. By the patternwise exposure, the components (a) to (c) in the resist material film degrade and generate an acid and the radiation-sensitive sensitizer that absorbs the second radioactive ray.

A step-and-scan exposure system called "scanner" is widely used for exposure. In the present method, by performing scanning exposure while synchronizing the mask with the substrate, a pattern is formed for every one shot. This exposure triggers a selective reaction in exposed sites in the resist.

In addition, prior to performing the floodwise exposure step S4, an absorption film that absorbs at least a part of the wavelength of nonionizing radiation, which is directly absorbed by the radiation-sensitive acid generating agent in the component (a) or (c), may be formed on the resist material film after the patternwise exposure step S3. By forming the absorption film, generation of acid directly from the radiation-sensitive acid generating agent or the radiation-sensitive acid generating group remaining on the resist material film after the patternwise exposure step S3 through the irradiation with the second radioactive ray in the floodwise exposure step S4 described later can be further inhibited.

In the case of using the radiation-sensitive sensitizer generating agent (b) having an alcoholic hydroxyl group in which a hydrogen atom is not substituted, it is preferable that the resist material film is placed under a vacuum atmosphere or an inert atmosphere containing nitrogen or argon, following the patternwise exposure step S3 and prior to performing the floodwise exposure step S4 described later. By placing the resist material film under the above-described atmosphere, exposure of the resist material film to oxygen upon an exposure and stopping of the radical reaction by this oxygen can be inhibited, and quenching of the acid by a slight amount of a basic compound can be inhibited, leading to a tendency that the process is further stabilized. The upper limit of the time period from the completion of the patternwise exposure step S3 until performing the floodwise exposure step S4 (keeping time) is preferably 30 min and more preferably 10 min. The keeping time no greater than 30 min tends to inhibit decreases in sensitivity. On the other hand, in the case of using the radiation-sensitive sensitizer generating agent (b) (in other words, a ketal compound, an acetal compound, or an ortho ester compound, and the like) having an alcoholic hydroxyl group in which a hydrogen atom is substituted, after the patternwise exposure step S3 and prior to performing the floodwise exposure step S4 described later, an atmosphere in which the resist material film is present is preferably ambient air cleaned by an amine eliminating filter. In the case of using the radiation-sensitive sensitizer generating agent (b), the above-described influence of oxygen is less likely, and treatment in the ambient air cleaned by the amine eliminating filter is therefore possible. By placing the resist material film in the above-described atmosphere, quenching of the acid by a slight amount of a basic compound can be inhibited, leading to a tendency that the process is further stabilized. The upper limit of the time period from the completion of the patternwise exposure step S3 until performing the floodwise exposure step S4 (keeping time) is preferably 30 min and more preferably 10 min. The keeping time no greater than 30 min tends to be able to inhibit decreases in sensitivity.

Figure 3:
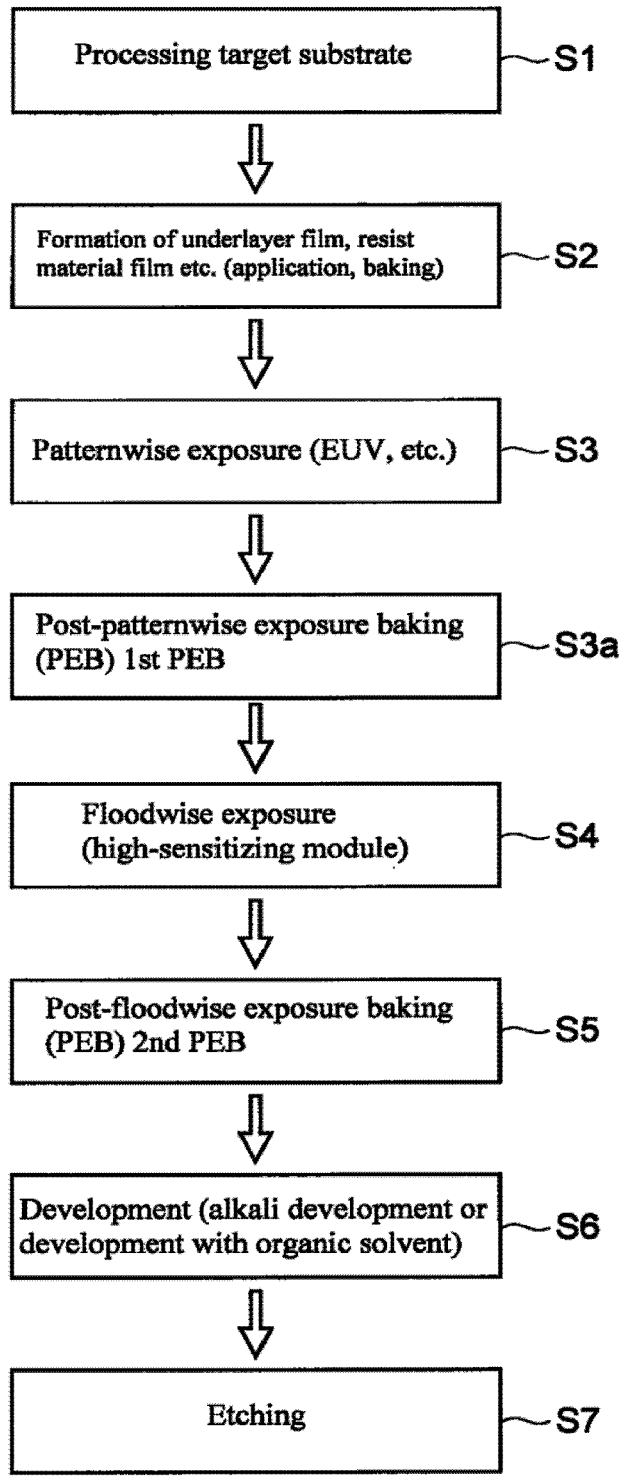
FIG. 3 shows a flow chart illustrating another embodiment of the resist pattern-forming method employing the chemically amplified resist material according to an embodiment of the present invention.

The resist pattern-forming method of the embodiment of the present invention may further comprise, following the patternwise exposure step S3 and prior to the floodwise exposure step S4 described later, a step of conveying the substrate from the exposure system in which the patternwise exposure step S3 takes place to the exposure system in which the floodwise exposure step S4 takes place. In addition, the floodwise exposure may take place in an in-line connected application developing apparatus, or in a module corresponding to an interface with an exposure device. It is to be noted that, in a case in which the component (2) contains a ketal compound, an acetal compound or an ortho ester compound, the resist pattern-forming method of the embodiment of the present invention may comprise a baking step S3a (may also be referred to as post-patterning exposure baking (PPEB or PEB)) following the patternwise exposure step S3 and prior to the floodwise exposure step S4 described later (see FIG. 3). The heating temperature in the baking step is preferably no less than 30° C. and no greater than 150° C., more preferably no less than 50° C. and no greater than 120° C., and still more preferably no less than 60° C. and no greater than 100° C. The heating time is preferably no less than 5 sec and no greater than 3 min, and more preferably no less than 10 sec and no greater than 60 sec. Furthermore, the baking preferably takes place in a humidity-controlled environment, since, in the case of using a hydrolysis reaction as the deprotection reaction for generating the radiation-sensitive sensitizer, humidity influences the reaction speed. The resist pattern-forming method comprising the baking step S3a can accelerate generation of the radiation-sensitive sensitizer by a hydrolysis reaction from an acetal compound, an ortho ester compound, a ketal compound or the like to a carbonyl compound.

Step S4: Floodwise Exposure Step

In the floodwise exposure step S4, an entire surface (entire surface with both the patternwise exposed regions and the patternwise unexposed regions) of the resist material film after the patternwise exposure step S3 is irradiated with the second radioactive ray from a high-sensitizing module (may also be referred to as an exposure system or a radioactive ray-irradiating module) having a projection lens (or a light source) (floodwise exposure). The floodwise exposure may be either an exposure of the entire face of the wafer, a combination of local exposures, or overlapping exposures. As a light source for the floodwise exposure, a general light source may be employed: in addition to an ultraviolet ray from a mercury lamp, a xenon lamp, and the like controlled to have a desired wavelength by a band-pass filter and a cut-off filter, a narrow-bandwidth ultraviolet ray from an LED light source, a laser diode, a laser light source and the like may also be used. In the floodwise exposure, only the radiation-sensitive sensitizer generated in the patternwise exposed regions in the resist material film absorbs the radioactive ray. As a result, in the floodwise exposure, absorption of radioactive ray takes place selectively in the patternwise exposed regions. This allows continuous generation of an acid only in the patternwise exposed regions upon the floodwise exposure, and significant improvement of sensitivity. On the other hand, since no acid is generated in the patternwise unexposed regions, improvement of sensitivity is possible while maintaining the chemical contrast in the resist material film.

The second radioactive ray used for the floodwise exposure has a wavelength greater than the wavelength of the nonionizing radiation in the first radioactive ray, and is a nonionizing radiation having a wavelength greater than 250 nm, which is more preferably a near ultraviolet ray (wavelength: 250 to 450 nm).

In the floodwise exposure step S4, in order to inhibit the acid generating reaction in the patternwise unexposed regions, exposure with a radioactive ray having a wavelength greater than the wavelength of the radioactive ray that can be absorbed by the polymer component (1), the radiation-sensitive acid generating agent, and the radiation-sensitive sensitizer generating agent is necessary. In consideration of these, the lower limit of a wavelength of the nonionizing radiation for the floodwise exposure lower limit is preferably 280 nm, and more preferably 320 nm. In the case of generating the radiation-sensitive sensitizer that can absorb the radioactive ray having a greater wavelength, the wavelength of the nonionizing radiation may be no less than 350 nm. However, if the wavelength of the nonionizing radiation is too long, efficiency of the radioactive ray sensitization reaction would be deteriorated; and therefore it is desirable to use a nonionizing radiation having a wavelength as short as possible that can be absorbed by the radiation-sensitive sensitizer, while avoiding a wavelength of the radioactive ray that can be absorbed by the polymer component, the radiation-sensitive acid generating agent, and the radiation-sensitive sensitizer generating agent. From such a viewpoint, the upper limit of the wavelength of the nonionizing radiation is preferably 450 nm and more preferably 400 nm.

The patternwise exposure step S3 and/or the floodwise exposure step S4 may be performed either by liquid immersion lithography (liquid immersion exposure) or by dry lithography (dry exposure). The "liquid immersion lithography" as referred to means an exposure performed in a state in which a liquid is interposed between the resist material film and a projection lens. On the other hand, the "dry lithography" as referred to means an exposure performed: in a state in which a gas is interposed between the resist material film and the projection lens; under a reduced pressure; or under vacuum.

In addition, the liquid immersion lithography in the patternwise exposure step S3 and/or the floodwise exposure step S4 may also be performed in a state in which a liquid whose refractive index is no less than 1.0 is interposed between the resist material film or the protective film formed in the film-forming step S2 and the projection lens. The protective film is preferably a film designated for reflection prevention or reaction stability improvement. In addition, the protective film is preferably a film capable of liquid penetration prevention, water repellency improvement on the film surface, and prevention of defect caused by the liquid in the liquid immersion lithography.

In the liquid immersion lithography in the floodwise exposure step S4, the liquid may also be a liquid that absorbs at least a part of the wavelength of the second radioactive ray directly absorbed by the component (a) or (c) (radiation-sensitive acid generating agent). By using the liquid in the liquid immersion lithography, generation of acid directly from the radiation-sensitive acid generating agent or the radiation-sensitive acid generating group remaining in the resist material film through the irradiation with the second radioactive ray in the floodwise exposure step S4 can further be inhibited.

In the case of performing the patternwise exposure step S3 and/or the floodwise exposure step S4 by dry lithography, these steps may be performed in any of: ambient air, under a vacuum atmosphere, and under an inert atmosphere, and preferably performed under a vacuum atmosphere or under an inert atmosphere containing nitrogen or argon, and the upper limit of the basic compound concentration in the atmosphere upon performing is preferably 20 ppb, more preferably 5 ppb, and still more preferably 1 ppb.

Step S5: Baking Step

In the baking step S5, the resist material film obtained after the floodwise exposure step S4 is heated (hereinafter may be also referred to as "post-flood exposure baking (PFEB)" or "post-exposure baking (PEB)"). It is to be noted that, if the resist pattern-forming method of the embodiment of the present invention includes the baking step S3a following the patternwise exposure step S3 and prior to the floodwise exposure step S4, hereinafter, the baking step S3a may be also referred to as "1st PEB step" and the baking step S5 may be also referred to as "2nd PEB step" (see FIG. 3). Baking conditions may be as follows, for example: in the ambient air, under an inert gas atmosphere of nitrogen, argon and the like, no lower than 50° C. and no higher than 200° C., no less than 10 sec and no more than 300 sec. The baking conditions within the above specified range are likely to be able to control diffusion of acid and to secure processing speed of the semiconductor wafer. In the baking step S5, a polarity change reaction such as a deprotection reaction of the polymer component (1), a crosslinking reaction, and the like are triggered by an acid generated in the patternwise exposure step S3 and the floodwise exposure step S4. In addition, although a resist side wall may be waved under influence of the standing wave of the radioactive ray in the resist material film, the baking step S5 can inhibit the waving through diffusion of the reactant.

Step S6: Development Step

In the development step S6, the resist material film obtained after the baking step S5 is brought into contact with the developer solution. Development takes place through a selective change in solubility to a developer solution in the patternwise exposed regions by a reaction within the resist material film in the baking step S5, to thereby form a resist pattern. The developer solution can be classified into a positive developer solution and a negative developer solution.

As the positive developer solution, an alkaline developer solution is preferred. The alkaline developer solution selectively dissolves high-polarity sites of the post-exposure resist material film. Examples of the alkaline developer solution include aqueous alkaline solutions prepared by dissolving at least one of the alkaline compounds such as potassium hydroxide, sodium hydroxide, sodium carbonate, potassium carbonate, sodium phosphate, sodium silicate, ammonia, amines (such as ethanolamine), and tetraalkylammonium hydroxide (TAAH). As the alkaline developer solution, an aqueous alkaline solution prepared by dissolving TAAH is preferred. Examples of the TAAH include: tetramethylammonium hydroxide (TMAH), tetraethylammonium hydroxide, tetrapropylammonium hydroxide, tetrabutylammonium hydroxide, methyltriethylammonium hydroxide, trimethylethylammonium hydroxide, dimethyldiethylammonium hydroxide, trimethyl(2-hydroxyethyl)ammonium hydroxide (i.e. choline), triethyl(2-hydroxyethyl)ammonium hydroxide, dimethyldi(2-hydroxyethyl)ammonium hydroxide, diethyldi(2-hydroxyethyl)ammonium hydroxide, methyltri(2-hydroxyethyl)ammonium hydroxide, ethyltri(2-hydroxyethyl)ammonium hydroxide, and tetra(2-hydroxyethyl)ammonium hydroxide.

As the positive developer solution, a 2.38% by mass aqueous solution of tetramethylammonium hydroxide (TMAH) is widely used.

In alkaline development, a pattern is formed through a phenomenon in which carboxylic acid and the hydroxyl group generated in the resist material film following the exposure are ionized and eluted in the alkaline developer solution. Following the development, a water washing treatment called rinsing takes place in order to remove the developer solution remaining on the substrate.

As the negative developer solution, an organic developer solution is preferred. The organic developer solution selectively dissolves low-polarity sites of the post-exposure resist material film. The organic developer solution is used for improving resolving performance and a process window by a punching pattern such as hole and trench (groove). In this case, a dissolution contrast between the patternwise exposed regions and the patternwise unexposed regions is obtained through a difference in affinity between the solvent and the organic developer solution in the resist material film. A high-polarity site has low solubility to the organic developer solution and remains as a resist pattern. Examples of the organic developer solution include 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, amyl acetate, butenyl acetate, isoamyl acetate, propyl formate, butyl formate, isobutyl formate, amyl formate, isoamyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, amyl lactate, isoamyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, 2-phenylethyl acetate, and the like.

The resist pattern obtained after the development step S6 (including the rinsing treatment) may be heated (may also be referred to as "post-baking"). The post-baking can vaporize and remove a rinse agent remaining from the rinse treatment and can harden the resist pattern.

Step S7: Etching Step

In step S7, a pattern is formed by etching or ion implanting a substrate as a base, with the resist pattern obtained after the development step S6 as a mask. The etching may be either dry etching under atmosphere such as plasma excitement, or wet etching involving immersion into a chemical. Following formation of the pattern on the substrate by the etching, the resist pattern is removed.

The resist pattern-forming method of the embodiment of the present invention including the patternwise exposure step S3 and the floodwise exposure step S4 can greatly increase the acid generated after exposure only in regions having been subjected to the patternwise exposure.

Figure 4:
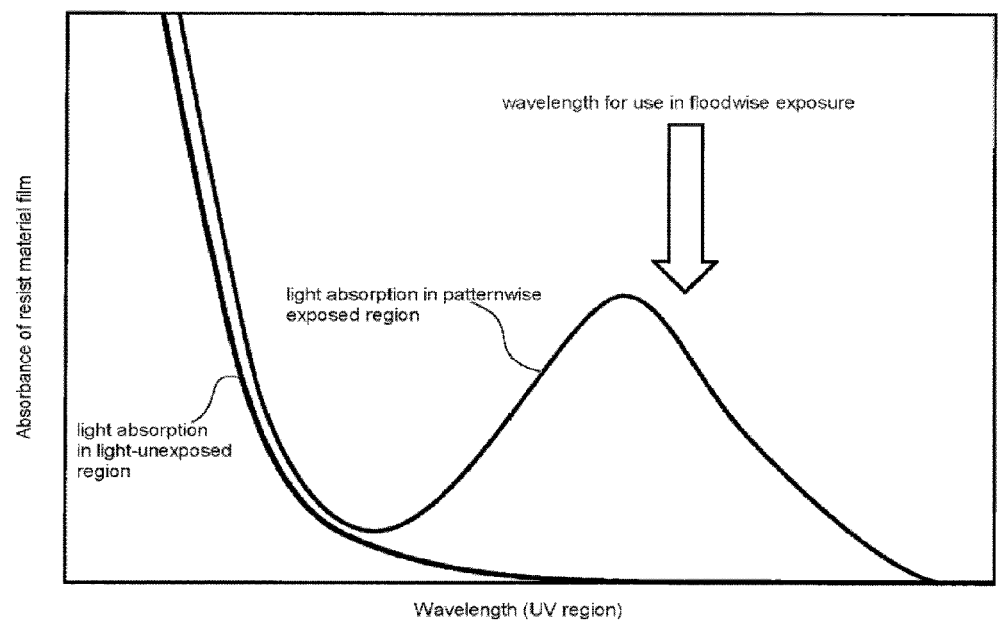
FIG. 4 shows a conceptual diagram illustrating a graph of the absorbance at a light-exposed region, and the absorbance at a light-unexposed region of a resist material film subjected to patterning.

FIG. 4 is a graph showing absorbance of the patternwise exposed regions and the light-unexposed regions of the resist material film upon the floodwise exposure. A site not subjected to the patternwise exposure (patternwise unexposed region) of the resist material film exhibits absorbance of an ultraviolet ray having a comparatively short wavelength, while not exhibiting absorbance of an ultraviolet ray having a long wavelength. On the other hand, in a site subjected to the patternwise exposure (patternwise exposed regions) of the resist material film, the acid and the radiation-sensitive sensitizer are generated as described above. The radiation-sensitive sensitizer thus generated absorbs nonionizing radiation having a wavelength exceeding 250 nm, and exhibits absorbance of an ultraviolet ray having a comparatively long wavelength. In the floodwise exposure, unlike in the patternwise exposure, an entire surface of the resist material film is irradiated with a radioactive ray without using a mask; however, in the patternwise unexposed regions, absorbance of the second radioactive ray in the floodwise exposure step S4 is low. Therefore, in the floodwise exposure step S4, an acid generating mechanism takes place in the patternwise exposed regions by predominantly the radiation-sensitive sensitizer. As a result, upon the floodwise exposure, an acid can be continuously generated only in the patternwise exposed regions, and sensitivity can thus be improved while maintaining lithography characteristics.

Figure 5A:
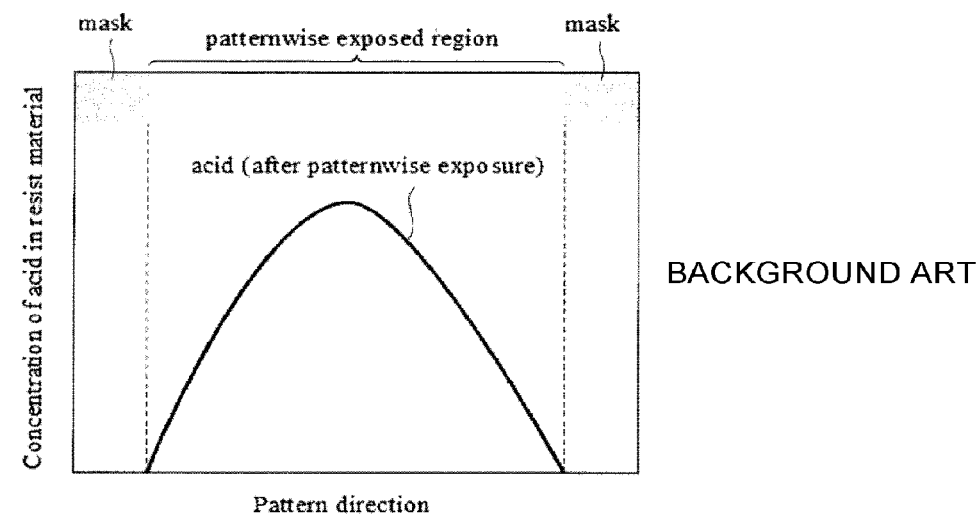
FIG. 5A shows conceptual diagrams illustrating a graph of acid concentration distribution by the resist pattern-forming method employing a conventional chemically amplified resist material.
Figure 5B:
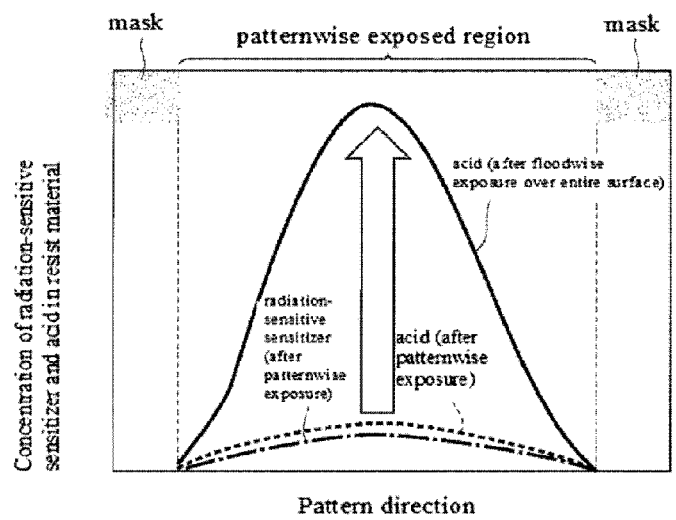
FIG. 5B shows a conceptual diagram illustrating a graph of radiation-sensitive sensitizer concentration distribution and acid concentration distribution by the resist pattern-forming method employing a chemically amplified resist material according to an embodiment of the present invention.

FIG. 5A shows conceptual diagrams illustrating a graph of acid concentration distribution by the resist pattern-forming method employing a conventional chemically amplified resist material. In the case of performing only the patternwise exposure with EUV or the like as in FIG. 2, a sufficient acid cannot be generated and sensitivity is lowered. Increasing the exposure dose for improving sensitivity deteriorates a latent image of the resist pattern (reduces lithography characteristics), thereby making it difficult to provide sensitivity and lithography characteristics simultaneously. FIG. 5B shows a conceptual diagram illustrating a graph of radiation-sensitive sensitizer concentration distribution and acid concentration distribution by the resist pattern-forming method employing a chemically amplified resist material according to the embodiment of the present invention. In the patternwise exposure, the latent image of the resist pattern is superior, while sufficient acid is not generated. However, following the floodwise exposure, an amount of the acid can be increased only in the patternwise exposed regions by the radiation-sensitive sensitizer generated in the patternwise exposure, and sensitivity can be thus improved with a small exposure dose while maintaining a superior latent image of the resist pattern. Since the acid generating mechanism by the radiation-sensitive sensitizer in the floodwise exposure takes place at room temperature, blurring of the latent image upon acid generation is mild, thereby allowing a great increase in sensitivity while maintaining the resolution.

Semiconductor Device

Figure 6A:
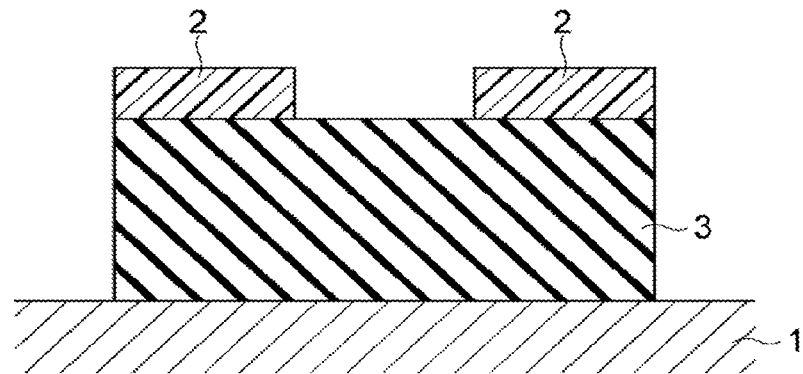
Figure 6B:
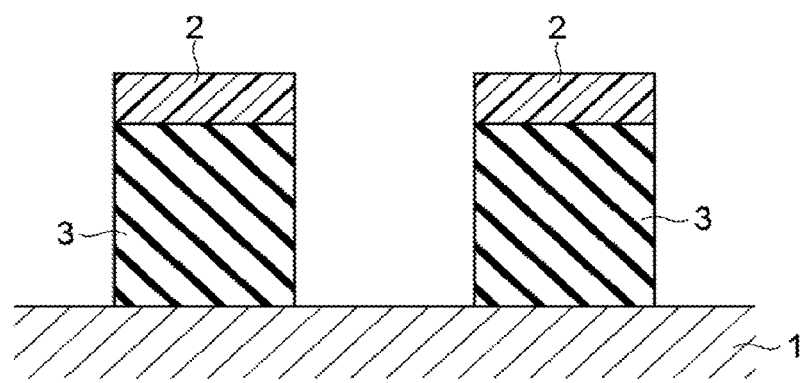
Figure 6C:
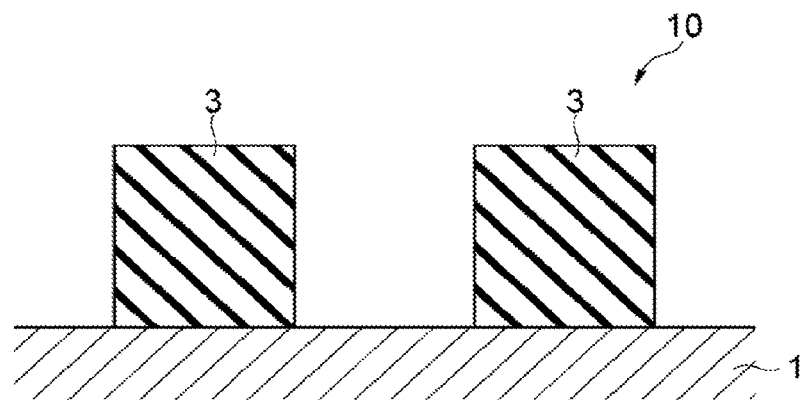

A semiconductor device according to the embodiment of the present invention is produced by using the resist pattern formed by the above-described method. FIGS. 6A to 6C show cross sectional views illustrating an example of a manufacturing step of the semiconductor device of the embodiment of the present invention.

FIG. 6A is a cross-sectional view showing a resist pattern forming step, the cross-sectional view illustrating a semiconductor wafer 1, an etched film 3 formed on the semiconductor wafer 1, and a resist pattern 2 formed on the etched film 3 by the above-described resist pattern-forming method (corresponding to a state after completion of the development step S6). Examples of the etched film include: an active layer, an under layer insulating film, a gate electrode film, and an upper layer insulating film. Between the etched film 3 and the resist pattern 2, an antireflective film, an underlayer film for resist adhesiveness amelioration, or an underlayer film for resist shape amelioration may be provided. In addition, a multilayer mask structure may also be employed. FIG. 6B is a cross sectional view showing an etching step, the cross-sectional view illustrating a semiconductor wafer 1, the resist pattern 2, and the etched film 3 being etched with the resist pattern 2 as a mask. The etched film 3 has been etched according to a shape of openings in the resist pattern 2. FIG. 6C is a cross sectional view of a pattern substrate 10 with the semiconductor wafer 1 and a pattern of the etched film 3 being etched, after removal of the resist pattern 2.

A semiconductor device can be formed by using a substrate provided with the pattern of the etched film 3. Examples of the forming method thereof include a method of embedding a wiring between the pattern of the etched film 3 from which the resist pattern 2 has been removed, and then overlaying a device element onto the substrate.

Lithography Mask

A lithography mask according to the embodiment of the present invention is produced by processing a substrate using the resist pattern formed by the above-described method. Examples of the production method thereof include a method of using the resist pattern for etching of a surface of a glass substrate or of a hard mask formed on a surface of a glass substrate. Here, the lithography mask includes a transmissive mask using an ultraviolet ray or an electron beam, and a reflection type mask using EUV. In the case of the lithography mask being a transmissive mask, the lithography mask can be produced by processing by etching while masking a light shielding part or a phase shift part with the resist pattern. On the other hand, in the case of the lithography mask being a reflection type mask, the lithography mask can be produced by processing a light absorbing body with the resist pattern as a mask.

Nanoimprinting Template

A nanoimprinting template according to the embodiment of the present invention can also be produced by using the resist pattern formed by the above-described method. The production method thereof is exemplified by, e.g., a method of including: forming a resist pattern on a surface of a glass substrate or on a surface of a hard mask formed on a surface of a glass substrate; and then processing by etching.

EXAMPLES

Hereinafter, the present invention is explained in detail by way of Examples, but the present invention is not in any way limited to these Examples. Measuring methods of physical property values in the present Examples are described below.

Weight Average Molecular Weight (Mw) and Number Average Molecular Weight (Mn)

Mw and Mn of a polymer were measured by gel permeation chromatography (GPC) with mono-dispersed polystyrene as a standard, using GPC columns (G2000 HXL×2, G3000 HXL×1 and G4000 HXL×1 (each available from Tosoh Corporation) under analysis conditions of: flow rate: 1.0 mL/min; elution solvent: tetrahydrofuran; sample concentration: 1.0% by mass; amount of injected sample: 100 μL; and column temperature: 40° C., using a differential refractometer as a detector.

$^{13}$C-NMR Analysis $^{13}$C-NMR analysis for determination of the proportion of the structural unit in the polymer was conducted by using a nuclear magnetic resonance apparatus ("JNM-ECX400" from JEOL, Ltd.), and DMSO-$d_6$ as a solvent for measurement, with tetramethylsilane (TMS) as an internal standard.

Synthesis of Base Polymer (A)

(1) Monomers used in the synthesis of the polymer (A) are shown below.

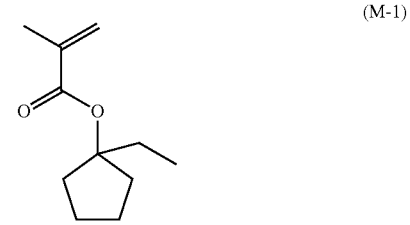

(M-1)

(M-2)

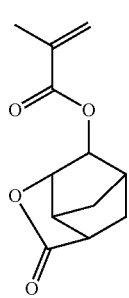

(M-3)

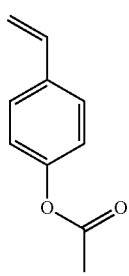

(M-4)

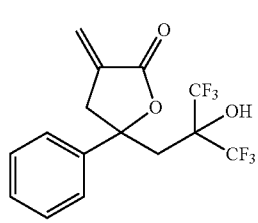

It is to be noted that: the compound (M-1) gives a structural unit (I); the compound (M-2) gives a structural unit (IV); the compound (M-3) gives a structural unit (III); and the compound (M-4) gives a structural unit (II).

Synthesis Example 1: Synthesis of Polymer (A-1)

55 g (50 mol %) of the compound (M-2), 45 g (50 mol %) of the compound (M-1) and 3 g of azobisisobutyronitrile (AIBN) were dissolved in 300 g of methyl ethyl ketone, followed by polymerizing for 6 hrs under a nitrogen atmosphere while maintaining a reaction temperature at 78° C. Following the polymerization, a reaction solution was added to 2,000 g of methanol dropwise to permit solidification of the polymer. Thereafter, the polymer was washed twice with 300 g of methanol and white powder thus obtained was filtered, followed by drying at 50° C. overnight under a reduced pressure, thereby obtaining a polymer (A-1) served as the polymer (A). The polymer (A-1) had the Mw of 7,000 and the Mw/Mn of 2.10. In addition, the result of $^{13}$C-NMR analysis indicated that the proportions of the structural units derived from the compound (M-1) and the compound (M-2) were 52 mol % and 48 mol %, respectively.

Synthesis Example 2: Synthesis of Polymer (A-2)

55 g (58 mol %) of the compound (M-3), 45 g (42 mol %) of the compound (M-1), 3 g of AIBN and 1 g of t-dodecyl mercaptan were dissolved in 150 g of propylene glycol monomethyl ether, followed by polymerizing for 16 hrs under a nitrogen atmosphere while maintaining a reaction temperature at 70° C. Following the polymerization, a reaction solution was added to 1,000 g of n-hexane dropwise to permit solidification and purification of a polymer. Subsequently, 150 g of propylene glycol monomethyl ether was added again to the polymer, then 150 g of methanol, 37 g of trimethylamine and 7 g of water were further added thereto, and a hydrolysis reaction was allowed to proceed for 8 hrs with refluxing at the boiling point to permit deacetylation of the structural unit derived from (M-3). After the reaction, the solvent and triethylamine were distilled off under reduced pressure, the resulting polymer was dissolved in 150 g of acetone, and then the solution thus obtained was added to 2,000 g of water dropwise to permit solidification of the polymer. The white powder thus formed was filtered off, followed by drying at 50° C. overnight under a reduced pressure to obtain a polymer (A-2), which served as the polymer (A). The polymer (A-2) had the Mw of 6,000 and the Mw/Mn of 1.90. In addition, the result of $^{13}$C-NMR analysis indicated that the proportions of the p-hydroxystyrene structural unit obtained by deacetylation of a structural unit derived from the compound (M-3), and the structural unit derived from the compound (M-1) were 50 mol % and 50 mol %, respectively.

Synthesis Example 3: Synthesis of Polymer (A-3)

A monomer solution was prepared by dissolving 6.99 g (40 mol %) of the compound (M-1), 6.22 g (40 mol %) of the compound (M-3) and 6.79 g (20 mol %) of the compound (M-4) in 40 g of propylene glycol monomethyl ether, and further dissolving 0.79 g (5 mol % with respect to the total number of moles of the compounds) of AIBN as a radical polymerization initiator. Into a 100-ml three-neck flask was charged 20 g of propylene glycol monomethyl ether, followed by nitrogen-purging for 30 min. Thereafter, the reaction vessel was heated to 80° C. with stirring. The monomer solution prepared as described above was added thereto dropwise over 3 hrs, followed by aging for additional 3 hrs. After completing the polymerization, the polymerization reaction mixture was cooled with water to 30° C. or below. The cooled polymerization reaction mixture was charged into 400 g of hexane, and the precipitated solid contents were filtered off. The solid contents collected by the filtration were washed with 80 g of hexane twice, and then further filtered off, followed by drying at 50° C. for 17 hrs. The solid contents were charged into a 100-mL eggplant-shaped flask containing 20 g of propylene glycol monomethyl ether, whereby the dissolution was allowed. Furthermore, 3.49 g of triethylamine and 0.56 g of pure water were added thereto, and the mixture was heated to 80° C., followed by allowing for reaction for 6 hrs to permit hydrolysis. After completing the hydrolysis, the reaction mixture was cooled with water to 30° C. or below. This reaction mixture was charged into 400 g of hexane, and the precipitated solid contents were filtered off. The solid contents collected by the filtration were washed with 80 g of hexane twice, and then further filtered off, followed by drying at 50° C. for 17 hrs to obtain a polymer (A-3) in an amount of 12.2 g (yield: 61%). The polymer (A-3) had the Mw of 7,500, and the Mw/Mn of 1.52. The result of the $^{13}$C-NMR analysis indicated that the proportions of the structural unit derived from (M-1), the p-hydroxystyrene structural unit obtained by deacetylation of the structural unit derived from (M-3), and the structural unit derived from (M-4) were 40 mol %, 40 mol %, and 20 mol %, respectively. Table 1 shows the Mw, the Mw/Mn and the proportion of each structural unit of the obtained polymers (A-1) to (A-3).

TABLE 1

| (A) Polymer | Monomer type | Proportion of structural unit (% by mole) | Mw | Mw/Mn |
|---|---|---|---|---|
| Synthesis Example 1 | A-1 | M-1 52<br>M-2 48 | 7,000 | 2.10 |
| Synthesis Example 2 | A-2 | M-1 50<br>M-3 50 | 6,000 | 1.90 |
| Synthesis Example 3 | A-3 | M-1 40<br>M-3 40<br>M-4 20 | 7,500 | 1.52 |

* In Table, the proportion of the structural unit of M-3 indicates the proportion in terms of the p-hydroxystyrene structural unit obtained by deacetylation of the structural unit unit derived from M-3.

(2) Component that Generates Radiation-Sensitive Sensitizer and Acid Upon Exposure (b) Radiation-Sensitive Sensitizer Generating Agent The following compounds were used as the radiation-sensitive sensitizer generating agent (b).

B-1: a compound represented by the following formula (B-1)

B-2: a compound represented by the following formula (B-2)

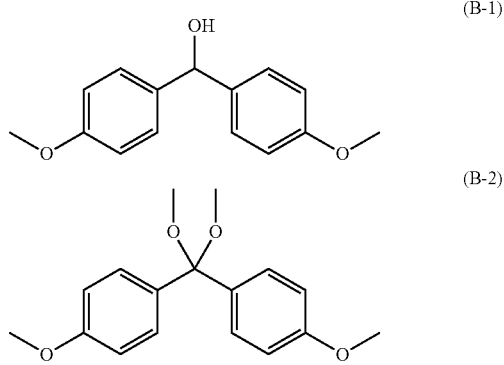

(B-1)

(B-2)

Absorbance Measurement of Component (b)

The component (b) and the sensitizing agent derived from the component (b) are shown together in Table 2. With respect to each of the components (b) and the sensitizing agents derived from the components (b), a 0.0001% by mass cyclohexane solution thereof was prepared. The absorbance of the solution prepared thus was measured using cyclohexane as a reference solvent and a spectrophotometer ("V-670" available from JASCO Corporation).

At each wavelength falling within the range of no less than 250 nm and no greater than 600 nm, the absorbance was determined by subtracting the absorbance of the reference solvent from the absorbance of the solution to be measured. The absorbance was evaluated to be: "transparent" in a case where the measurement value of the absorbance was less than 0.01 over the entire wavelength range of no less than 300 nm and no greater than 450 nm; and "absorbing" in a case where the measurement value of the absorbance was no less than 0.01 at at least one wavelength within the entire wavelength range of no less than 300 nm and no greater than 450 nm. The results of the evaluations are shown in Table 3. It is to be noted that the transmittance of cyclohexane which was a solvent used for the measurement of the absorption spectrometry was ascertained to be no less than 95% at each wavelength falling within the range of no less than 250 nm and no greater than 600 nm.

TABLE 2

| | (b) Component | Compound name of component (b) | Sensitizing agent derived from component (b) | Compound name of sensitizing agent derived from component (b) |
|---|---|---|---|---|
| Synthesis Example 4 | B-1 | bis(4-methoxyphenyl)methanol | D-1 | 4,4'-dimethoxybenzophenone |
| Synthesis Example 5 | B-2 | 4,4'-dimethoxybenzophenone dimethyl ketal | D-2 | 4,4'-dimethoxybenzophenone |

TABLE 3

| | (b) Component | Absorbance (300-450 nm) | Sensitizing agent derived from component (b) | Absorbance (300-450 nm) |
|---|---|---|---|---|
| Synthesis Example 4 | B-1 | transparent | D-1 | absorbing |
| Synthesis Example 5 | B-2 | transparent | D-2 | absorbing |

(c) Radiation-Sensitive Acid Generating Agent

As the radiation-sensitive acid generating agent (c), the compound (C1) (first compound) and the compound (C2) (second compound) were used.

Acid Generating Compound

In Examples, of the compound (C1) (first compound) and the compound (C2) (second compound), the following compounds (C1) being the compound that is capable of generating the acid having a smaller pKa were used as the acid generating compound.

C-1-1: a compound represented by the following formula (C-1-1)

C-1-2: a compound represented by the following formula (C-1-2)

C-1-3: a compound represented by the following formula (C-1-3)

C-1-4: a compound represented by the following formula (C-1-4)

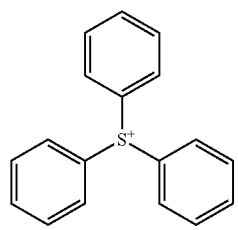

(C-1-1)

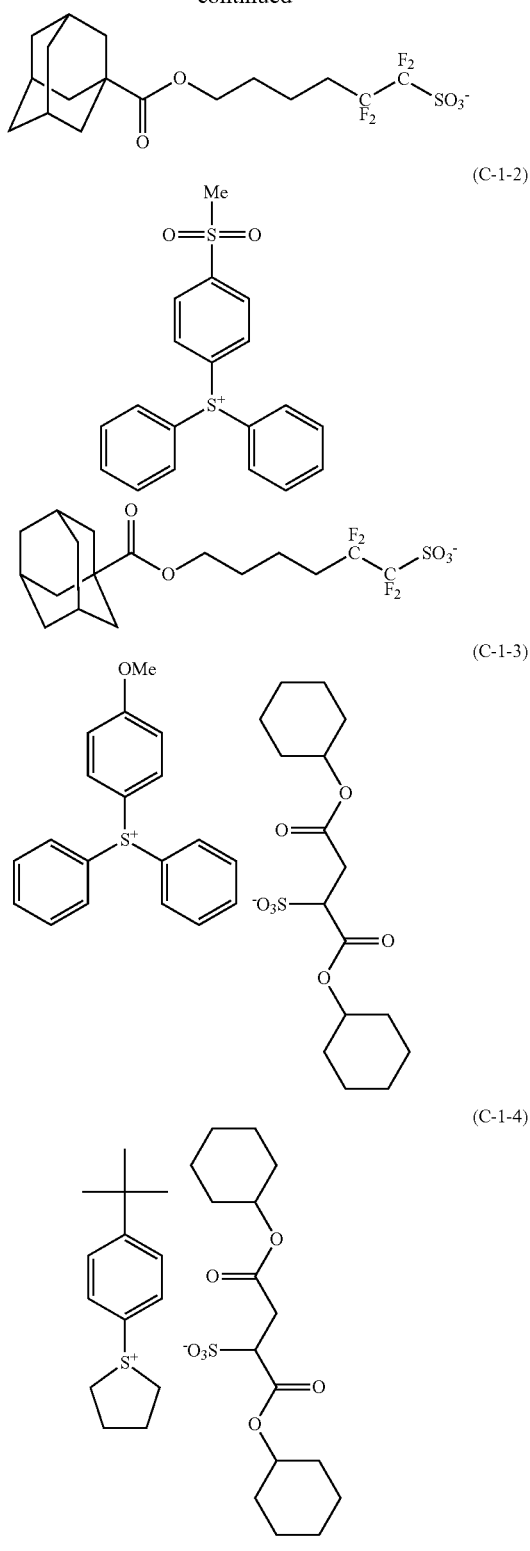

Energy Released Upon Reduction of Acid Generating Compound (Compound (C1)) Cation to Radical Furthermore, with regard to the compounds (C-1-1) to (C-1-4), calculated results of each energy released upon reduction of a cation in these compounds to a radical are shown in Table 4. Here, after carrying out structure optimization of each cation and radical, an energy level of each substance was obtained by the B3LYP/LANL2DZ method, and then the energy was calculated from an energy difference between a cation and a radical.

TABLE 4

| (C1) Compound | pKa of acid generated | Energy released from cation (eV) |
| --- | --- | --- |
| C-1-1 | −2.32 | 4.92 |
| C-1-2 | −2.32 | 5.33 |
| C-1-3 | −0.81 | 4.77 |
| C-1-4 | −0.81 | 5.18 |

Acid Diffusion Control Agent

In Examples, of the compound (C1) (first compound) and the compound (C2) (second compound), the following compounds (C2) (C-2-1 and C-2-4) being the compound that is capable of generating the acid having a greater pKa were used as the acid diffusion control agent. Moreover, in Comparative Examples, C-2-1 to C-2-5 were used as the acid diffusion control agent.

C-2-1: a compound represented by the following formula (C-2-1) (being radiation-sensitive)

C-2-2: a compound represented by the following formula (C-2-2) (being radiation-insensitive)

C-2-3: a compound represented by the following formula (C-2-3) (being radiation-sensitive)

C-2-4: a compound represented by the following formula (C-2-4) (being radiation-sensitive)

C-2-5: a compound represented by the following formula (C-2-5) (being radiation-sensitive)

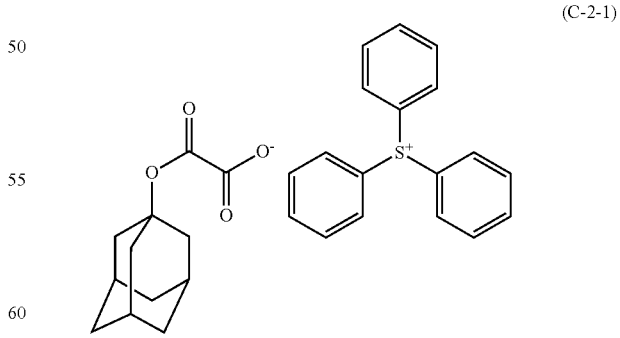

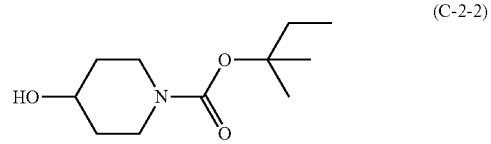

pKa of Acid Generated from Acid Generating Compound (Compound (C1)

In regard to the compounds (C-1-1) to (C-1-4), the pKa (logarithmic value of the reciprocal number of the acid dissociation constant) of the acid generated from these compounds is shown in Table 4.

-continued (C-2-3)
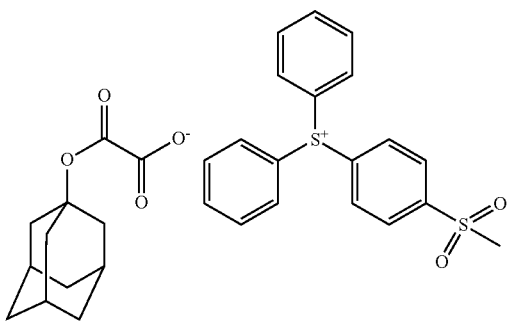

(C-2-4)
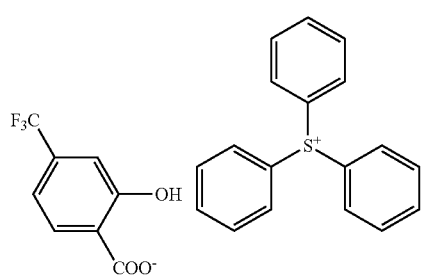

(C-2-5)
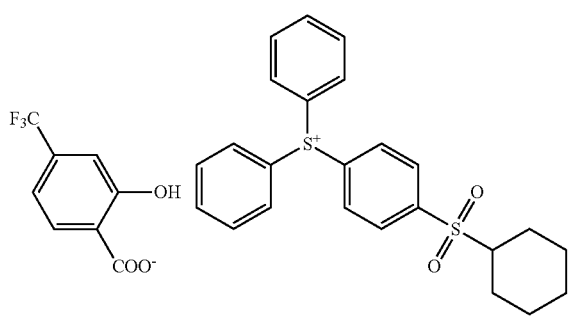

pKa of Acid Generated from Acid Diffusion Control Agent (Compound (C2))

In regard to the compounds (C-2-1), (C-2-3), (C-2-4) and (C-2-5), the acid diffusion control agents being radiation-sensitive, the pKa (logarithmic value of the reciprocal number of the acid dissociation constant) of the acid (anionic moiety) generated from these compounds is shown in Table 5.

Energy Released Upon Reduction of Cation in Acid Diffusion Control Agent (Compound (C2)) to Radical Also, with regard to the compounds (the compounds (C-2-1), (C-2-3), (C-2-4) and (C-2-5), the acid diffusion control agents being radiation-sensitive), calculated results of each energy released upon reduction of a cation in these compounds to a radical are shown in Table 5. Here, after carrying out structure optimization of each cation and radical, an energy level of each substance was obtained by the B3LYP/LANL2DZ method, and then the energy was calculated from an energy difference between a cation and a radical.

TABLE 5

| (C2) Compound | pKa of anion generated | Energy released from cation (eV) |
|---|---|---|
| C-2-1 | 2.69 | 4.92 |
| C-2-3 | 2.69 | 5.33 |
| C-2-4 | 2.76 | 4.92 |
| C-2-5 | 2.76 | 5.36 |

Solvent

G-1: propylene glycol monomethyl ether acetate

G-2: ethyl lactate

Example 1

100 parts by mass of (A) the polymer (A-1); 5 parts by mass of (b) the radiation-sensitive sensitizer generating agent (B-1); 15 parts by mass of (C1) the compound (C-1-1) and 5.0 parts by mass (C2) the compound (C-2-1) as the radiation-sensitive acid generating agent (c); and 4,300 parts by mass of the solvent (G-1) and 1,900 parts by mass of the solvent (G-2) were mixed. Next, the mixture solution thus obtained was filtered through a membrane filter having a pore size of 0.20 μm to prepare a chemically amplified resist material (R-1).

Examples 2 to 3 and Comparative Examples 1 to 10

Chemically amplified resist materials (R-2) to (R-13) were prepared by a similar operation to that for Example 1, except for using components of the types and in proportions specified in Table 6. It is to be noted that "–" in Table indicates the absence of the corresponding component.

TABLE 6

| | Chemically amplified resist material | (A) Polymer type | proportion (parts by mass) | (b) Component type | proportion (parts by mass) | (c) Component |  |  |  | Solvent |  |
|---|---|---|---|---|---|---|---|---|---|---|---|
| | | | | | | (C1) compound type | proportion (parts by mass) | (C2) compound type | proportion (parts by mass) | type | proportion (parts by mass) |
| Example 1 | R-1 | A-1 | 100 | B-1 | 5 | C-1-1 | 15 | C-2-1 | 5.0 | G-1/G-2 | 4,300/1,900 |
| Comparative Example 1 | R-2 | A-1 | 100 | B-1 | 5 | C-1-2 | 15 | C-2-1 | 5.0 | G-1/G-2 | 4,300/1,900 |
| Comparative Example 2 | R-3 | A-1 | 100 | B-1 | 5 | C-1-1 | 15 | C-2-2 | 5.0 | G-1/G-2 | 4,300/1,900 |
| Comparative Example 3 | R-4 | A-1 | 100 | B-1 | 5 | C-1-1 | 15 | C-2-3 | 5.0 | G-1/G-2 | 4,300/1,900 |
| Comparative Example 4 | R-5 | A-1 | 100 | — | — | C-1-1 | 15 | C-2-1 | 5.0 | G-1/G-2 | 4,300/1,900 |

TABLE 6-continued

| | Chemically amplified resist material | (A) Polymer | | (b) Component | | (c) Component | | | | Solvent | |
|---|---|---|---|---|---|---|---|---|---|---|---|
| | | | | | | (C1) compound | | (C2) compound | | | |
| | | type | proportion (parts by mass) | type | proportion (parts by mass) | type | proportion (parts by mass) | type | proportion (parts by mass) | type | proportion (parts by mass) |
| Example 2 | R-6 | A-2 | 100 | B-2 | 5 | C-1-3 | 25 | C-2-4 | 5.0 | G-1/G-2 | 4.300/1,900 |
| Comparative Example 5 | R-7 | A-2 | 100 | B-2 | 5 | C-1-4 | 25 | C-2-4 | 5.0 | G-1/G-2 | 4,300/1,900 |
| Comparative Example 6 | R-8 | A-2 | 100 | B-2 | 5 | C-1-3 | 25 | C-2-5 | 5.0 | G-1/G-2 | 4,300/1,900 |
| Comparative Example 7 | R-9 | A-2 | 100 | — | — | C-1-3 | 25 | C-2-4 | 5.0 | G-1/G-2 | 4,300/1,900 |
| Example 3 | R-10 | A-3 | 100 | B-2 | 5 | C-1-3 | 20 | C-2-1 | 5.0 | G-1/G-2 | 4,300/1,900 |
| Comparative Example 8 | R-11 | A-3 | 100 | B-2 | 5 | C-1-4 | 20 | C-2-1 | 5.0 | G-1/G-2 | 4,300/1,900 |
| Comparative Example 9 | R-12 | A-3 | 100 | B-2 | 5 | C-1-3 | 20 | C-2-3 | 5.0 | G-1/G-2 | 4,300/1,900 |
| Comparative Example 10 | R-13 | A-3 | 100 | — | — | C-1-3 | 20 | C-2-1 | 5.0 | G-1/G-2 | 4,300/1,900 |

Formation of Resist Pattern

The chemically amplified resist material prepared as described above was spin-coated onto a silicon wafer in "CLEAN TRACK ACT-8" available from Tokyo Electron Limited, and subjected to PB at 100° C. for 60 sec to form a resist material film having an average thickness of 50 nm. Subsequently, the resist material film was irradiated with an electron beam using a simplified electron beam writer ("HL800D" available from Hitachi, Ltd., power: 50 KeV, current density: 5.0 A/cm$^2$) to permit patterning. The patterning was a line and space pattern (1L 1S) obtained by using a mask configured with a line part having a line width of 150 nm and a space part formed by neighboring line parts with an interval of 150 nm. After the irradiation with the electron beam for patterning, each of the following operations (1) to (3) was evaluated.

Operation (1): Without Floodwise Exposure

After the irradiation with the electron beam, PEB was carried out at 110° C. for 60 sec in the CLEAN TRACK ACT-8. Then, a development was carried out according to the puddle procedure at 23° C. for 1 min using a 2.38% by mass aqueous tetramethylammonium hydroxide (THAM) solution in the CLEAN TRACK ACT-8. Following the exposure, the substrate was washed with pure water, followed by drying, whereby a positive resist pattern was formed.

Operation (2): With Floodwise Exposure (10 Min)

After the irradiation with the electron beam, the entire face of the resist material film was subjected to the floodwise exposure for 10 min using a black light lamp (Toshiba Corporation, wavelength: 320 nm). Subsequently, in the CLEAN TRACK ACT-8, PEB was carried out under conditions of 110° C. and 60 sec. Thereafter, development, washing and drying was carried out in a similar manner to that in the operation (1), whereby a positive resist pattern was formed.

Operation (3): With Floodwise Exposure (30 Min)

After the irradiation with the electron beam, the entire face of the resist material film was subjected to the floodwise exposure for 30 min using a black light lamp (Toshiba Corporation, wavelength: 320 nm). Subsequently, in the CLEAN TRACK ACT-8, PEB was carried out under conditions of 110° C. and 60 sec. Thereafter, development, washing and drying was carried out in a similar manner to that in the operation (1), whereby a positive resist pattern was formed.

Evaluations

The positive resist patterns formed as described above were evaluated for the sensitivity and the nanoedge roughness according to the following procedure.

Sensitivity

An exposure dose at which a line and space pattern (1L 1S) configured with a line part having a line width of 150 nm and a space part formed by neighboring line parts with an interval of 150 nm was formed to give a line width of 1:1 was defined as "optimal exposure dose", and the "optimal exposure dose" was used as a standard for the sensitivity. The sensitivity was evaluated to be: "A (favorable)" in the case of the optimal exposure dose being no less than 50 μC/cm$^2$; and "B (unfavorable)" in the case of greater than 50 μC/cm$^2$. Measured values of the optimal exposure dose and evaluation results of the sensitivity are shown in Table 7.

Nanoedge Roughness

Figure 7:
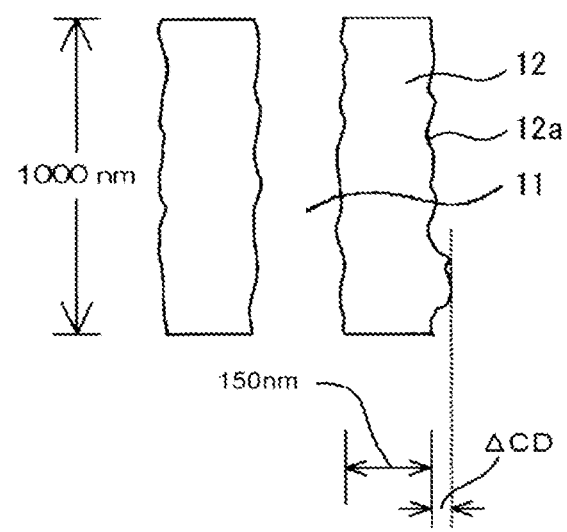
FIG. 7 shows a schematic plan view illustrating the nanoedge roughness of a pattern.
Figure 8:
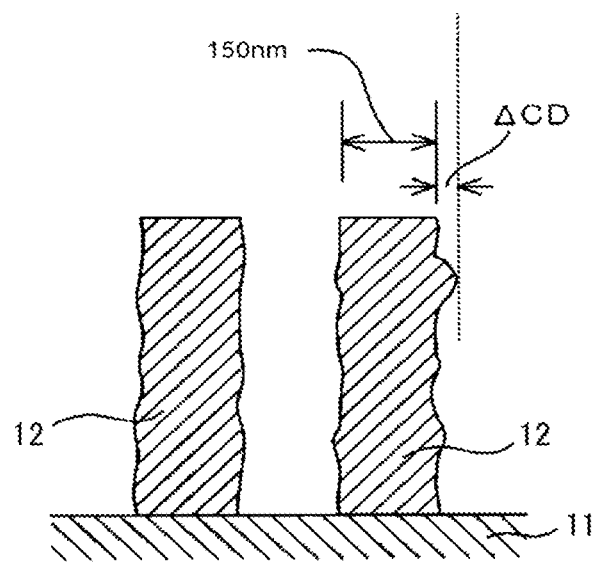
FIG. 8 shows a schematic cross sectional view illustrating the nanoedge roughness of the pattern.

The line patterns of the line and space pattern (1L 1S) were observed using a high-resolution FEB critical dimension measurement device (S-9220, available from Hitachi, Ltd.) at arbitrary twenty points on the line pattern. With respect to the points at which the observation was made, as shown in FIGS. 7 and 8, a difference "ΔCD" between an intended line width of 150 nm and a line width in an area in which irregularities generated along side lateral surface 12a of the line part 12 of the pattern formed on the substrate (silicon wafer) 11 was most significant was measured. The average value of the ΔCD of the twenty points was used as a standard for the nanoedge roughness. The nanoedge roughness was evaluated to be: "AA (extremely favorable)" in the case of the average value of ΔCD (nm) being no greater than 12.0 nm; "A (favorable)" in the case of greater than 12.0 nm and no greater than 15.0 nm; and "B (unfavorable)" in the case of greater than 15.0 nm. It is to be noted that the irregularities shown in FIGS. 7 and 8 are exaggerated. The average values of the ΔCD and evaluation results of the nanoedge roughness are shown in Table 7.

TABLE 7

| | Chemically amplified resist material | Evaluation results of operation (1) | | | | Evaluation results of operation (2) | | | | Evaluation results of operation (3) | | | |
|---|---|---|---|---|---|---|---|---|---|---|---|---|---|
| | | sensitivity | | nanoedge roughness | | sensitivity | | nanoedge roughness | | sensitivity | | nanoedge roughness | |
| | | optimum exposure dose ($\mu C/cm^2$) | evaluation | average value of $\Delta CD$ (nm) | evaluation | optimum exposure dose ($\mu C/cm^2$) | evaluation | average value of $\Delta CD$ (nm) | evaluation | optimum exposure dose ($\mu C/cm^2$) | evaluation | average value of $\Delta CD$ (nm) | evaluation |
| Example 1 | R-1 | 62.4 | B | 14.5 | A | 52.4 | B | 14.4 | A | 42.4 | A | 14.3 | A |
| Comparative Example 1 | R-2 | 61.4 | B | 14.3 | A | 50.2 | B | 14.6 | A | 35.2 | A | 17.6 | B |
| Comparative Example 2 | R-3 | 63.4 | B | 13.9 | A | 55.3 | B | 14.4 | A | 51.3 | B | 14.2 | A |
| Comparative Example 3 | R-4 | 62.1 | B | 14.6 | A | 50.2 | B | 14.2 | A | 40.3 | A | 15.5 | B |
| Comparative Example 4 | R-5 | 63.1 | B | 14.7 | A | 62.1 | B | 14.7 | A | 61.4 | B | 14.8 | A |
| Example 2 | R-6 | 63.5 | B | 14.2 | A | 51.2 | B | 14.5 | A | 44.8 | A | 14.3 | A |
| Comparative Example 5 | R-7 | 63.1 | B | 13.8 | A | 50.1 | B | 13.9 | B | 41.8 | A | 15.9 | B |
| Comparative Example 6 | R-8 | 63.5 | B | 14.1 | A | 50.9 | B | 14.2 | B | 42.3 | A | 15.3 | B |
| Comparative Example 7 | R-9 | 62.8 | B | 14.2 | A | 61.1 | B | 14.4 | B | 60.4 | B | 14.5 | B |
| Example 3 | R-10 | 59.2 | B | 11.5 | AA | 53.4 | B | 11.8 | AA | 35.2 | A | 11.9 | AA |
| Comparative Example 8 | R-11 | 59.3 | B | 11.9 | AA | 50.3 | B | 11.9 | AA | 31.4 | A | 15.2 | B |
| Comparative Example 9 | R-12 | 59.9 | B | 11.8 | AA | 50.7 | B | 11.8 | AA | 33.3 | A | 15.1 | B |
| Comparative Example 10 | R-13 | 59.5 | B | 11.7 | AA | 59.0 | B | 11.9 | AA | 58.2 | B | 11.9 | A |

As shown in Table 7, according to Examples that included as the radiation-sensitive acid generating agent being the component (c), the radiation-sensitive compounds (C1) and (C2) each including the onium cation that released the energy of less than 5.0 eV upon the reduction to a radical, it was ascertained that favorable sensitivity was attained without being accompanied by inferior nanoedge roughness even in the case with a high dose of UV upon the floodwise exposure. On the other hand, in the case of Comparative Examples that included the compounds (C1) and (C2) either one of which including the onium cation that released the energy of no less than 5.0 eV upon the reduction to a radical, the sensitivity increased without being accompanied by inferior nanoedge roughness when the dose of UV upon the floodwise exposure is less, but inferior nanoedge roughness was found with the exposure dose higher than a certain value provided by, e.g., the exposure for a time period of 30 min. Furthermore, in the case of Comparative Examples that included the radiation-insensitive compound as the acid diffusion control agent in place of the radiation-sensitive compound (C2), it was ascertained that the increase in the sensitivity upon the floodwise exposure to UV was inhibited.

As described in the foregoing, the chemically amplified resist material and the resist pattern-forming method of the embodiments of the present invention enable superior lithography performances to be achieved while favorable sensitivity is maintained, in the case of using as the patterning exposure light, ionizing radiation such as EUV, an electron beam and an ion beam, or nonionizing radiation having a wavelength of no greater than 250 nm such as a KrF excimer laser and an ArF excimer laser. In addition, the chemically amplified resist material can be suitably used in the resist pattern-forming method.

Obviously, numerous modifications and variations of the present invention are possible in light of the above teachings. It is therefore to be understood that within the scope of the appended claims, the invention may be practiced otherwise than as specifically described herein.

The invention claimed is:
1. A chemically amplified resist material comprising:
a polymer component that is capable of being made soluble or insoluble in a developer solution by an action of an acid; and
a generative component that is capable of generating a radiation-sensitive sensitizer and an acid upon an exposure,
wherein the generative component comprises:
at least one radiation-sensitive acid-and-sensitizer generating agent;
the at least one radiation-sensitive acid-and-sensitizer generating agent and at least one a radiation-sensitive sensitizer generating agent;
the at least one radiation-sensitive acid-and-sensitizer generating agent and at least one radiation-sensitive acid generating agent;
the at least one a radiation-sensitive sensitizer generating agent and the at least one radiation-sensitive acid generating agent; or
all the at least one radiation-sensitive acid-and-sensitizer generating agent, the at least one radiation-sensitive sensitizer generating agent, and the at least one radiation-sensitive acid generating agent,
wherein
the radiation-sensitive acid-and-sensitizer generating agent is capable of generating, upon an exposure to a first radioactive ray having a wavelength of no greater than 250 nm without an exposure to a second radioactive ray having a wavelength of greater than 250 nm, an acid and a radiation-sensitive sensitizer that absorbs the second radioactive ray, but the radiation-sensitive acid-and-sensitizer generating agent substantially does not generate the acid and the radiation-sensitive sensitizer upon an exposure to the second radioactive ray without an exposure to the first radioactive ray, the radiation-sensitive sensitizer generating agent is capable of generating, upon the exposure to the first radioactive ray without the exposure to the second radioactive ray, a radiation-sensitive sensitizer that absorbs the second radioactive ray, but the radiation-sensitive sensitizer generating agent substantially does not generate the radiation-sensitive sensitizer upon the exposure to the second radioactive ray without the exposure to the first radioactive ray, and the radiation-sensitive acid generating agent is capable of generating an acid upon the exposure to the first radioactive ray without the exposure to the second radioactive ray, but the radiation-sensitive acid generating agent substantially does not generate the acid upon the exposure to the second radioactive ray without the exposure to the first radioactive ray, and wherein the generative component comprises a first compound and a second compound each of which is the radiation-sensitive acid-and-sensitizer generating agent, if present in the generative component, or the radiation-sensitive acid generating agent, if present in the generative component, the first compound is radiation sensitive and comprises a first onium cation and a first anion, and the second compound is radiation sensitive and comprises a second onium cation and a second anion that is different from the first anion, and each of an energy released upon reduction of the first onium cation to a radical and an energy released upon reduction of the second onium cation to a radical is less than 5.0 eV.

2. The chemically amplified resist material according to claim 1, wherein a total percentage content of the first onium cation and the second onium cation with respect to total onium cations in the chemically amplified resist material is no less than 80 mol %.

3. The chemically amplified resist material according to claim 1, wherein a logarithmic value of a reciprocal number of an acid dissociation constant of the acid generated from at least one of the first compound and the second compound is no greater than 0.

4. The chemically amplified resist material according to claim 1, wherein the polymer component comprises a first polymer comprising a structural unit which comprises a group that is capable of generating a polar group by an action of an acid.

5. The chemically amplified resist material according to claim 4, wherein the first polymer comprises a structural unit that comprises a fluorine atom, or the polymer component comprises a second polymer that is different from the first polymer, the second polymer having a structural unit that comprises a fluorine atom.

6. The chemically amplified resist material according to claim 1, wherein the generative component is different from the polymer component.

7. The chemically amplified resist material according to claim 6, wherein a content of the generative component with respect to a total solid content is no less than 10% by mass and no greater than 30% by mass.

8. A resist pattern-forming method comprising:
applying the chemically amplified resist material according to claim 1 on at least one face of a substrate to form a resist material film;
patternwise exposing the resist material film to a radioactive ray having a wavelength of no greater than 250 nm;
floodwise exposing to a radioactive ray having a wavelength of greater than 250 nm, the resist material film patternwise exposed;
baking the resist material film floodwise exposed; and
developing with a developer solution, the resist material film baked.

9. The chemically amplified resist material according to claim 1, wherein each of the energy released upon reduction of the first onium cation to a radical and the energy released upon reduction of the second onium cation to a radical is at most 4.9 eV.

10. The chemically amplified resist material according to claim 1, wherein each of the energy released upon reduction of the first onium cation to a radical and the energy released upon reduction of the second onium cation to a radical is at most 4.8 eV.

11. The chemically amplified resist material according to claim 1, wherein each of the energy released upon reduction of the first onium cation to a radical and the energy released upon reduction of the second onium cation to a radical is at least 4.0 eV.

12. The chemically amplified resist material according to claim 1, wherein each of the energy released upon reduction of the first onium cation to a radical and the energy released upon reduction of the second onium cation to a radical is at least 4.2 eV.

13. The chemically amplified resist material according to claim 1, wherein a pKa of the acid generated from one of the first compound and the second compound is at most 0, and a pKa of the acid generated from the other of the first compound and the second compound is at least 1.

14. The chemically amplified resist material according to claim 1, wherein a pKa of the acid generated from one of the first compound and the second compound is at most −0.5, and a pKa of the acid generated from the other of the first compound and the second compound is at least 0.

15. The chemically amplified resist material according to claim 1, wherein a pKa of the acid generated from one of the first compound and the second compound is at most −0.5, and a pKa of the acid generated from the other of the first compound and the second compound is at least 1.

* * * * *